(12) United States Patent
Tran et al.

(10) Patent No.: US 10,499,216 B2
(45) Date of Patent: *Dec. 3, 2019

(54) SMART DEVICE

(71) Applicant: Bao Tran, Saratoga, CA (US)

(72) Inventors: Bao Tran, Saratoga, CA (US); Ha Tran, Saratoga, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/990,550

(22) Filed: May 25, 2018

(65) Prior Publication Data
US 2018/0288586 A1 Oct. 4, 2018

Related U.S. Application Data

(63) Continuation of application No. 15/144,773, filed on May 2, 2016, now Pat. No. 9,610,476, and a
(Continued)

(51) Int. Cl.
G06T 17/00 (2006.01)
H04W 4/38 (2018.01)
(Continued)

(52) U.S. Cl.
CPC ............ *H04W 4/38* (2018.02); *A42B 3/0433* (2013.01); *A61B 5/11* (2013.01); *A61B 5/6804* (2013.01); *A63B 24/0006* (2013.01); *A63B 24/0021* (2013.01); *A63B 24/0062* (2013.01); *A63B 24/0075* (2013.01); *A63B 43/004* (2013.01); *A63B 60/46* (2015.10); *A63B 69/36* (2013.01); *A63B 69/38* (2013.01); *A63B 71/06* (2013.01); *A63B 71/145* (2013.01); *A63F 11/00* (2013.01); *A63F 13/211* (2014.09); *B33Y 10/00* (2014.12); *G01L 5/0052* (2013.01); *G06F 1/163* (2013.01); *G06F 3/00* (2013.01); *G06F 3/017* (2013.01); *G06K 9/00342* (2013.01); *G06K 9/00355* (2013.01); *G06K 9/00671* (2013.01); *G06K 19/025* (2013.01); *G06K 19/07762* (2013.01); *G06Q 40/08* (2013.01); *G09B 19/003* (2013.01); *G09B 19/0038* (2013.01); *G16H 20/30* (2018.01); *G16H 30/20* (2018.01); *G16H 40/63* (2018.01); *G16H 40/67* (2018.01); *H04N 5/2253* (2013.01); *H04N 7/18* (2013.01); *H04Q 9/00* (2013.01); *H04W 84/18* (2013.01); *A61B 5/0022* (2013.01); *A61B 5/01* (2013.01); *A61B 5/024* (2013.01); *A61B 5/0402* (2013.01); *A61B 5/053* (2013.01); *A61B 5/055* (2013.01); *A61B 5/0533* (2013.01); *A61B 5/4872* (2013.01); *A61B 5/6806* (2013.01); *A61B 5/6895* (2013.01); *A61B 2503/10* (2013.01); *A61B 2562/0219* (2013.01); *A63B 21/072* (2013.01); *A63B 21/0724* (2013.01); *A63B 21/0726* (2013.01); *A63B 69/0002* (2013.01);
(Continued)

(58) Field of Classification Search
USPC .................................................... 463/16–42
See application file for complete search history.

(56) References Cited

U.S. PATENT DOCUMENTS 9,076,045 B2 * 7/2015 Atsmon ............ G01C 21/3602
2016/0357187 A1 * 12/2016 Ansari .................. G01S 15/931
(Continued)

Primary Examiner — Masud Ahmed
(74) Attorney, Agent, or Firm — Tran & Associates

(57) ABSTRACT

An Internet of Thing (IoT) device includes a body with a processor, a camera and a wireless transceiver coupled to the processor.

20 Claims, 16 Drawing Sheets

Related U.S. Application Data continuation of application No. 15/624,014, filed on Jun. 15, 2017, now Pat. No. 10,034,066, and a continuation-in-part of application No. 15/407,248, filed on Jan. 16, 2017, now Pat. No. 9,717,949.

(51) Int. Cl.

| | | |
|---|---|---|
| *A63B 71/14* | (2006.01) | |
| *A63B 69/36* | (2006.01) | |
| *A61B 5/11* | (2006.01) | |
| *A61B 5/00* | (2006.01) | |
| *G06F 3/00* | (2006.01) | |
| *G06K 9/00* | (2006.01) | |
| *G09B 19/00* | (2006.01) | |
| *G06F 1/16* | (2006.01) | |
| *B33Y 10/00* | (2015.01) | |
| *G01L 5/00* | (2006.01) | |
| *H04W 84/18* | (2009.01) | |
| *A63B 60/46* | (2015.01) | |
| *A63B 24/00* | (2006.01) | |
| *A63B 69/38* | (2006.01) | |
| *A42B 3/04* | (2006.01) | |
| *A63B 71/06* | (2006.01) | |
| *H04Q 9/00* | (2006.01) | |
| *G16H 30/20* | (2018.01) | |
| *A63B 43/00* | (2006.01) | |
| *G06F 3/01* | (2006.01) | |
| *H04N 5/225* | (2006.01) | |
| *H04N 7/18* | (2006.01) | |
| *A63F 13/211* | (2014.01) | |
| *A63F 11/00* | (2006.01) | |
| *G16H 20/30* | (2018.01) | |
| *G16H 40/63* | (2018.01) | |
| *G16H 40/67* | (2018.01) | |
| *G06K 19/02* | (2006.01) | |
| *G06K 19/077* | (2006.01) | |
| *G06Q 40/08* | (2012.01) | |
| *G16H 50/20* | (2018.01) | |
| *A63B 71/12* | (2006.01) | |
| *A63B 69/00* | (2006.01) | |
| *A63B 69/02* | (2006.01) | |
| *A63B 69/06* | (2006.01) | |
| *A63B 69/16* | (2006.01) | |
| *A63B 71/08* | (2006.01) | |
| *A63B 71/10* | (2006.01) | |
| *A63B 21/072* | (2006.01) | |
| *H04B 1/04* | (2006.01) | |
| *H04L 29/08* | (2006.01) | |
| *H04W 88/02* | (2009.01) | |
| *A61B 5/01* | (2006.01) | |
| *A61B 5/024* | (2006.01) | |
| *A61B 5/0402* | (2006.01) | |
| *A61B 5/053* | (2006.01) | |
| *A61B 5/055* | (2006.01) | |

(52) U.S. Cl.
CPC ....... *A63B 69/0026* (2013.01); *A63B 69/0028* (2013.01); *A63B 69/0048* (2013.01); *A63B 69/0071* (2013.01); *A63B 69/02* (2013.01); *A63B 69/06* (2013.01); *A63B 69/16* (2013.01); *A63B 69/3632* (2013.01); *A63B 71/085* (2013.01); *A63B 71/10* (2013.01); *A63B 71/1216* (2013.01); *A63B 71/1291* (2013.01); *A63B 71/141* (2013.01); *A63B 2071/125* (2013.01); *A63B 2071/1233* (2013.01); *A63B 2071/1283* (2013.01); *A63B 2207/02* (2013.01); *A63B 2208/0204* (2013.01); *A63B 2220/12* (2013.01); *A63B 2220/13* (2013.01); *A63B 2220/16* (2013.01); *A63B 2220/20* (2013.01); *A63B 2220/24* (2013.01); *A63B 2220/30* (2013.01); *A63B 2220/40* (2013.01); *A63B 2220/51* (2013.01); *A63B 2220/53* (2013.01); *A63B 2220/56* (2013.01); *A63B 2220/72* (2013.01); *A63B 2220/74* (2013.01); *A63B 2220/75* (2013.01); *A63B 2220/76* (2013.01); *A63B 2220/803* (2013.01); *A63B 2220/806* (2013.01); *A63B 2220/807* (2013.01); *A63B 2220/833* (2013.01); *A63B 2220/836* (2013.01); *A63B 2225/30* (2013.01); *A63B 2225/50* (2013.01); *A63B 2225/54* (2013.01); *A63B 2230/04* (2013.01); *A63B 2230/06* (2013.01); *A63B 2230/50* (2013.01); *A63B 2230/60* (2013.01); *A63B 2230/70* (2013.01); *A63B 2243/007* (2013.01); *A63B 2243/0025* (2013.01); *A63B 2243/0037* (2013.01); *A63B 2243/0054* (2013.01); *A63B 2243/0066* (2013.01); *A63B 2243/0095* (2013.01); *A63B 2244/102* (2013.01); *A63B 2244/18* (2013.01); *A63B 2244/19* (2013.01); *A63B 2244/20* (2013.01); *A63B 2244/203* (2013.01); *G16H 50/20* (2018.01); *H04B 1/04* (2013.01); *H04L 67/10* (2013.01); *H04Q 2209/40* (2013.01); *H04W 88/02* (2013.01)

(56) References Cited

U.S. PATENT DOCUMENTS

| | | | |
|---|---|---|---|
| 2016/0357188 A1* | 12/2016 | Ansari | ................ G05D 1/0212 |
| 2016/0357262 A1* | 12/2016 | Ansari | .................... G06F 3/017 |
| 2016/0358477 A1* | 12/2016 | Ansari | ................. G08G 1/167 |
| 2017/0109940 A1* | 4/2017 | Guo | ....................... G06T 19/20 |

\* cited by examiner

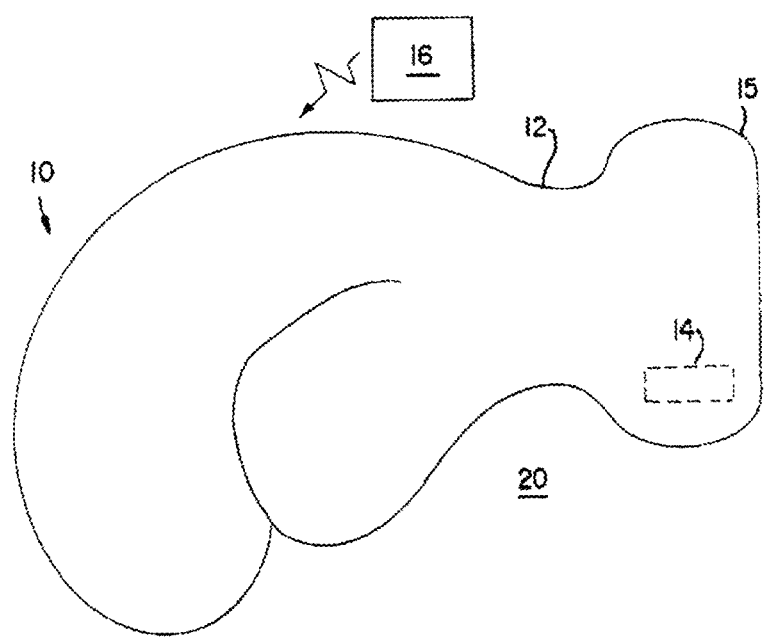
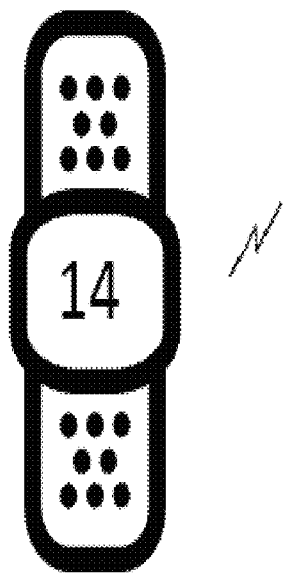
FIG. 7
FIG. 8

SMART DEVICE

BACKGROUND

The present invention relates to the Internet of Things (IoT).

SUMMARY

In one aspect, an Internet of Thing (IoT) device includes a processor coupled to a wireless transceiver; a camera; an accelerometer to detect acceleration of the device; and a module to follow a third-party motion or another device motion based on camera and accelerometer outputs.

These and other features of the present invention will become readily apparent upon further review of the following specification and drawings.

BRIEF DESCRIPTION OF THE DRAWINGS

FIG. 7 shows an exemplary glove, FIG. 8 shows an exemplary smart band.

FIG. 11A shows exemplary smart rackets while

FIG. 12A-12B show exemplary protective gears, while

FIG. 16A-16C shows exemplary coaching system for skiing, bicycling, and weightlifting/free style exercise, respectively, while

Similar reference characters denote corresponding features consistently throughout the attached drawings.

DETAILED DESCRIPTION OF THE PREFERRED EMBODIMENTS

According to various embodiments of the present disclosure, an electronic device may include communication functionality. For example, an electronic device may be a smart phone, a tablet Personal Computer (PC), a mobile phone, a video phone, an e-book reader, a desktop PC, a laptop PC, a netbook PC, a Personal Digital Assistant (PDA), a Portable Multimedia Player (PMP), an MP3 player, a mobile medical device, a camera, a wearable device (e.g., a Head-Mounted Device (HMD), electronic clothes, electronic braces, an electronic necklace, an electronic accessory, an electronic tattoo, or a smart watch), and/or the like.

According to various embodiments of the present disclosure, an electronic device may be a smart home appliance with communication functionality. A smart home appliance may be, for example, a television, a Digital Video Disk (DVD) player, an audio, a refrigerator, an air conditioner, a vacuum cleaner, an oven, a microwave oven, a washer, a dryer, an air purifier, a set-top box, a TV box (e.g., Samsung HomeSync™, Apple TV™, or Google TV™), a gaming console, an electronic dictionary, an electronic key, a camcorder, an electronic picture frame, and/or the like.

According to various embodiments of the present disclosure, an electronic device may be a medical device (e.g., Magnetic Resonance Angiography (MRA) device, a Magnetic Resonance Imaging (MRI) device, Computed Tomography (CT) device, an imaging device, or an ultrasonic device), a navigation device, a Global Positioning System (GPS) receiver, an Event Data Recorder (EDR), a Flight Data Recorder (FDR), an automotive infotainment device, a naval electronic device (e.g., naval navigation device, gyroscope, or compass), an avionic electronic device, a security device, an industrial or consumer robot, and/or the like.

According to various embodiments of the present disclosure, an electronic device may be furniture, part of a building/structure, an electronic board, electronic signature receiving device, a projector, various measuring devices (e.g., water, electricity, gas or electro-magnetic wave measuring devices), and/or the like that include communication functionality.

According to various embodiments of the present disclosure, an electronic device may be any combination of the foregoing devices. In addition, it will be apparent to one having ordinary skill in the art that an electronic device according to various embodiments of the present disclosure is not limited to the foregoing devices.

In one embodiment, a smart device includes sensor(s) and wireless communication therein. The device can detect tension and communicate to a computer for storage and analysis. The smart device provides an automatic electronic process that eliminates the need for a manual inspection process, and uses electronic detection of stress, eliminating subjective human judgments and producing greater uniformity in maintenance, inspection, and emergency detection procedures.

Figure 1A:
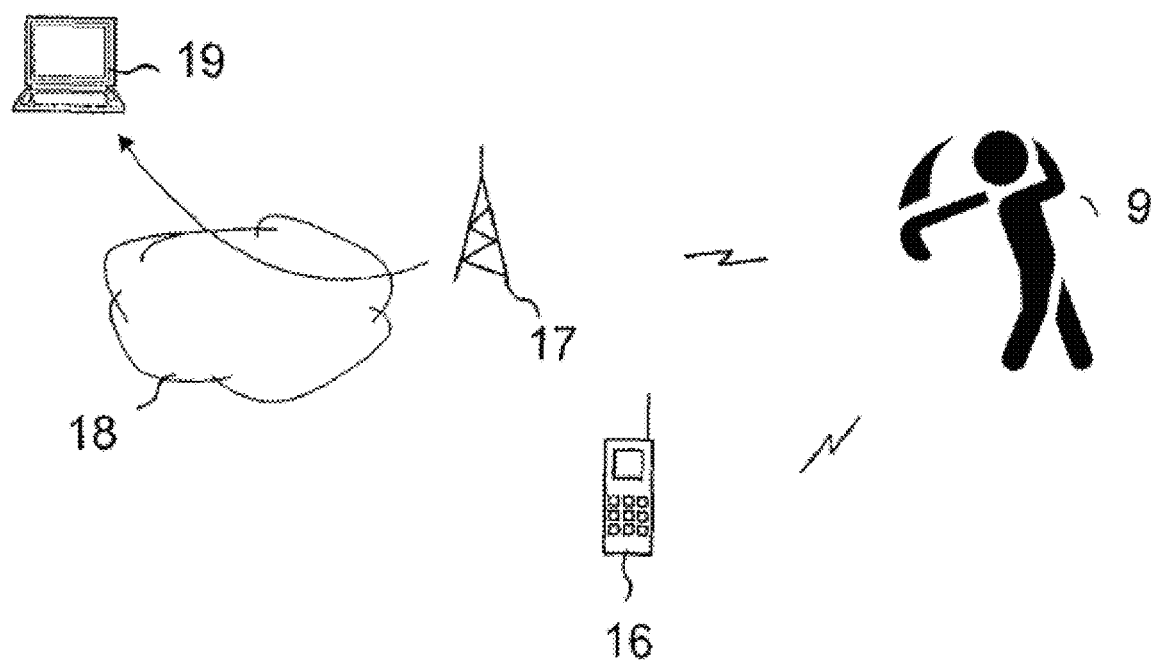
FIG. 1A illustrates an exemplary environment for communicating data from a monitoring device to external computers

FIG. 1A illustrates an exemplary environment for communicating data from a monitoring device to external computers. In FIG. 1A, the monitoring device used for a device 9 includes an interface with a radio transmitter for forwarding the result of the comparison to a remote device. In one example, the monitoring device may include an additional switch and user interface. The user interface may be used by the user in order to trigger transmission of the comparison of the hand or foot pattern reference data with the stroke patterns data to the remote device. Alternatively, the transmission may occur automatically each time the device has been used, or may be triggered by placing the device in a cradle or base. All parts of the monitoring device may be encapsulated with each other and/or may be integrated into or attached to the body of the device 9. Alternatively, a radio transmitter may be arranged separately from the other parts, for instance, in a battery charger, cradle or base of the device 9. In that example, the interface 7 may include contact terminals in the device 9, which are connected to the corresponding terminals in the battery charger for forwarding the result of the comparison via a wired connection to the transmitter in the battery charger or may be connected by induction or short range wireless communications. The radio transmitter in the battery charger then transmits this comparison result further via the wireless radio connection to the remote device. In FIG. 1A, the remote device may be a mobile phone 16, PDA or computer 19, which receives the information directly from the monitoring device via a short range radio connection, as one example of a transmitter, such as a Bluetooth or a Wifi or a Zigbee connection. In one example, the user of the remote device may receive information about how thoroughly the device 9 has been used or the need to provide a replacement device. FIG. 1A also illustrates an alternate example of a transmitter, using an intermediate receiver 17 and a network 18, such as a cellular radio system. Also in this example, the radio transmitter may be located in connection with the device 9 or alternatively in connection, with a charger, cradle or base station of the device 9. In such an example, the comparison result may be transmitted via an intermediate receiver 17 and the network 18 to a remote device 19, 16 located further away than the range of a short range radio system, for example. The remove device 19, 16 may be any device suitable for receiving the signals from the network 18 and providing feedback on an output device. The transmission of information via a cellular radio system to the remote device may allow an advertiser provide an advertisement. For example, an advertisement may be added to the comparison result using network elements in the cellular radio system. The user may receive an advertisement with the comparison result. An advantage with such a solution is that the advertiser may provide revenue offsetting all or a portion of the cost for the transmission of the comparison result from the device 9 to the remote device 19, 16.

Figure 1B:
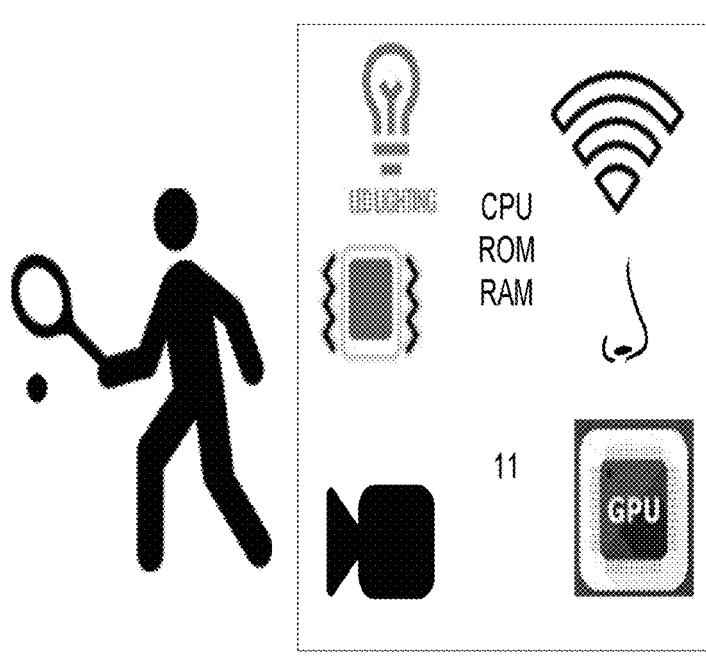
FIG. 1B is a perspective view of an exemplary IoT device system.

FIG. 1B shows a block diagram of the unit 9 with processor/RAM/ROM 11. The unit 9 includes a motion sensor, a multi-axis accelerometer, and a strain gage 42. The multi-axis accelerometer may be a two-axis or three-axis accelerometer. Strain gage 21 is mounted in the neck of the racket, and measures force applied to the ball, i.e., force in a z direction. Acceleration and force data are acquired by the microprocessor at a data acquisition rate (sampling rate) of from about 10 to 50 samples/second, e.g., about 20 samples/second. The acceleration data is used to infer motion, using an algorithm discussed below; it is not converted to position data. In this embodiment, because the sensors and strain gage are not in the head region, the head can be removable and replaceable, e.g., by threaded engagement with the handle (not shown), so that the device can continue to be used after instrument wear has occurred. Any desired type of removable head or cartridge can be used.

The unit 11 also includes a camera, which can be a 360 degree camera. Alternatively, the camera can be a 3D camera such as the Kinect camera or the Intel RealSense camera for ease of generating 3D models and for detecting distance of objects. To reduce image processing load, each camera has a high performance GPU to perform local processing, and the processed images, sound, and odor data are uploaded to a cloud storage for subsequent analysis.

The unit 11 includes an electronic nose to detect odor. The electronic nose can simply be a MEMS device acting as a particle counter. An embodiment of the electronic nose can be used that includes a fan module, a gas molecule sensor module, a control unit and an output unit. The fan module is used to pump air actively to the gas molecule sensor module. The gas molecule sensor module detects the air pumped into by the fan module. The gas molecule sensor module at least includes a gas molecule sensor which is covered with a compound. The compound is used to combine preset gas molecules. The control unit controls the fan module to suck air into the electronic nose device. Then the fan module transmits an air current to the gas molecule sensor module to generate a detected data. The output unit calculates the detected data to generate a calculation result and outputs an indicating signal to an operator or compatible host computer according to the calculation result.

An electronic tongue sensor can be provided to sense quality of sweat or liquid. The tongue includes a liquid molecule sensor module, a control unit and an output unit. Body liquid is applied or swiped on to the liquid molecule sensor module. The molecule sensor module detects the liquid molecules pumped into by the stirring module. The liquid molecule sensor module at least includes a molecule sensor which is covered with a compound. The compound is used to combine preset liquid molecules. The control unit controls the stirring module to pump liquid to be "tasted" into the electronic tongue device. Then the module transmits a flow current to the liquid molecule sensor module to generate a detected data. The output unit calculates the detected data to generate a calculation result and outputs an indicating signal to an operator or compatible host computer according to the calculation result. Such electronic tongue can detect quality of fog or liquid, among others.

In one embodiment for analyzing tooth structure, restorative materials within a tooth structure, and disease states of a tooth, the unit 11 includes a probe 20 which may be attached to a variety of probes, and instruments to afford adaptability to a variety of situations in providing diagnostic information on an object such as a naturally occurring structure, man-made materials placed or found within the structure, diseased or otherwise affected, infected or effected structure, as well as structure that has been eroded, worn by attrition, abraded, abfracted, fractured, crazed, broken or otherwise compromised through enthusiast use, misuse, fatigue or longevity of use. The probe 20 generates electrical outputs which are interpreted by a smart phone or computer.

In one embodiment, the probe 20 can be a vibratory transducer that sends out vibrations at known frequency and amplitude. The probe 20 also includes a receiver which can be an accelerometer, for example. The accelerometer is attached to the teeth and connected to a computer. The accelerometer digitizes the received vibrations and provides them into the phone or computer. The transducer can be a single piezoelectric transducer or an array with elements arranged to fit in a mouthpiece or an appliance to be worn over the oral arch. The transducer elements can be mounted in silicone rubber or other material suitable for damping mechanical coupling between the elements. Other materials may also be used for the array construction. For example, the transducer may be formed from one or more pieces of piezocomposite material, or any material that converts electrical energy to acoustic energy. The receiver can also be positioned to fit in the mouthpiece or appliance. One embodiment of the receiver is an accelerometer, but a suitable piezoelectric transducer can serve as the receiver as well.

The software in the computer compares these inputs to known vibration responses corresponding to striking states on a ball or object. The computer 30 displays a response on the computer screen for that user.

Figure 1C:
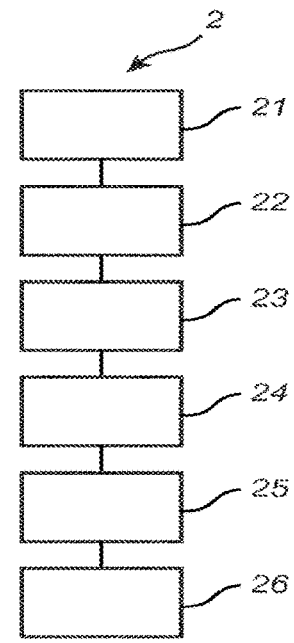
FIG. 1C is an exemplary process supported by the device according to the present invention.

FIG. 1C schematically shows a method or app 2 which may be implemented by the computing unit 11 shown in FIG. 1B. For example, the app 2 may be a computer implemented method. A computer program may be provided for executing the app 2. The app 2 includes code for:

(21) capture user motion with accelerometer or gyroscope

(22) capture VR views through camera and process using GPU

(23) capture user emotion using facial recognition or GSR

(24) model user action using kinematic model

(25) compare user action with idea action

(26) coach user on improvement to user techniques.

Figure 2A:
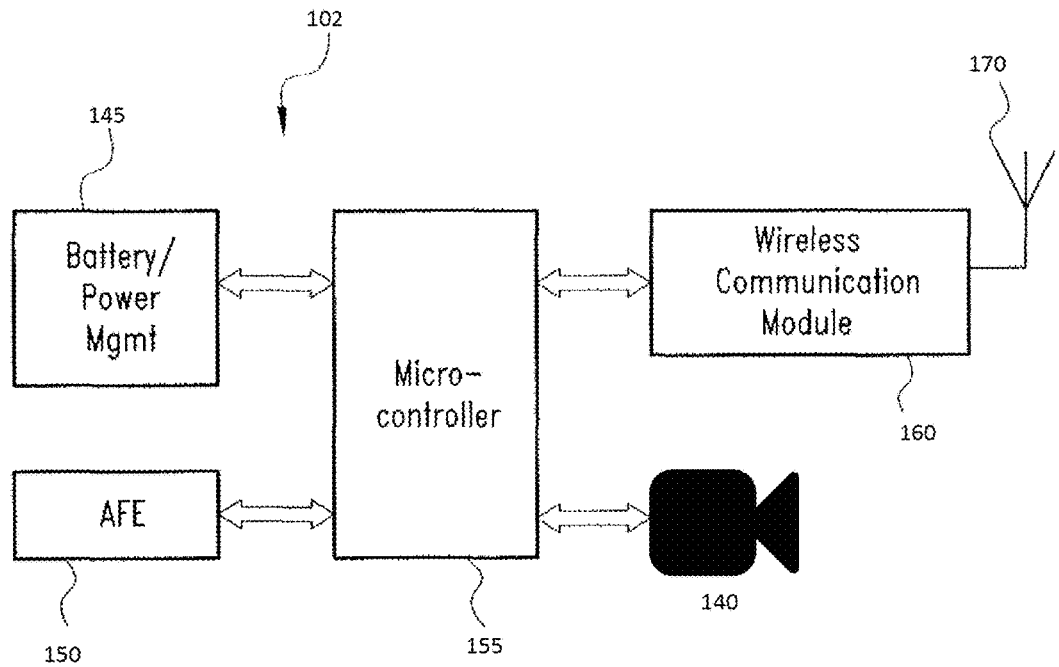
FIG. 2A is a block diagram of an electronic circuit for a smart device.

As shown in FIG. 2A, a microcontroller 155 receives and processes signals from the sensor 112-114, and converts those signals into an appropriate digital electronic format. The microcontroller 155 wirelessly transmits tension information in the appropriate digital electronic format, which may be encoded or encrypted for secure communications, corresponding to the sensed traffic and/or crime indication through a wireless communication module or transceiver 160 and antenna 170. Optionally, a camera 140 can be provided to visually detect traffic and/or crime and movement of the structure. While monitoring of the smart device 100 traffic and/or crime is continuous, transmission of tension information can be continuous, periodic or event-driven, such as when the tension enters into a warning or emergency level. Typically the indicated tension enters a warning level, then an emergency level as tension drops below the optimal range, but corresponding warning and emergency levels above the optimal range can also be used if supported by the smart device 100. The microcontroller 155 is programmed with the appropriate warning and emergency levels, as well as internal damage diagnostics and self-recovery features.

The tension information can take any form, including a simple warning/emergency indication that the tension is approaching or exceeding tension specifications, respectively. While under-tension is known to be the primary cause of structural or mechanical problems associated with devices, over-tension can also be a problem and can also be reported by the smart device 100.

The sensors can detect force, load, tension and compression forces on the device such as the device. Other data includes Acceleration; Velocity; Global absolute displacement; Local relative displacement; Rotation; Strain; Stress; Force; and Static-position video. Wind speed/direction; External temperature; weather parameters (rainfall, humidity, solar radiation, etc.); Internal or structural temperature; Mass loading (occupant count, etc.); Static tilt; Fatigue damage; Corrosion; Acoustic emission; and Moving-position video. A force is simply a push or pull to an object and can be detected by a load cell, pressure cell or strain sensor. A Load: Is simply a force applied to a structure. Ex: weight of vehicles or pedestrians, weight of wind pushing on sides. Tension & Compression are internal forces that make a member longer or shorter. Tension stretches a member and Compression pushes the member closer together. Acceleration can also be detected by Force-Balance (Servo) Piezoelectric Piezoresistive MEMS. Velocity can be measured by force-balance (servo) MEMS, or Mechanical Doppler Heated wire. A local Displacement sensor can be LVDT/Cable potentiometer Acoustic Optical/laser Temperature Electrical Optical fiber. A rotation sensor can be Gyro MEMS Gyro Tilt Electro-mechanical MEMS. A strain sensor can be a resistance gauge Vibrating wire Optical fiber Corrosion Electrical Chemical sensors. A traffic and/or crime sensor can be a microphone listening to acoustic emission, or Piezoelectric MEMS, for example, and sonar sound processing can be used to detect where crime activity is coming from.

The sensor 112-114, transceiver 160/antenna 170, and microcontroller 155 are powered by and suitable power source, which may optionally include an electromagnetic field (EMF) scavenging device 145, such as those known in the art, that convert ambient EMF (such as that emitted by radio station broadcasts) into small amounts of electrical power. The EMF scavenging device 145 includes a battery to buffer and store energy for the microcontroller 155, sensor 112-114, camera 140 and wireless communications 160/170, among others.

The circuit of FIG. 2A contains an analog front-end ("AFE") transducer 150 for interfacing signals from the sensor 112-114 to the microcontroller 155. The AFE 150 electrically conditions the signals coming from the sensor 112-114 prior to their conversion by the microcontroller 155 so that the signals are electrically compatible with the specified input ranges of the microcontroller 155. The microcontroller 155 can have a CPU, memory and peripheral circuitry. The microcontroller 155 is electrically coupled to a wireless communication module 160 using either a standard or proprietary communication standard. Alternatively, the microcontroller 155 can include internally any or all circuitry of the smart device 100, including the wireless communication module 160. The microcontroller 155 preferably includes power savings or power management circuitry 145 and modes to reduce power consumption significantly when the microcontroller 155 is not active or is less active. The microcontroller 155 may contain at least one Analog-to-Digital Converter (ADC) channel for interfacing to the AFE 150.

The battery/power management module 145 preferably includes the electromagnetic field (EMF) scavenging device, but can alternatively run off of previously stored electrical power from the battery alone. The battery/power management module 145 powers all the circuitry in the smart device 100, including the camera 140, AFE 150, microcontroller 155, wireless communication module 160, and antenna 170. Even though the smart device 100 is preferably powered by continuously harvesting RF energy, it is beneficial to minimize power consumption. To minimize power consumption, the various tasks performed by the circuit should be repeated no more often than necessary under the circumstances.

Stress information from the smart device 100 and other information from the microcontroller 155 is preferably transmitted wirelessly through a wireless communication module 160 and antenna 170. As stated above, the wireless communication component can use standard or proprietary communication protocols. Smart lids 100 can also communicate with each other to relay information about the current status of the structure or machine and the smart device 100 themselves. In each smart device 100, the transmission of this information may be scheduled to be transmitted periodically. The smart lid 100 has a data storage medium (memory) to store data and internal status information, such as power levels, while the communication component is in an OFF state between transmission periods. On the other hand, once the communication commences in the ON state, the microcontroller 155 can execute the following tasks:

1. Neighbor discovery: in this task each smart device 100 sends a beacon identifying its location, capabilities (e.g. residual energy), status. 2. Cluster formation: cluster head will be elected based on the findings in (1). The cluster children communicate directly with their cluster head (CH). 3. Route discovery: this task interconnects the elected cluster heads together and finds the route towards the sink smart device (node) so that minimum energy is consumed. 4. Data transmission: the microcontroller processes the collected color data and based on the adopted data dissemination approach, the smart device 100 will do one of the following. (a) Transmit the data as is without considering the previous status; or (b) transmit the data considering the previous status. Here we can have several scenarios, which include: (i) transmitting the data if the change in reported tension exceeds the warning or emergency levels; and (ii) otherwise, do not transmit.

Figure 2B:
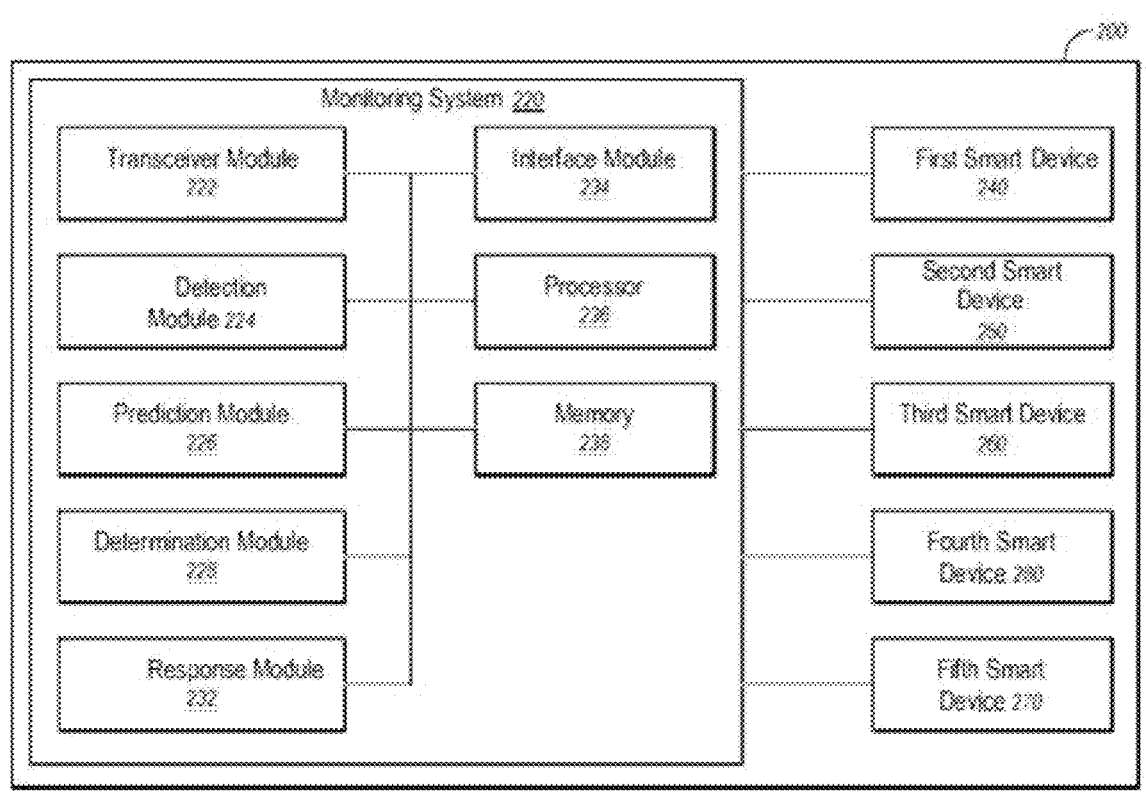
FIG. 2B is a block diagram of a big data system for predicting stress experienced by a structural unit such as a bridge, a building, or a plane, for example.

The electronic of FIG. 2A operates with a big data discovery system of FIG. 2B that determines events that may lead to failure. FIG. 2B is a block diagram of an example stress monitoring system 200 that may be process the stress detected by the smart device 100 of FIG. 1, arranged in accordance with at least some embodiments described herein. Along with the stress monitoring system 220, a first smart device such as a smart device 240, a second smart device 250, a third smart device 260, a fourth smart device 280, and additional sensors 270 may also be associated with the unit 200. The stress monitoring system 220 may include, but is not limited to, a transceiver module 222, a stress detection module 224, a stress prediction module 226, a determination module 228, a stress response module 232, an interface module 234, a processor 236, and a memory 238.

The transceiver module 222 may be configured to receive a stress report from each of the first, second, and third smart devices 240, 250, 260. In some embodiments, the transceiver module 222 may be configured to receive the stress reports over a wireless network. For example, the transceiver module 222 and the first, second, and third smart devices 240, 250, 260 may be connected over a wireless network using the IEEE 802.11 or IEEE 802.15 standards, for example, among potentially other standards. Alternately or additionally, the transceiver module 222 and the first, second, and third smart devices 240, 250, 260 may communicate by sending communications over conductors used to carry electricity to the first, second, and third smart devices 240, 250, 260 and to other electrical devices in the unit 200. The transceiver module 222 may send the stress reports from the first, second, and third smart devices 240, 250, 260 to the prediction module 226, the stress detection module 224, and/or the determination module 228.

The stress module 224 may be configured to detect stress on the object as detected by the devices 100. The signal sent by the devices 100 collectively may indicate the amount of stress being generated and/or a prediction of the amount of stress that will be generated. The stress detection module 224 may further be configured to detect a change in stress of non-smart devices associated with the unit 200.

The prediction module 226 may be configured to predict future stress based on past stress history as detected, environmental conditions, forecasted stress loads, among other factors. In some embodiments, the prediction module 226 may predict future stress by building models of usage and weight being transported. For example, the prediction module 226 may build models using machine learning based on support vector machines, artificial neural networks, or using other types of machine learning. For example, stress may correlate with the load carried by a bridge or an airplane structure. In other example, stress may correlate with temperature cycling when a structure is exposed to constant changes (such as that of an airplane).

The prediction module 226 may gather data for building the model to predict stress from multiple sources. Some of these sources may include, the first, second, and third smart devices 240, 250, 260; the stress detection module 224; networks, such as the World Wide Web; the interface module 234; among other sources. For example, the first, second, and third smart devices 240, 250, 260 may send information regarding human interactions with the first, second, and third smart devices 240, 250, 260. The human interactions with the first, second, and third smart devices 240, 250, 260 may indicate a pattern of usage for the first, second, and third smart devices 240, 250, 260 and/or other human behavior with respect to stress in the unit 200.

In some embodiments, the first, second, and third smart devices 240, 250, 260 may perform predictions for their own stress based on history and send their predicted stress in reports to the transceiver module 222. The prediction module 226 may use the stress reports along with the data of human interactions to predict stress for the system 200. Alternately or additionally, the prediction module 226 may make predictions of stress for the first, second, and third smart devices 240, 250, 260 based on data of human interactions and passed to the transceiver module 222 from the first, second, and third smart devices 240, 250, 260. A discussion of predicting stress for the first, second, and third smart devices 240, 250, 260 is provided below with respect to FIGS. 5 and 6.

The prediction module 224 may predict the stress for different amounts of time. For example, the prediction module 224 may predict stress of the system 200 for 1 hour, 2 hours, 12 hours, 1 day, or some other period. The prediction module 224 may also update a prediction at a set interval or when new data is available that changes the prediction. The prediction module 224 may send the predicted stress of the system 200 to the determination module 228. In some embodiments, the predicted stress of the system 200 may contain the entire stress of the system 200 and may incorporate or be based on stress reports from the first, second, and third smart devices 240, 250, 260. In other embodiments, the predicted stress of the system 200 may not incorporate or be based on the stress reports from the first, second, and third smart devices 240, 250, 260.

The determination module 228 may be configured to generate a unit stress report for the system 200. The determination module 228 may use the current stress of the system 200, the predicted stress of the system 200 received from the prediction module 224; stress reports from the first, second, and/or third smart devices 240, 250, 260, whether incorporated in the predicted stress of the system 200 or separate from the predicted stress of the system 200; and an amount of stress generated or the predicted amount of stress, to generate a unit stress report.

In some embodiments, one or more of the stress reports from the first, second, and/or third smart device 240, 250, 260 may contain an indication of the current operational profile and not stress. In these and other embodiments, the determination module 228 may be configured to determine the stress of a smart device for which the stress report indicates the current operational profile but not the stress. The determination module 228 may include the determined amount of stress for the smart device in the unit stress report. For example, both the first and second smart device 240, 250 may send stress report. The stress report from the first smart device 240 may indicate stress of the first smart device 240. The stress report from the second smart device 250 may indicate the current operational profile but not the stress of the second smart device 250. Based on the current operational profile of the second smart device 250, the determination module 228 may calculate the stress of the second smart device 250. The determination module 228 may then generate a unit stress report that contains the stress of both the first and second smart devices 240, 250.

In some embodiments, the stress monitoring system 220 may not include the prediction module 226. In these and other embodiments, the determination module 228 may use stress reports from the first, second, and/or third smart devices 240, 250, 260, with the received amount of stress inferred on non-smart devices, if any, to generate the unit stress report. The determination module 228 may send the unit stress report to the transceiver module 222.

In some embodiments, the processor 236 may be configured to execute computer instructions that cause the stress monitoring system 220 to perform the functions and operations described herein. The computer instructions may be loaded into the memory 238 for execution by the processor 236 and/or data generated, received, or operated on during performance of the functions and operations described herein may be at least temporarily stored in the memory 238.

Although the stress monitoring system 220 illustrates various discrete components, such as the prediction module 226 and the determination module 228, various components may be divided into additional components, combined into fewer components, or eliminated, depending on the desired implementation. In some embodiments, the unit 200 may be associated with more or less smart devices than the three smart devices 240, 250, 260 illustrated in FIG. 2.

Figure 3:
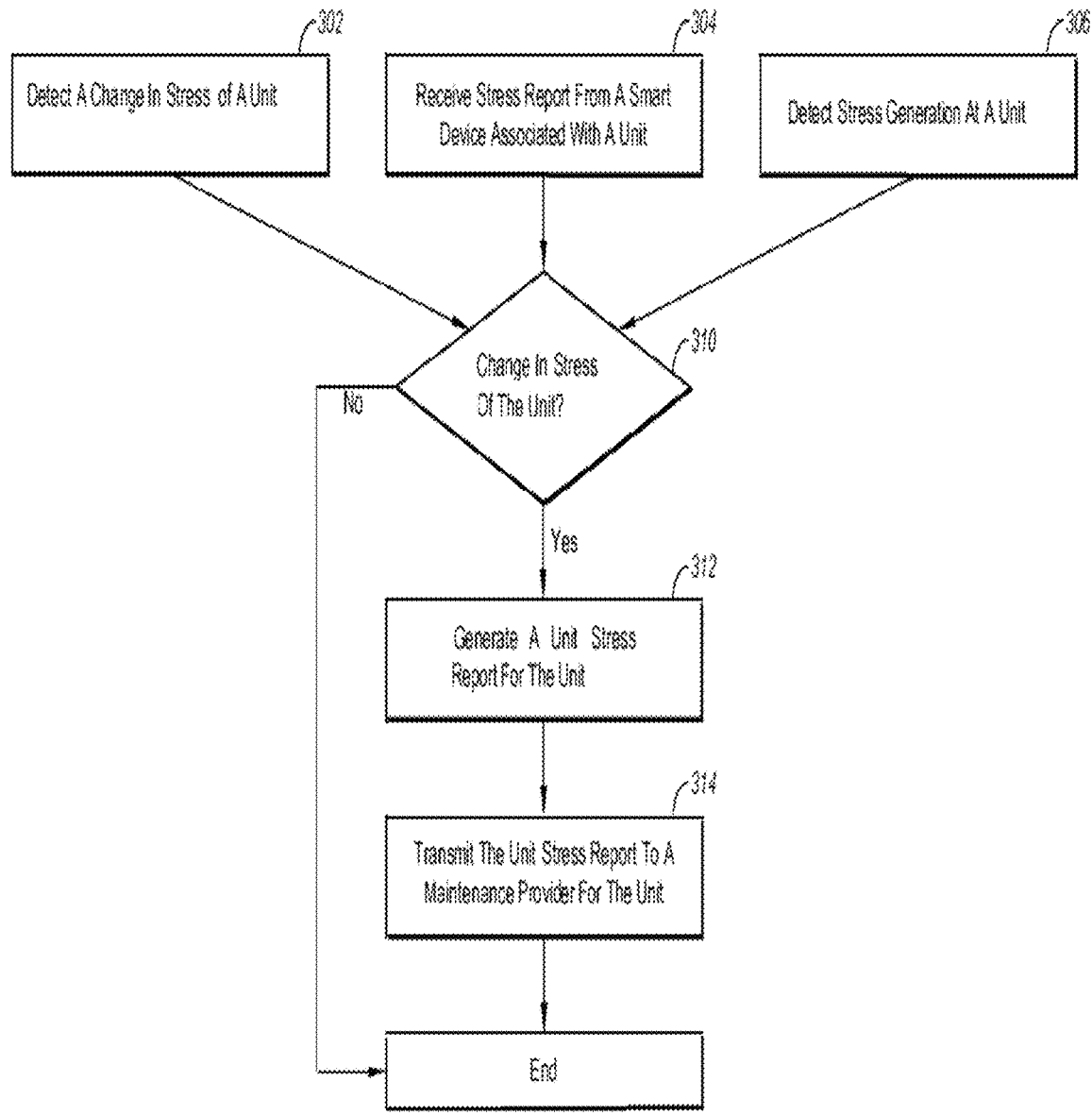
FIG. 3 is a flowchart illustrating one operation of the system of FIG. 2A-2B in detecting stress on a unit.

FIG. 3 is a flow chart of an example method 300 of monitoring stress of a or game unit, arranged in accordance with at least some embodiments described herein. The method 300 may be implemented, in some embodiments, by an stress monitoring system, such as the stress monitoring system 220 of FIG. 2. For instance, the processor 236 of FIG. 2B may be configured to execute computer instructions to perform operations for monitoring stress as represented by one or more of blocks 302, 304, 306, 310, 312, and/or 314 of the method 300. Although illustrated as discrete blocks, various blocks may be divided into additional blocks, combined into fewer blocks, or eliminated, depending on the desired implementation.

The method 300 may begin at one or more of blocks 302, 304, and/or 306. The blocks 302, 304, and/or 306 may occur at the same time or at different times and may or may not depend on one another. Furthermore, one or more of the block 302, 304, 306 may occur during the method 300. For example, the method 300 may complete when blocks 304, 310, and 312 occurs and without the occurrence of block 302 and 306.

In block 302, a change in stress of a device (device or beam) associated with a unit may be detected. A non-smart device may by any device that receives stress and does not generate an stress report indicating its stress, for example a legacy racket without IoT electronics. A change in the stress of a non-smart device may be detected using an stress detection module and/or usage meter associated with the unit, such as the stress detection module 224 and/or the smart device 100. For example, non-smart device stress can be estimated by the load the unit carries, the temperature cycling experienced by the unit, for example.

After a change in stress of the non-smart device is detected, the method 300 proceeds to block 310. In block 304, an stress report from a smart device such as the smart device 100 associated with the unit may be received. A smart device may be a device that detects stress and generates and transmits an stress report indicating the stress on the smart device. The stress report may indicate predicted future stress of the smart device. In some embodiments, an stress report may be received at set intervals from the smart device regardless of a change in the stress report. Alternately or additionally, a stress report may be received after a change in the stress of the smart device results in a change to the stress report. After a stress report is received from the smart device, the method 300 proceeds to block 310.

In block 306, stress experienced at the unit may be detected. Stress at the unit may be detected using a stress detection module, such as the stress detection module 224 of FIG. 2B. After detecting stress at the unit, the method proceeds to block 310. At block 310, it is determined if a change in the stress occurred. For example, if an increase in stress occurs at the same time and at the same amount as an increase in the stress of a non-smart device, a change in the stress may not occur. If a change in the stress occurs, the method 300 proceeds to block 312. If no change occurs, the method 300 ends.

At block 312, a unit stress report is generated for the unit. In some embodiments, the unit stress report may indicate the current stress of the unit. Alternately or additionally, the unit stress report may indicate a current and predicted future stress of the unit. At block 314, the unit stress report is transmitted to a maintenance provider. In some embodiments, the unit stress report may be transmitted when the unit stress report indicates a change in stress for the unit that is greater than a predetermined threshold. If the unit stress report indicates a change in stress for the unit that is less than the predetermined threshold, the unit stress report may not be transmitted to the provider of maintenance services.

Figure 5:
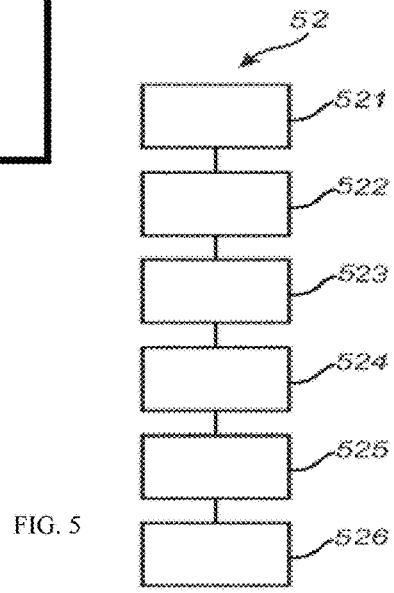
FIG. 5 shows an exemplary process for augmented and/or virtual reality for viewers participating in a game.

FIG. 5 shows in more details the computer 30 and the interface to the probe 20. An amplifier 90 amplifies vibratory output from a transducer 92. A pick up unit having an accelerometer (or an array) 96 receives reflected vibrations from user arm or leg 94, among others. A computer 98 includes a digital converter to digitize output from the pick-up unit and software on the computer 98 can process the captured diagnostic data. Diagnostic software 100 can include a database of known restorations, diseases, and tissue conditions whose signatures can be matched against the capture diagnostic data, and the result can be displayed on a screen for review by the athlete.

Included in one embodiment of the instrumentation is the transmitter or transducer, which will emit the vibrations that will be imparted to the teeth and jaws. This will be connected to a power supply and amplifier, which will allow for a frequency range. On electrical excitation, the transducer emits an outgoing vibration. That vibration will then travel into the arm or leg and down is root into the soft tissues and out into the bones or jaws. The accelerometer or detector will be placed on the bone of interest. It will receive the vibrations from the emitter. The effect of the vibrations on the muscle of interest will generate a pattern of frequency vibrations. Those vibrations will be digitally converted and analyzed against known dental states in the software of the computer. As the data is collected various linear samplings and comparisons will be made against the database. Software will make these comparisons as the data is received from the teeth.

FIG. 5 schematically shows a method or app 52 to perform collaborative VR/AR gaming. The app 52 includes code for:

(51) capture 360 degree view of the live event

(52) detect head position of the viewer

(53) adjust viewing angle on screen based on head position and user posture

(54) render view to simulate action based on user control rather than what the professional is doing

(55) augment view with a simulated object that is powered by viewer action as detected by sensors on viewer body

(56) compare professional result with simulated result and show result to a crowd of enthusiasts for social discussion.

Figure 4:
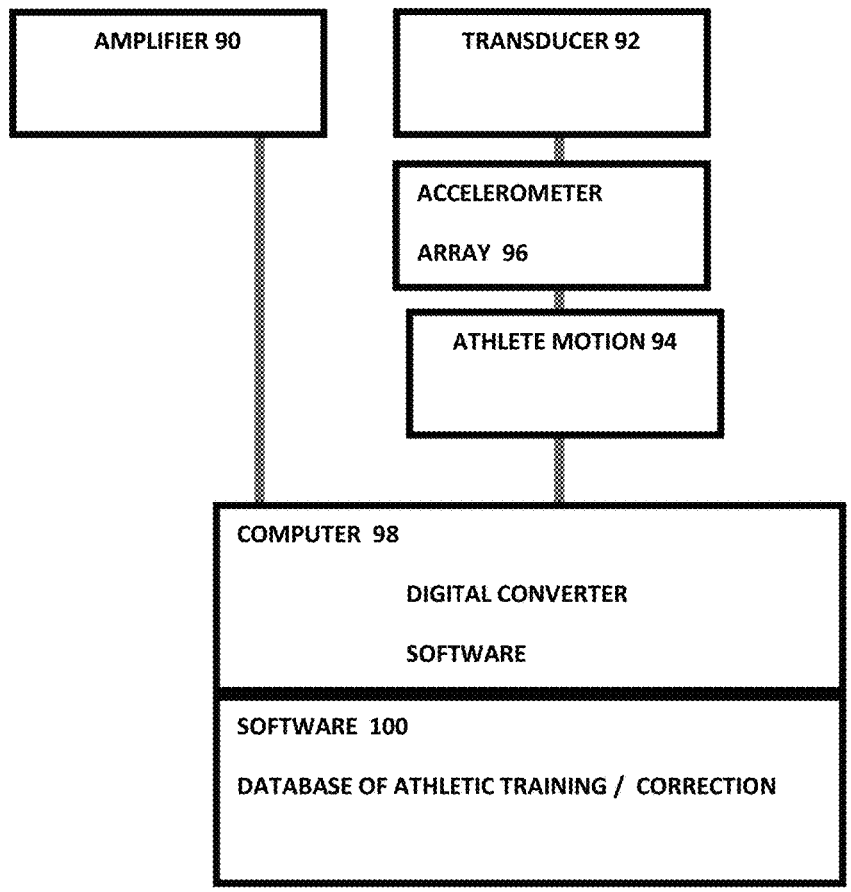
FIG. 4 shows an exemplary sports diagnosis and trainer system for augmented and/or virtual reality.
Figure 6:
FIG. 6 shows an exemplary process to identify reasons for sensor data changes using a gaming process.

FIG. 6 is a flowchart of a method of an embodiment of the present disclosure. Referring to FIG. 6, a smart system may collect from smart devices state change events of a smart system in operation 601. That is, the smart system of FIG. 4 collects information on each of the group of devices, the smart devices, the smart appliances, the security devices, the lighting devices, the energy devices, and the like. The state change events indicate when there is a change in the state of the device or the surrounding environment. The state change events are stored by the smart system. In operation 603, the system may determine whether a series of the collected state change events are a known pattern. That is, the gateway determines whether there are events which have been correlated or identified in the past. If the collected state change events have been identified in the past, it may be necessary to determine that the smart systems trusts the identification the collected state change events. The trust factor of the identification of the collected state change events may be determined by the number of users who have identified the collected state change events or the number of time collected state change events have been repeated and identified. In operation 605, when the series of the collected state change events is an unknown pattern, request users of the smart system to identify what caused the collected state change events request. That is, the system transmits to a gamification application (hereinafter app) on the user's mobile device a request to identify the collected state change events. The gamification app displays the information and request the user enter information identifying the collected state change events. Each of the mobile devices transmits this information back to the system to the gamification module. In operation 605, the system transmits the each user's identified collected state change events to the other user's of the smart home system and they each vote on the best identification of the collected state change events. Thus, the identified collected change state events that have been repeatedly identified over a period of weeks increases, the trustworthiness of the identification increases. Likewise, if every user of the smart system makes the same identification of the collected change state events, the identified collected change state events may be considered trustworthy at point. Such a determination of a threshold for when the identified collected change state events are considered trustworthy and therefore need not be repeated, is made by a system administrator. However, it will be understood that such a trustworthiness of this type only gives higher confidence of this particular dataset at that point in time. As such further repetition is required, since the sensor data may have noise, the more datasets to be identified to the pattern, the more robust the trustworthiness will be. Until the robustness reaches a threshold, then the system can confirm this is a known trustworthy pattern.

The system can use gaming to help enthusiasts improve dental care or maintain teeth hygiene. This may involve use of virtual tools, corresponding to such tools used in normal dental hygiene: device, tooth picks, dental floss, gum massaging aids, etc. In this embodiment, the game may, for example, have the object of fighting tooth or gum decay, damage or infection which may be caused by carries or other infectious agents. The user is presented with a library of tools and has to select a tool to treat a certain developing virtual condition, e.g. carries or a gum infection. The game rules determine a certain continuous progress of infection which if not properly "treated" by the user will cause decay of one or more teeth, gum infection, potential bleeding, loss of teeth, etc. In step 13, the user may score points depending on his ability to choose the right tools to treat a particular condition or in avoiding a condition from developing. Next, it is determined whether the condition of the teeth is satisfactory. If yes, the process terminates. If no, then the user is prompted whether he wishes to select another tool. If no, the process terminates. If yes, the process restarts. Here again, the game, in addition to being amusing and providing an insight of the user into his own teeth, may be educational, particularly for children, on teeth oral hygiene methods and on the importance of maintaining oral hygiene.

In accordance with another embodiment of the invention the game may involve use of a variety of virtual imaginary tools such as virtual guns, wands, etc. in order to fight infectious agents of the teeth or gums.

Smart Glove

FIG. 7 shows an exemplary glove which can be thin to provide touch sensitivity or thick to provide shock protection for boxers. A body 12 of the boxing glove 10 includes an impact measuring device 14 is embedded within the glove 12 in an area protected from direct impact. Such an area includes the cuff 15 of the glove 12 or that portion of the glove 12 adjacent a user's palm, or adjacent an inside surface of a user's fingers. Placement of the impact measuring device 14 into the lining of the glove in such an area allows for the force of a blow to be measured without presenting a hazard to the recipient of the blow. Under the embodiment, an impact measuring device 14 would be included in the right glove 12 for a right handed fighter, or the left glove 12 for a left handed fighter. For fighters that are equally effective with both hands, or to improve monitoring accuracy, an impact measuring device 14 would be included in both gloves 12. The impact measuring system 20. The impact measuring system 20 includes an impact measuring device 14 and impact display unit 16. The impact measuring device 14 is linked to the impact display 28 via a radio frequency (rf) link 32. Under the embodiment, the impact measuring device 14 includes at least one 3-axis accelerometer. A thin version of the glove can be worn to detect a golf stroke or a tennis stroke with legacy clubs or rackets that lacks IoT intelligence.

1. A glove comprising:
a glove body;
a processor in the glove body and coupled to a wireless transceiver;
a camera coupled to the glove body;
a sensor disposed in the glove body; and
an accelerometer disposed within the glove body to detect acceleration of the glove.

2. The glove of claim 1, at least one sensor selected from a sensor set comprising: a pressure sensor configured to detect at least one pressure event at a glove body external surface location; a glove motion sensor configured to detect at least one motion event of the glove; a digit motion sensor configured to detect at least one motion event of at least one digit of the user; a temperature sensor configured to detect a temperature at a glove body external surface location; and a contact sensor configured to detect a contact event of the glove with a contact object.

3. The glove of claim 1, the sensor comprising at least one of the same as the second sensor or different than the second sensor, the hand exercise event at least one of the same as the second hand exercise event or different than the second hand exercise event.

4. The glove of claim 1, the hand exercise regimen selected from a hand exercise regimen set comprising at least one of: a physical therapy hand exercise regimen; a physical training hand exercise regimen; or a physical performance hand exercise regimen.

5. The glove of claim 1, the glove comprising a gesture identifying component configured to identify at least one hand gesture detected by at least one sensor; the memory configured to, upon receiving an indication of a hand gesture identified by the gesture identifying component, store data corresponding to the hand gesture in the memory; and the device interface configured to, upon connecting to the device, provide at least some of the stored data corresponding to the hand gesture to the device.

6. The glove of claim 1, the glove comprising a plurality of finger receptacles, each having a sensor.

7. The glove of claim 1, comprising a sensor worn by an opponent in wireless communication with the processor to communicate the force of an impact from the glove.

8. A system for measuring a force of impact of a boxing glove of a boxer comprising:
an accelerometer disposed in the boxing glove of the boxer for measuring the force of impact of the boxing glove on an opponent;
a radio frequency transmitter disposed in the boxing glove and coupled to the accelerometer for transmitting impact measurements;
a radio frequency receiver for receiving the impact measurements; and
a display coupled to the radio frequency receiver for displaying the measured impacts.

Smart Band

FIG. 8 shows an exemplary stick on wearable monitoring device for sports and fitness applications. The wireless sensor electronics 14 is mounted on a band-aid in the example of FIG. 8. The band-aid can be removed upon completion of the sports event. The central patch can be recycled, and the adhesive portion can be disposed. While the embodiment is shown as a band-aid, the inventors contemplate that any suitable bands, straps, attachments can be used in lieu of the band-aid to attach the sensors to the body. For example, in Virtual Reality (VR) sports applications, sensors including gyroscopes and cameras can be positioned on various body portions to capture motion as well as eye tracking, mouth tracking, speech recognition, among others.

One embodiment uses Samsung's Bio-Processor which is an all-in-one health solution chip. By integrating not only Analog Front Ends (AFE), but also microcontroller unit (MCU), power management integrated circuit (PMIC), digital signal processor (DSP), and eFlash memory, it is able to process the bio-signals it measures without the need of external processing parts. Even with its integrated design, the Bio-Processor is particularly innovative thanks to its incredibly small size. When compared to the total area of the discrete parts, the Bio-Processor is only about one fourth of the total combined size, which is ideal for small wearable devices, offering a bounty of options when designing new devices. The Bio-Processor has five AFEs including bio-electrical impedance analysis (BIA), photoplethysmogram (PPG), electrocardiogram (ECG), skin temperature, and galvanic skin response (GSR) into a single chip solution that measures body fat, and skeletal muscle mass, heart rate, heart rhythm, skin temperature and stress level, respectively.

One embodiment provides a flexible and stretchable electronic patch that monitors impact or other events whereby a flexible substrate is geometrically patterned to allow the substrate to undergo substantial stretching and flexing while large regions of the substrate material experiences local strains much lower than the macroscopic applied strain. The geometric patterning of the substrate facilitates continuous low strain domains (LSDs) throughout the substrate—where low strain domains are defined as regions that experience strain levels (magnitude) lower than the macroscopic applied strain. Conventional electronic components can be mounted to the LSDs, and conventional metal traces can be routed through the LSDs, dramatically reducing the stresses transmitted to the components and traces by the substrate during stretching and flexing, and therefore reducing the potential for component debonding, trace cracking, and circuit failure. The geometrically patterned strain relief features (SRFs) are dispersed either regularly or irregularly throughout the substrate. The geometrically patterned SRF regions form "hinge-like" domains. During macroscopic deformation, the SRFs rotate, translate, open, close, or otherwise change shape, causing the "hinge-like" regions to deform, and the remaining larger LSD substrate regions to primarily rotate and translate. The SRFs are designed such that the "hinge-like" regions also exhibit relatively small strain compared to the macroscopic applied strain and thus enable conductive traces, such as copper or gold, to run through the hinges and maintain function during stretching, flexing and twisting of the patch. The substrate can be multilayered to enable running conductive traces, ground layers, vias, and/or components on/in multiple layers through the thickness of the overall substrate. The geometric patterning can be designed to enable different stretching, flexing and twisting, providing uniaxial, biaxial, and multi-axial stretchability or flexibility, and the ability to conform to a variety of surface curvatures. The geometrically patterned substrate offers a means of packaging complex multi-layered electronics designs for monitoring impact (and other) events onto a stretchable and flexible substrate enabling the device to dynamically stretch, bend, twist, and conform to arbitrary shapes. The stretchable, flexible geometrically structure electronics can be fabricated using the same technologies for conventional flexible circuit boards where the stretch-enabling patterning can be imparted at different stages in the fabrication process and can also be fabricated using emerging materials and fabrication methods. The Stretchable bandaid has the stretchable, flexible substrate described above with multiple LSDs for placement of electronic components (e.g., accelerometers, gyroscopes, pressure temperature, gas and fluid sensors, microprocessors, transceivers, GPS, clocks, actuators, vias, and batteries (or other energy source)) and multiple patterned hinge-like regions bridging the LSDs which enable the routing of conducting interconnecting traces. The SEHIM patch can take the form factor of a bandaid or bandage or other such wearable form factor. The geometric patterning provides stretch, flex and twist to conform to a body and stretch, flex and twist to move or deform with a body. The bandaid detects impact accelerations, using a 3-axis accelerometer and processes the raw acceleration data in the microprocessor. The processed data is stored in the microprocessor and later (or potentially in real time) transmitted via the Bluetooth to a smart phone, tablet or computer. This embodiment encompasses wireless communication but wired communication may be desirable in some applications and can be accommodated by this invention. The bandaid can be stretched, bent and twisted with the traces and components at low strains to maintain electrical function. In all cases there was effectively no strain on the components and solder joints. The bandaid can also possess an adhesive backing for direct adhesion to the head, body or object. The band can also be coated to provide both added comfort and protection against moisture, water, and other environmental factors. The band can also contain other sensors including gyroscopes, temperature and pressure sensors, moisture sensors, clocks, chemical and/or biological sensors, etc. Features of the smart band can include:

1. A smart patch, comprising:
   a band to be placed over a body portion;
   a processor in the band and coupled to a wireless transceiver;
   a camera coupled to the band;
   a sensor disposed in the band; and
   an accelerometer disposed within the band to detect acceleration of the band.

2. The patch of claim 1, comprising a plurality of smart patches forming a mesh network and communicating episodically to conserve power.

3. The patch of claim 1 where the electronic components, sensors, and interconnects of the patch monitor, record, process and/or transmit events of interest (such as accelerometers and gyroscopes for impact events, temperature sensors for temperature and/or temperature gradients, pressure sensors, moisture sensors, chemical sensors).

4. The patch of claim 1 comprised for sensing and/or monitoring impact events where the sensors are accelerometers, gyroscopes, and/or pressure sensors.

5. The patch of claim 1 comprised for sensing and/or monitoring and/or controlling ongoing events where the sensors monitor temperature, temperature gradients, motion, position, environmental or chemical levels, or other such information.

6. The patch of claim 1 comprised for sensing events or other information including mounting multiple distributed sensors for obtaining spatial and/or temporal distribution in the data and/or multiple sensors sensing different information and data.

7. The patch of claim 1 including wired or wireless communication, such as a Bluetooth module or a wi-fi module or other transmission module, transmitting and/or receiving information to/from another device.

8. The patch of claim 1 with power and energy sources including batteries, wired or wireless rechargeable batteries, photovoltaics, thermoelectrics, or energy harvesters.

9. The patch of claim 1 with an adhesive backing for directly adhering to a head, a body, or an object.

10. The patch of claim 1 contained in an adhesive or a sleeve for adhering or attaching to a head, a body, or an object.

11. The patch of claim 1 coated with a coating for protection against the elements (water, moisture, dirt, other) and/or for increased comfort to the wearer.

12. The patch of claim 1, comprising a geometrically patterned substrate that contains regions of low strain domains (LSDs) bridged by hingeable strain relief features (SRFs) which also contain low strain regions and enable the stretching, flexing and twisting of the patch while maintaining continuous low strain regions for mounting electronic components and routing traces.

13. The patch of claim 1 for attachment to or on or an object, or embedded in an object.

14. The patch of claim 1 in the form factor of a rectangular or a square or a triangular or other polygon or circular or elliptical or other geometric shape bandage.

15. The patch of claim 1 in the form factor that is or contains any combination of rectangles, triangles, circles, ellipses or other form factors.

16. The patch of claim 1 with different geometric patterning of different numbers and shapes and orientations of low strain domains, different numbers and orientation of geometrically structured hinge-like domains, and different geometries of hinge-like domains.

17. The patch of claim 1 as a programmable circuit board for arbitrary applications.

18. The patch of claim 1 fabricated using current flex circuit manufacturing methods and materials.

19. The patch of claim 1 comprising a cloud storage to receive sensor data.

20. The patch of claim 1 where the polymer layers are current flex manufacturing polymers such as Kapton, polyimides, polyamides, polyesters, or other as well as elastomers such as silicone rubbers (PDMS) or polyurethanes or other elastomers and the interconnects are metals that have high electrical conductivity, such as copper or gold, or where the interconnects are emerging stretchable electronic materials and stretchable conductive inks and materials.

Smart Clothing

Figure 9:
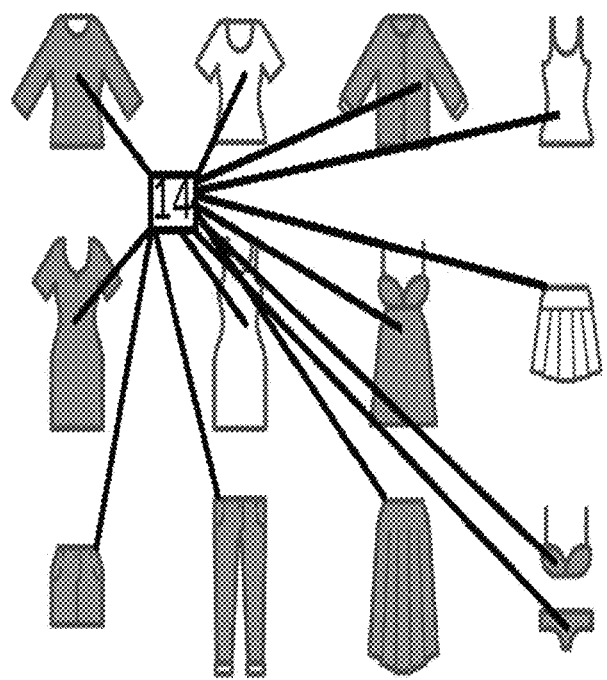
FIG. 9 shows exemplary smart clothing.
Figure 10:
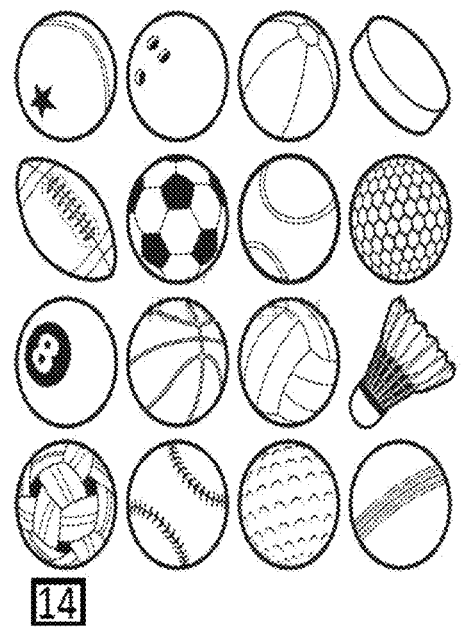
FIG. 10 shows exemplary smart balls.

FIG. 9 shows an exemplary shirt based embodiment where sensors can be positioned anywhere on the shirt and when worn, can capture position, video, and vital signs. One embodiment uses Samsung's Bio-Processor to process the bio-signals it measures without the need of external processing parts with five AFEs including bioelectrical impedance analysis (BIA), photoplethysmogram (PPG), electrocardiogram (ECG), skin temperature, and galvanic skin response (GSR) into a single chip solution that measures body fat, and skeletal muscle mass, heart rate, heart rhythm, skin temperature and stress level, respectively. Features of the smart clothe can include:

1. A smart clothing, comprising:
   a shirt, underwear, pant or sock;
   a band to be secured to the a shirt, underwear, pant or sock;
   a processor in the band and coupled to a wireless transceiver;
   an EKG amplifier coupled to the band;
   a sensor disposed in the band; and
   an accelerometer disposed within the band to detect acceleration of the band.

2. The clothing of claim 1, comprising a plurality of bands forming a mesh network and communicating episodically to conserve power.

3. The clothing of claim 1 where the electronic components, sensors, and interconnects of the patch monitor, record, process and/or transmit events of interest (such as accelerometers and gyroscopes for impact events, temperature sensors for temperature and/or temperature gradients, pressure sensors, moisture sensors, chemical sensors).

4. The clothing of claim 1 comprised for sensing and/or monitoring impact events where the sensors are accelerometers, gyroscopes, and/or pressure sensors.

5. The clothing of claim 1 comprised for sensing and/or monitoring and/or controlling ongoing events where the sensors monitor temperature, temperature gradients, motion, position, environmental or chemical levels, or other such information.

6. The clothing of claim 1 comprised for sensing events or other information including mounting multiple distributed sensors for obtaining spatial and/or temporal distribution in the data and/or multiple sensors sensing different information and data.

7. The clothing of claim 1 including wired or wireless communication, such as a Bluetooth module or a wi-fi module or other transmission module, transmitting and/or receiving information to/from another device.

8. The clothing of claim 1 with power and energy sources including batteries, wired or wireless rechargeable batteries, photovoltaics, thermoelectrics, or energy harvesters.

9. The clothing of claim 1 with an adhesive backing for directly adhering to a head, a body, or an object.

10. The clothing of claim 1 contained in an adhesive or a sleeve for adhering or attaching to a head, a body, or an object.

11. The clothing of claim 1 coated with a coating for protection against the elements (water, moisture, dirt, other) and/or for increased comfort to the wearer.

12. The clothing of claim 1, comprising a geometrically patterned substrate that contains regions of low strain domains (LSDs) bridged by hingeable strain relief features (SRFs) which also contain low strain regions and enable the stretching, flexing and twisting of the patch while maintaining continuous low strain regions for mounting electronic components and routing traces.

13. The clothing of claim 1 for attachment to or on or an object, or embedded in an object.

14. The clothing of claim 1 in the form factor of a rectangular or a square or a triangular or other polygon or circular or elliptical or other geometric shape bandage.

15. The clothing of claim 1 in the form factor that is or contains any combination of rectangles, triangles, circles, ellipses or other form factors.

16. The clothing of claim 1 with different geometric patterning of different numbers and shapes and orientations of low strain domains, different numbers and orientation of geometrically structured hinge-like domains, and different geometries of hinge-like domains.

17. The clothing of claim 1 as a programmable circuit board for arbitrary applications.

18. The clothing of claim 1 fabricated using current flex circuit manufacturing methods and materials.

19. The clothing of claim 1 comprising a cloud storage to receive sensor data.

20. The clothing of claim 1 where the polymer layers are current flex manufacturing polymers such as Kapton, polyimides, polyamides, polyesters, or other as well as elastomers such as silicone rubbers (PDMS) or polyurethanes or other elastomers and the interconnects are metals that have high electrical conductivity, such as copper or gold, or where the interconnects are emerging stretchable electronic materials and stretchable conductive inks and materials.

Smart Handle

Figure 11A:
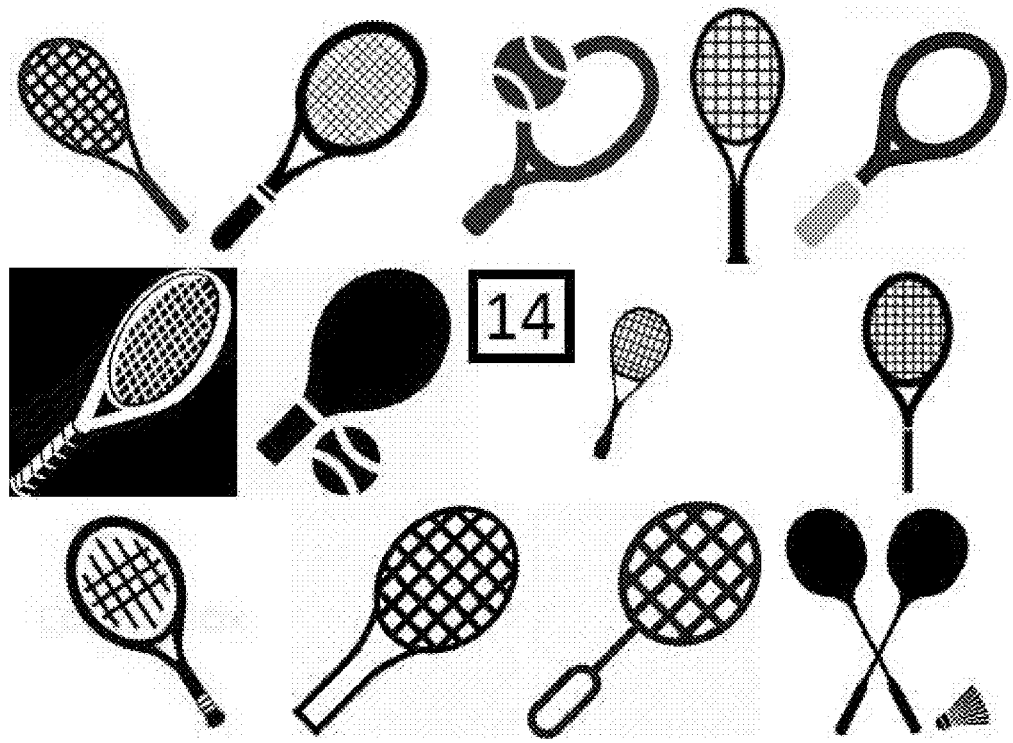
Figure 11B:
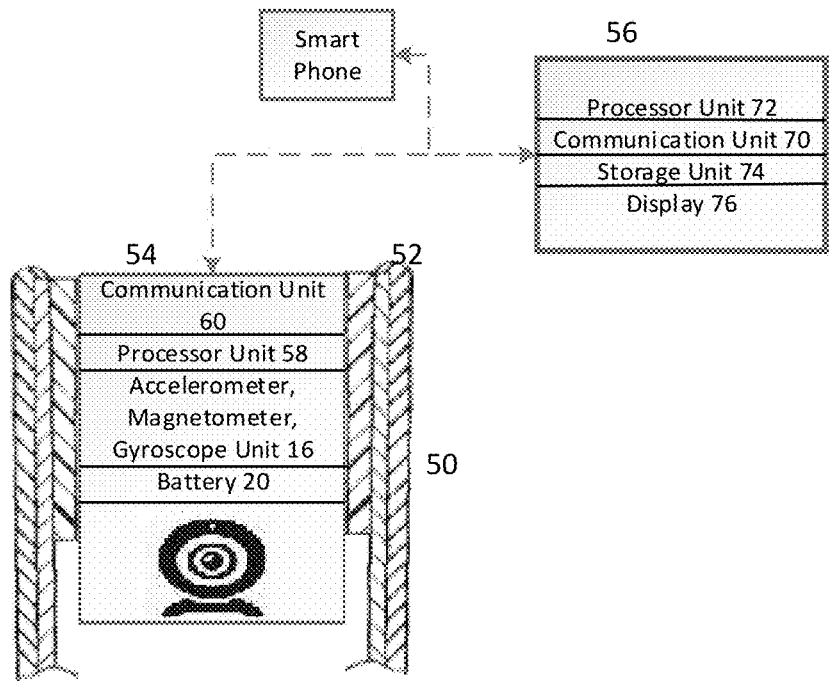
FIG. 11B shows electronics in the handle for golf clubs, rackets, or kung fu sticks.

FIGS. 11A-11B show an exemplary smart handle for sports such as tennis, badminton, table tennis, and golf, among others. The wireless sensor electronics 14 is mounted on a handle in the example of FIG. 11B. The handle can be embedded or can be removed upon completion of the sports event. The sports event does not have to be real, for example, in Virtual Reality (VR) sports applications, sensors including gyroscopes and cameras can be positioned on various body portions to capture motion as well as eye tracking, mouth tracking, speech recognition, among others.

The handle includes a swing analyzer measurement portion 54 in the grip end 52 of the handle of a golf club or a tennis/badminton racket, and a remote or handheld unit 56. The swing analyzer measurement portion 54 includes an accelerometer 16 of combination accelerometer and gyroscope or magnetometer unit, a processor unit 58 coupled to the accelerometer 16, and a battery 20 that is electrically coupled to and provides power to the accelerometer 16 and processor unit 58. A camera is included to capture videos of the swing and also the game in progress for future reference. A communications unit 60 is also housed in the grip end 52 of the golf club 50, receives power from the battery 20, and is coupled to the processor unit 58. Swing analyzer measurement portion 54, with or without the communications unit 60, may be assembled as an integral unit and inserted into a hollow portion of the handle of the golf club or tennis/racket handle 50 at the grip end 52 thereof. Processor unit 58 may be an integrated device that includes hardware and software components capable of processing acceleration measured by the accelerometer(s) 16 and converting the measured acceleration into data about the force on the shaft and position of the face of the club at impact at a set distance. If the measured force exceeds a threshold the measured force or a signal derived therefrom is transmitted via the communications unit 60 to the handheld unit 56. If not, acceleration and face position at impact of the golf club or tennis racket handle 50 is obtained again. The threshold is set so that only acceleration or force measurements arising from actual swings of the golf club 50 are transmitted to the handheld unit 56. Handheld or remote unit 56 includes an application or computer program embodied on a non-transitory computer-readable medium that performs the golf ball carrying distance estimation or prediction steps, as well as manages the training stage described above. Importantly, the handheld unit 56 receives acceleration measurement data from the golf clubs/tennis rackets equipped with a swing analyzer measurement portion 54 and the club face angle in relation to the swing plane, and manages the carrying distance estimation steps for all golf clubs equipped with the swing analyzer measurement portion 54 that are designed to communicate therewith. Handheld or remote unit 56 may be a standalone unit for use only with the golf clubs equipped with the swing analyzer measurement portion 54, and incorporating the application thereon, or may be a smartphone or similar device with the application embodied thereon or downloaded thereto and that can be used for other purposes. Handheld or remote unit 56 includes a communications unit 70 that communicates with the communications unit 60 on each golf club or tennis racket handle 50, i.e., with the communications units present on all of the golf clubs 50 equipped with swing analyzer measurement portions 54 and which have been designated to communicate therewith. Communications unit 70 may be an integral part of the handheld unit 56 as is the case when the handheld unit 56 is a smartphone. Communications unit 70 may also communicate with another device such as a Smartphone, to perform more data manipulations relating to the golf swing and/or swing results to provide more information to the user. The data and the calculation/manipulation results can be stored in the Smartphone and displayed when desired. Currently usable Smartphones are Apple iOS iPhones and Android operating system phones. Handheld or remote unit 56 also includes a processor unit 72, a storage unit 74 and a display 76. When the handheld unit 56 is a smartphone or similar device, all of the processor unit 72, storage unit 74 and display 76 may be integral components thereof. Processor unit 72 performs functions similar to those performed by the processor unit 18 described above, e.g., calculates an estimated carrying distance for the golf ball based on the acceleration measured by the accelerometer(s) 16 and transmitted via the communications units 60, 70, and the type of club provided to the application or computer program in the processor unit 72. Storage unit 74 receives and stores information about the carrying distance of each club as a function of clock or swing position, e.g., in the form of a virtual table associating the type of club, the swing or swing position and the estimated carrying distance.

Other sensors can be used as well. For example, the handle can contain conductive ink to capture biometric. One embodiment uses Samsung's Bio-Processor which is an all-in-one health solution chip to measure bioelectrical impedance analysis (BIA), photoplethysmogram (PPG), electrocardiogram (ECG), skin temperature, and galvanic skin response (GSR) into a single chip solution that measures body fat, and skeletal muscle mass, heart rate, heart rhythm, skin temperature and stress level, respectively. The handle can also contain other sensors including gyroscopes, temperature and pressure sensors, moisture sensors, clocks, chemical and/or biological sensors, etc. Features of the smart handle can include:

1. A smart handle, comprising:
a handle;
a processor in the band and coupled to a wireless transceiver;
a camera coupled to the handle;
a sensor disposed in the handle; and
an accelerometer disposed within the band to detect acceleration of the handle.

2. The handle of claim 1, comprising a plurality of smart handles forming a mesh network and communicating episodically to conserve power.

3. The handle of claim 1 where the electronic components, sensors, and interconnects of the handle monitor, record, process and/or transmit events of interest (such as accelerometers and gyroscopes for impact events, temperature sensors for temperature and/or temperature gradients, pressure sensors, moisture sensors, chemical sensors).

4. The handle of claim 1 comprised for sensing and/or monitoring impact events where the sensors are accelerometers, gyroscopes, and/or pressure sensors.

5. The handle of claim 1 comprised for sensing and/or monitoring and/or controlling ongoing events where the sensors monitor temperature, temperature gradients, motion, position, environmental or chemical levels, or other such information.

6. The handle of claim 1 comprised for sensing events or other information including mounting multiple distributed sensors for obtaining spatial and/or temporal distribution in the data and/or multiple sensors sensing different information and data.

7. The handle of claim 1 including wired or wireless communication, such as a Bluetooth module or a wi-fi module or other transmission module, transmitting and/or receiving information to/from another device.

8. The handle of claim 1 with power and energy sources including batteries, wired or wireless rechargeable batteries, photovoltaics, thermoelectrics, or energy harvesters.

9. The handle of claim 1 with an adhesive backing for directly adhering to a head, a body, or an object.

10. The handle of claim 1 contained in an adhesive or a sleeve for adhering or attaching to a head, a body, or an object.

11. The handle of claim 1 coated with a coating for protection against the elements (water, moisture, dirt, other) and/or for increased comfort to the wearer.

12. The handle of claim 1, comprising a geometrically patterned substrate that contains regions of low strain domains (LSDs) bridged by hingeable strain relief features (SRFs) which also contain low strain regions and enable the stretching, flexing and twisting of the handle while maintaining continuous low strain regions for mounting electronic components and routing traces.

13. The handle of claim 1 for attachment to or on or an object, or embedded in an object.

14. The handle of claim 1 in the form factor of a rectangular or a square or a triangular or other polygon or circular or elliptical or other geometric shape bandage.

15. The handle of claim 1 in the form factor that is or contains any combination of rectangles, triangles, circles, ellipses or other form factors.

16. The handle of claim 1 with different geometric patterning of different numbers and shapes and orientations of low strain domains, different numbers and orientation of geometrically structured hinge-like domains, and different geometries of hinge-like domains.

17. The handle of claim 1 as a programmable circuit board for arbitrary applications.

18. The handle of claim 1 fabricated using current flex circuit manufacturing methods and materials.

19. The handle of claim 1 comprising a cloud storage to receive sensor data.

20. The handle of claim 1 where the polymer layers are current flex manufacturing polymers such as Kapton, polyimides, polyamides, polyesters, or other as well as elastomers such as silicone rubbers (PDMS) or polyurethanes or other elastomers and the interconnects are metals that have high electrical conductivity, such as copper or gold, or where the interconnects are emerging stretchable electronic materials and stretchable conductive inks and materials.

Smart Protective Gear

Figure 12A:
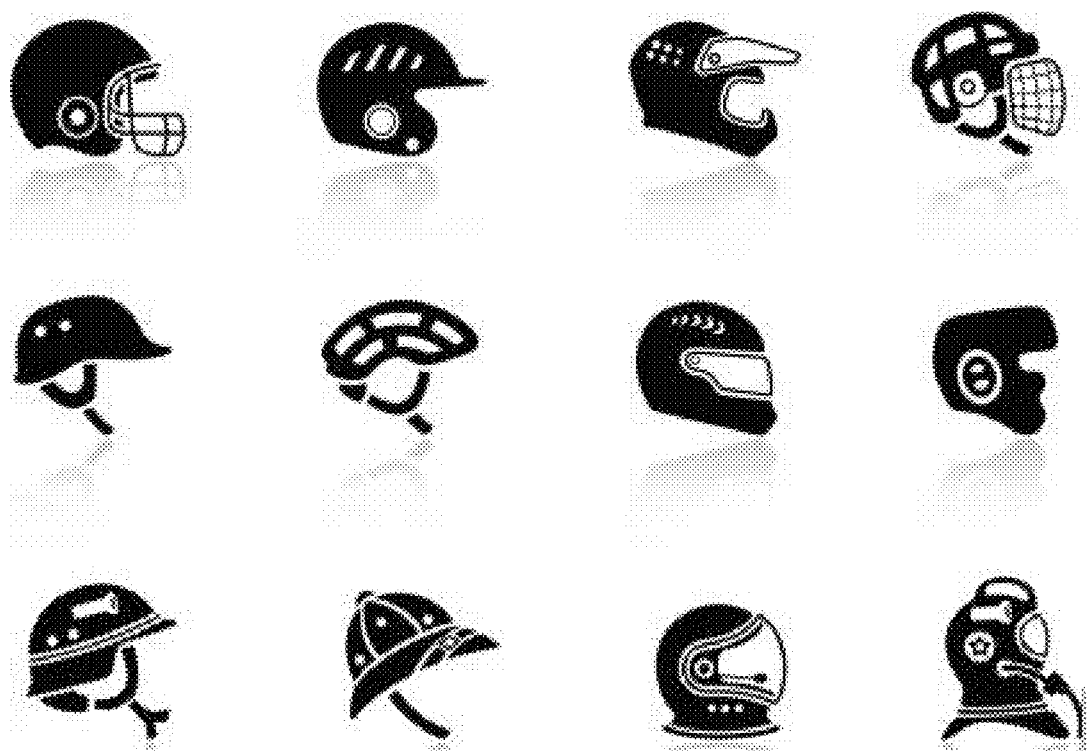
Figure 12C:
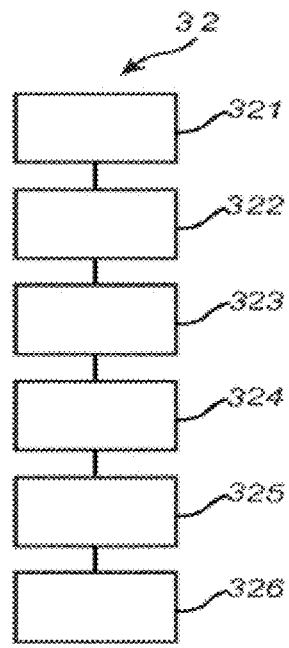
FIG. 12C shows an exemplary process to fabricate mass-customized protective gear.
Figure 12B:
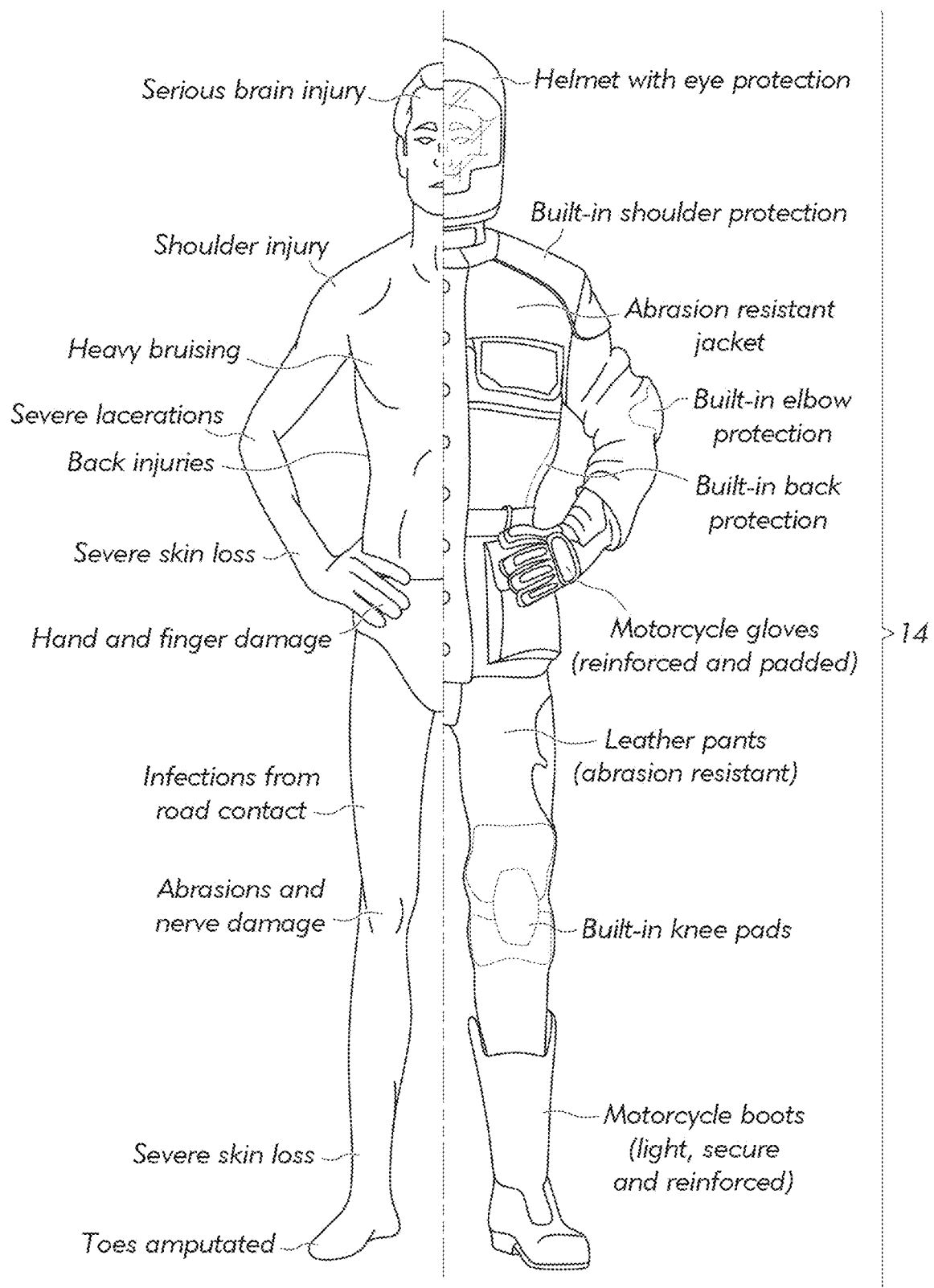

FIGS. 12A-12C illustrate smart protective gears embedded with the IoT sensors and instrumentations to report potential health issues. For soccer, the protection includes shin guards. For football, the protection includes Helmets, Chin Straps & Chin Shields, Cups & Athletic Supporters, Elbow Sleeves & Arm Pads, Back Plates & Rib Protection, Facemasks, Girdles, Helmet Visors, Shoulder Pads, Hip & Tail Pads, Mouthguards, Neck Rolls. For motorcycling, the protection includes helmet, should pads, jacket with back protection, padded gloves, leather pants, knee pads, and boots. For rock climbing, the protection includes shoes, carabiners, webbing, harnesses, among others.

The wireless sensor electronics 14 is mounted on the helmet or shoulder pad in the example of FIG. 12A or 12C. The electronics 14 can be embedded or can be removed upon completion of the sports event. The sports event does not have to be real, for example, in Virtual Reality (VR) sports applications, sensors including gyroscopes and cameras can be positioned on various body portions to capture motion as well as eye tracking, mouth tracking, speech recognition, among others.

The protection gear includes an impact sensor such as an accelerometer to indicate if concussion has occurred. Other sensors can be used as well. For example, the handle can contain conductive ink to capture biometric. One embodiment uses Samsung's Bio-Processor which is an all-in-one health solution chip to measure bioelectrical impedance analysis (BIA), photoplethysmogram (PPG), electrocardiogram (ECG), skin temperature, and galvanic skin response (GSR) into a single chip solution that measures body fat, and skeletal muscle mass, heart rate, heart rhythm, skin temperature and stress level, respectively. The handle can also contain other sensors including gyroscopes, temperature and pressure sensors, moisture sensors, clocks, chemical and/or biological sensors, etc.

Impact sensors, or accelerometers, measure in real time the force and even the number of impacts that players sustain. Data collected is sent wirelessly via Bluetooth to a dedicated monitor on the sidelines, while the impact prompts a visual light or audio alert to signal players, coaches, officials, and the training or medical staff of the team. One such sensor example is the ADXL377 from Analog Devices, a small, thin and low-power 3-axis accelerometer that measures acceleration from motion, shock, or vibration. It features a full-scale range of ±200 g, which would encompass the full range of impact acceleration in sports, which typically does not exceed 150 g's. Specifically designed for concussion and head-trauma detection, at 3 mm×3 mm×1.45 mm, the device is small enough to be designed into a helmet. Sensitivity, listed at 6.5 mV/g with −3 dB bandwidth at 1.6 kHz, is sufficiently high for the application. When a post-impact player is removed from a game and not allowed to return until cleared by a concussion-savvy healthcare professional, most will recover quickly. If the injury is undetected, however, and an athlete continues playing, concussion recovery often takes much longer. In addition, the industry is finding that long-term problems from delayed or unidentified injury can include: Early dementia, Depression, Rapid brain aging, and Death. The cumulative effects of repetitive head impacts (RHI) increases the risk of long-term neuro-degenerative diseases, such as Parkinson's disease, Alzheimer's, Mild Cognitive Impairment, and ALS or Lou Gehrig's disease. The sensors' most important role is to alert to dangerous concussions. Yet, the act of real-time monitoring brings these players to the attention of their coaches not only to monitor serious impacts but, based on the data provided by the sensors, also help to modify a player's technique so that they are not, for example, keeping their head low where they can sustain injury to the front and top of the skull. In the NFL there also has been an aggressive crackdown against hits to the head and neck—a response to the ongoing concussion crisis— resulting in immediate penalty to players using their helmets as a "weapon". Customized mouthguards also have sensors therein. A customized mouthguard has tested to be 99 percent accurate in predicting serious brain injury after near-concussive force, according to an Academy of General Dentistry study2. Teeth absorb and scatter infrared light, which shows how much force is taking place at the moment of impact.

Features of the smart protective gear can include:
1. A smart protection gear, comprising:
    a wearable surface;
    a processor in the band and coupled to a wireless transceiver;
    a camera coupled to the surface;
    a sensor disposed in the surface; and
    an accelerometer disposed within the band to detect acceleration of the surface.
2. The protection gear of claim 1, comprising a plurality of smart protection gears forming a mesh network and communicating episodically to conserve power.
3. The protection gear of claim 1 where the electronic components, sensors, and interconnects of the protection gear monitor, record, process and/or transmit events of interest (such as accelerometers and gyroscopes for impact events, temperature sensors for temperature and/or temperature gradients, pressure sensors, moisture sensors, chemical sensors).
4. The protection gear of claim 1 comprised for sensing and/or monitoring impact events where the sensors are accelerometers, gyroscopes, and/or pressure sensors.
5. The protection gear of claim 1 comprised for sensing and/or monitoring and/or controlling ongoing events where the sensors monitor temperature, temperature gradients, motion, position, environmental or chemical levels, or other such information.
6. The protection gear of claim 1 comprised for sensing events or other information including mounting multiple distributed sensors for obtaining spatial and/or temporal distribution in the data and/or multiple sensors sensing different information and data.
7. The protection gear of claim 1 including wired or wireless communication, such as a Bluetooth module or a wi-fi module or other transmission module, transmitting and/or receiving information to/from another device.
8. The protection gear of claim 1 with power and energy sources including batteries, wired or wireless rechargeable batteries, photovoltaics, thermoelectrics, or energy harvesters.
9. The protection gear of claim 1 with an adhesive backing for directly adhering to a head, a body, or an object.
10. The protection gear of claim 1 contained in an adhesive or a sleeve for adhering or attaching to a head, a body, or an object.
11. The protection gear of claim 1 coated with a coating for protection against the elements (water, moisture, dirt, other) and/or for increased comfort to the wearer.
12. The protection gear of claim 1, comprising a geometrically patterned substrate that contains regions of low strain domains (LSDs) bridged by hingeable strain relief features (SRFs) which also contain low strain regions and enable the stretching, flexing and twisting of the protection gear while maintaining continuous low strain regions for mounting electronic components and routing traces.
13. The protection gear of claim 1 for attachment to or on or an object, or embedded in an object.
14. The protection gear of claim 1 in the form factor of a rectangular or a square or a triangular or other polygon or circular or elliptical or other geometric shape bandage.
15. The protection gear of claim 1 in the form factor that is or contains any combination of rectangles, triangles, circles, ellipses or other form factors.
16. The protection gear of claim 1 with different geometric patterning of different numbers and shapes and orientations of low strain domains, different numbers and orientation of geometrically structured hinge-like domains, and different geometries of hinge-like domains.
17. The protection gear of claim 1 as a programmable circuit board for arbitrary applications.
18. The protection gear of claim 1 fabricated using current flex circuit manufacturing methods and materials.
19. The protection gear of claim 1 comprising a cloud storage to receive sensor data.
20. The protection gear of claim 1 where the polymer layers are current flex manufacturing polymers such as Kapton, polyimides, polyamides, polyesters, or other as well as elastomers such as silicone rubbers (PDMS) or polyurethanes or other elastomers and the interconnects are metals that have high electrical conductivity, such as copper or gold, or where the interconnects are conductive inks.

Custom Gear

In one aspect, the protective gear is custom formed to the athlete's body. This is done in FIG. 12C as follows:
321) perform 3D scan of person and create 3D model
322) form positive mold from the 3D model 323) place mold into 2 phase 3D printer to form a negative
324) put composite material into mold and form composite protection gear
325) embed IoT electronics into one or more locations into the composite protection gear
326) link IoT electronics with mobile devices and cloud based storage and process impact data and warn user if impact is unsafe.

The protection gear or footwear can be custom produced at the request of a customer, who can specify the nature of the customization for one or more pairs of helmet, protective gear, or footwear. Each helmet of the footwear may have a different design, message or message portion designed into it and rendered using the bed of pins described below to make the custom helmet or shoe design messages or shapes, and then the bottom sole can be fabricated using the reformable bed described below. Once the negative is fixed in the reformable bed, suitable materials for the bottom sole can be deposited and cured and can include rubber, plastic, or foam. Further customization can be done by a Computerized Numerical Control (CNC) where component design can be integrated with computer-aided design (CAD) and computer-aided manufacturing (CAM) programs. The device can be programmed to use a number of different tools-drills, saws, and so on. Alternatively a number of different machines can be used with an external controller and human or robotic operators that move the component from machine to machine. Regardless, a series of steps needed to produce a part can produce a part that closely matches the original CAD design in a highly automated fashion. In accordance with aspects of the subject matter disclosed herein through the use of reformable bed and a suitably programmed CNC tools, customized footwear with custom cut sole designs, can cost effectively be created in small quantities and yet scalable for mass-customization.

1. A method of producing a component of customized wearable protection gear, the method comprising:
   capturing the 3D model of a person and adjusting the 3D model to customize a shape to optimize protection or performance;
   using a rapid prototyping machine such as 3D printer or a bed of pins to render a positive model of the shape; and
   impressing the positive model into a reformable mold to form the component of the wearable protective gear.

2. The method of claim 1, wherein the component comprises a helmet, protective padding, shoulder padding, seat, shoe, or sole.

3. The method of claim 1, comprising fabricating a plurality of components in parallel.

4. The method of claim 1, wherein the component comprises shin guard, Helmet, Chin Strap, Chin Shields, Cup, Athletic Supporter, Elbow Sleeve, Arm Pad, Back Plate, Rib Protection, Facemask, Girdle, Helmet Visor, Shoulder Pad, Hip & Tail Pad, Mouthguard, Neck Roll, Knee Pad, Boot.

5. The method of claim 1, comprising joining the component with an upper to form a shoe.

6. The method of claim 5, wherein the shoe comprises a jogging shoe, basketball shoe, soccer shoe, miming shoe, climbing shoe, flip flop, sandal, or boot.

7. The method of claim 1, wherein the reformable mold comprises sand having a liquid state and a solid state.

Shock Protection

In one embodiment, the sole is not completely filled with material, but is formed as a lattice structure. The system generates triangulated surfaces for export to additive manufacturing (AM) processes. Implementing a process that coverts a CAD object into an image, known as voxelisation, the company uses an image-based method which allows designers to generate implicitly defined periodic lattice structures suitable for additive manufacturing applications and finite element analysis (FEA). The system generates robust lattice structures can overcome the problems faced with hollowing out a part to reduce weight and optimize designs prior to 3D printing. Cellular lattice structures can be used to replace the volume of CAD and image-based parts, reducing weight whilst maintaining optimal performance. In this way, the shoes can be light weight yet strong and provide shock impact absorption during running for the wearer.

Topology optimization can be used to drive the material layout including the lattice regions. From this new topology optimization implementation, the system can identify void regions in the design space, where the material can be removed, regions where solid material is needed, and regions where lattice structure is required. This allows the system to generate the optimal hybrid or blended solid-lattice design based on desired functionality of the part.

Lattice structures can be considered as porous structures. In the case of topology optimization, the semi-dense elements are like the porous media. To refine the design, a second-phase involves a detailed sizing optimization where the end diameters of each lattice cell member are optimized. This allows for further weight reduction while meeting design requirements, such as buckling, stress, and displacement.

A piezo material can be actuated to generate a vibration that cancels incoming shock on the wearer. In one embodiment, the system tracks the shock such as the foot contact patterns and generates an anti-vibration signal to cancel the shock generated when the foot contacts the ground. In this embodiment, a processor receives foot ground contact using an accelerometer. The stride pattern is determined, and the next foot ground contact is detected, and the piezo material is actuated with a counter signal to cancel the expected shock. This is similar to the noise cancellation, except the vibration/shock is canceled.

In one hybrid embodiment, the shoes incorporate passive and active isolation elements. The passive component consists of springs which support the load weight and provide isolation over a broad spectrum. These springs provide a basic level of isolation in the lower frequencies and excellent isolation in the higher frequencies (above 200 Hz). They also support the load while allowing for travel of the actuators in the active component. The performance of the springs is augmented and corrected by an active isolation component. The active isolation component consists of vibration sensors, control electronics, and actuators. The vibration sensors are piezo accelerometers. A plurality of sensors in each isolation system are positioned in different orientations to sense in all six degrees of freedom. The piezo accelerometers convert kinetic vibration energy into electrical signals which are transmitted to the control electronics. The electronics reconcile and process the signals from the various sensors using a processor. The electronics then send a cancellation signal to the actuators. The actuators generate vibrations that are equal to the incoming vibrations but out of phase in relation to the incoming vibrations. This results in cancellation of the incoming vibrational noise, leaving the wearer undisturbed. This process occurs within 5-20 milliseconds of a vibration entering the system.

Car Repair/Maintenance

Figure 13:
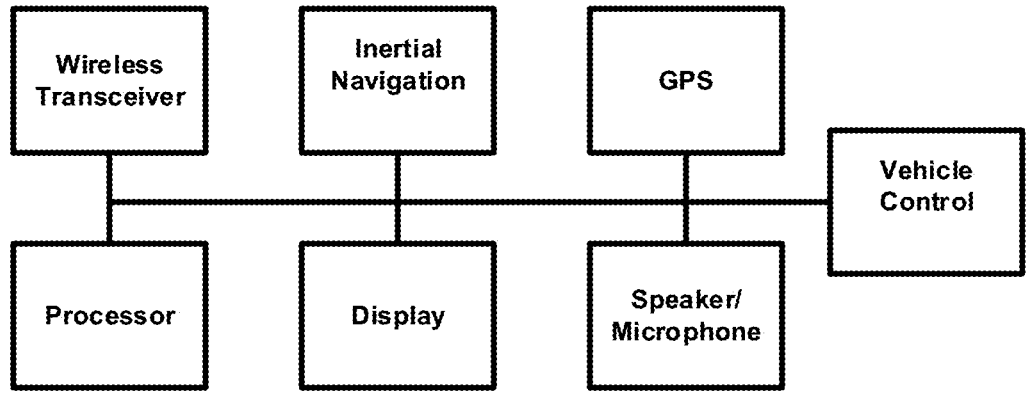
FIG. 13 shows an exemplary smart vehicle.

The sensors can be part of a car, a motorcycle, a bicycle, a boat, a plane, a dirigible, or a drone, for example. FIG. 13 shows an exemplary smart vehicle. The sensors can be used for maintenance prediction and in case of component failure, to help the driver to navigate safely. For example, the vehicle can monitor brake pad wear and adjusting how hard the brake needs to be applied in light of other vehicles and how fast does the vehicle need to come to a complete stop. In addition to changing the way the vehicle brake, the vehicle may change the way it maneuvers in other ways as well, such as accelerating differently or changing directions. For instance, the vehicle may accelerate more slowly if the measured oil pressure is excessively high. The vehicle may also turn more or less tightly in order to mitigate wear. The vehicle may also use other systems and methods to determine the state of a vehicle component. For example, the vehicle may monitor how far it takes the car to stop compared to expected braking distance. If the distance is longer than expected, such as taking longer than it has in the past, the computer system may determine that the brakes are worn and start braking earlier. The system and method may also estimate the state of a component based on its repair service record. In that regard, the processor may query data 134 or an external database (e.g., a server with which the vehicle is in wireless communication) for repair records and estimate the wear on a component based on the length of time since the last repair.

The system and method may rely on other information to change the way the vehicle is maneuvered. For instance, the vehicle may sense weight distribution and adjust maneuvering in response to the changes in the loading and/or weight distributions on the vehicle. The vehicle may further move differently when there is only one user in the vehicle than four passengers on board, or differently with light loads than with hauling a trailer behind. The vehicle may also adapt the driving to the observed environmental changes such as weather or roadway conditions.

Modeling of the patterns of changes in the vehicle's performance and conditions, as well as modeling of the patterns of changes in the driving environment, may be performed by the autonomous driving computer system. Alternatively, predetermined models may be stored in the autonomous driving system. The computer system may process the observed data, fit them into the 3D models in FIGS. 7A-7I, and issue compensation signals accordingly.

The vehicle may take the steps necessary to repair a component. By way of example, when the vehicle is not being used by anyone, the vehicle may autonomously and without direct human assistance navigate to a repair facility, notify the facility of the component that requires repair and return to its original location when the repair is finished.

Gesture Sensor for Vehicular Control

In an exemplary gesture recognition system. The system takes advantage of the numerous cameras onboard the vehicle for navigation and mapping purposes, and additionally includes the gesture control feature. The cameras can be any type of camera, including cameras sensitive across the visible spectrum or, more typically, with enhanced sensitivity to a confined wavelength band (e.g., the infrared (IR) or ultraviolet bands); more generally, the term "camera" herein refers to any device (or combination of devices) capable of capturing an image of an object and representing that image in the form of digital data. For example, line sensors or line cameras rather than conventional devices that capture a two-dimensional (2D) image can be employed. The term "light" is used generally to connote any electromagnetic radiation, which may or may not be within the visible spectrum, and may be broadband (e.g., white light) or narrowband (e.g., a single wavelength or narrow band of wavelengths). The cameras are preferably capable of capturing video images (i.e., successive image frames at a constant rate of at least 15 frames per second), although no particular frame rate is required. The capabilities of cameras are not critical to the invention, and the cameras can vary as to frame rate, image resolution (e.g., pixels per image), color or intensity resolution (e.g., number of bits of intensity data per pixel), focal length of lenses, depth of field, etc. In general, for a particular application, any cameras capable of focusing on objects within a spatial volume of interest can be used. For instance, to capture motion of the hand of an otherwise stationary person, the volume of interest might be defined as a cube approximately one meter on a side. For example, lasers or other light sources can be used instead of LEDs. For laser setups, additional optics (e.g., a lens or diffuser) may be employed to widen the laser beam (and make its field of view similar to that of the cameras). Useful arrangements can also include short- and wide-angle illuminators for different ranges. Light sources are typically diffuse rather than specular point sources; for example.

In identifying the location of an object in an image according to an embodiment of the present invention, light sources are turned on. One or more images are captured using cameras. In some embodiments, one image from each camera is captured. In other embodiments, a sequence of images is captured from each camera. The images from the two cameras can be closely correlated in time (e.g., simultaneous to within a few milliseconds) so that correlated images from the two cameras can be used to determine the 3D location of the object. A threshold pixel brightness is applied to distinguish object pixels from background pixels. This can also include identifying locations of edges of the object based on transition points between background and object pixels. In some embodiments, each pixel is first classified as either object or background based on whether it exceeds the threshold brightness cutoff. Once the pixels are classified, edges can be detected by finding locations where background pixels are adjacent to object pixels. In some embodiments, to avoid noise artifacts, the regions of background and object pixels on either side of the edge may be required to have a certain minimum size (e.g., 2, 4 or 8 pixels).

In other embodiments, edges can be detected without first classifying pixels as object or background. For example, $\Delta\beta$ can be defined as the difference in brightness between adjacent pixels, and $|\Delta\beta|$ above a threshold can indicate a transition from background to object or from object to background between adjacent pixels. (The sign of $\Delta\beta$ can indicate the direction of the transition.) In some instances where the object's edge is actually in the middle of a pixel, there may be a pixel with an intermediate value at the boundary. This can be detected, e.g., by computing two brightness values for a pixel i: $\beta L=(\beta i+\beta i-1)/2$ and $\beta R=(\beta i+\beta i+1)/2$, where pixel (i−1) is to the left of pixel i and pixel (i+1) is to the right of pixel i. If pixel i is not near an edge, $||\beta L-\beta R|$ will generally be close to zero; if pixel is near an edge, then $|\beta L-\beta R|$ will be closer to 1, and a threshold on $|\beta L-\beta R|$ can be used to detect edges.

In some instances, one part of an object may partially occlude another in an image; for example, in the case of a hand, a finger may partly occlude the palm or another finger. Occlusion edges that occur where one part of the object partially occludes another can also be detected based on smaller but distinct changes in brightness once background pixels have been eliminated.

Detected edges can be used for numerous purposes. For example, as previously noted, the edges of the object as viewed by the two cameras can be used to determine an approximate location of the object in 3D space. The position of the object in a 2D plane transverse to the optical axis of the camera can be determined from a single image, and the offset (parallax) between the position of the object in time-correlated images from two different cameras can be used to determine the distance to the object if the spacing between the cameras is known.

Further, the position and shape of the object can be determined based on the locations of its edges in time-correlated images from two different cameras, and motion (including articulation) of the object can be determined from analysis of successive pairs of images. An object's motion and/or position is reconstructed using small amounts of information. For example, an outline of an object's shape, or silhouette, as seen from a particular vantage point can be used to define tangent lines to the object from that vantage point in various planes, referred to herein as "slices." Using as few as two different vantage points, four (or more) tangent lines from the vantage points to the object can be obtained in a given slice. From these four (or more) tangent lines, it is possible to determine the position of the object in the slice and to approximate its cross-section in the slice, e.g., using one or more ellipses or other simple closed curves. As another example, locations of points on an object's surface in a particular slice can be determined directly (e.g., using a time-of-flight camera), and the position and shape of a cross-section of the object in the slice can be approximated by fitting an ellipse or other simple closed curve to the points. Positions and cross-sections determined for different slices can be correlated to construct a 3D model of the object, including its position and shape. A succession of images can be analyzed using the same technique to model motion of the object. Motion of a complex object that has multiple separately articulating members (e.g., a human hand) can be modeled using these techniques.

More particularly, an ellipse in the xy plane can be characterized by five parameters: the x and y coordinates of the center (xC, yC), the semimajor axis, the semiminor axis, and a rotation angle (e.g., angle of the semimajor axis relative to the x axis). With only four tangents, the ellipse is underdetermined. However, an efficient process for estimating the ellipse in spite of this fact involves making an initial working assumption (or "guess") as to one of the parameters and revisiting the assumption as additional information is gathered during the analysis. This additional information can include, for example, physical constraints based on properties of the cameras and/or the object. In some circumstances, more than four tangents to an object may be available for some or all of the slices, e.g., because more than two vantage points are available. An elliptical cross-section can still be determined, and the process in some instances is somewhat simplified as there is no need to assume a parameter value. In some instances, the additional tangents may create additional complexity. In some circumstances, fewer than four tangents to an object may be available for some or all of the slices, e.g., because an edge of the object is out of range of the field of view of one camera or because an edge was not detected. A slice with three tangents can be analyzed. For example, using two parameters from an ellipse fit to an adjacent slice (e.g., a slice that had at least four tangents), the system of equations for the ellipse and three tangents is sufficiently determined that it can be solved. As another option, a circle can be fit to the three tangents; defining a circle in a plane requires only three parameters (the center coordinates and the radius), so three tangents suffice to fit a circle. Slices with fewer than three tangents can be discarded or combined with adjacent slices.

To determine geometrically whether an object corresponds to an object of interest comprises, one approach is to look for continuous volumes of ellipses that define an object and discard object segments geometrically inconsistent with the ellipse-based definition of the object—e.g., segments that are too cylindrical or too straight or too thin or too small or too far away—and discarding these. If a sufficient number of ellipses remain to characterize the object and it conforms to the object of interest, it is so identified, and may be tracked from frame to frame.

In some embodiments, each of a number of slices is analyzed separately to determine the size and location of an elliptical cross-section of the object in that slice. This provides an initial 3D model (specifically, a stack of elliptical cross-sections), which can be refined by correlating the cross-sections across different slices. For example, it is expected that an object's surface will have continuity, and discontinuous ellipses can accordingly be discounted. Further refinement can be obtained by correlating the 3D model with itself across time, e.g., based on expectations related to continuity in motion and deformation. In some embodiments, light sources 808, 110 can be operated in a pulsed mode rather than being continually on. This can be useful, e.g., if light sources 808, 110 have the ability to produce brighter light in a pulse than in a steady-state operation. Light sources 808, 110 can be pulsed on at regular intervals as shown at 502. The shutters of cameras 802, 804 can be opened to capture images at times coincident with the light pulses. Thus, an object of interest can be brightly illuminated during the times when images are being captured. In some embodiments, the silhouettes of an object are extracted from one or more images of the object that reveal information about the object as seen from different vantage points. While silhouettes can be obtained using a number of different techniques, in some embodiments, the silhouettes are obtained by using cameras to capture images of the object and analyzing the images to detect object edges.

Hand-Gesture Control of Vehicle

Exemplary hand control of a smart vehicle. First, a Left Hand Gesture Based Car Control process is disclosed. In an exemplary left arm gesture based window glass control process, the process checks for the raised arm (1002). If the arm is raised (1004) it checks for the number of fingers raised (1006). The controls for windows are activated if first four fingers are raised (1008). The process allows controlling only the driver seat glass control and also all the window glass control. This decision is based on the number of fingers raised. A single finger chooses only driver glass. Movements of the glass is than controlled by the angular movement of the arm (1020), a right movement slides the glass up (1028) and a left movement slides it down (1026). The process is concluded (1030) after the windows are at the required position. At any moment the driver can choose to exit the process by forming a fist of his left arm.

A seat control process is capable of controlling both the driver seat and the front passenger seat as well. The process starts with checking for which arm is raised (1036). After the arm the process scans for the fingers (1038), first 2 fingers initiate the seat actuators (1040). Now, the driver can choose to adjust his own seat or maybe the seat of the passenger. This decision is dependent whether one or two fingers are raised (1044). The seats can be moved forth or back as per the arms angular movement (1052) (1050). As per the convenience, the seats can be adjusted. After the adjustment is done, the process concludes (1062). At any point the process can be ended if the driver forms a fist on left hand.

A left hand based gesture based mechanism for unlocking the 'Hood' and the 'Trunk' of the car is next. As it is left arm based control, the mechanism uses a camera to check the arm raised. A raised left arm initiates the process which unlocks the hood and trunk (1068). The camera than checks for the fingers that are raised (1070), the first finger is used to activate the hood & trunk control (1072). To open the trunk the driver has to make a right angular movement (1076) and an opposite movement for unlocking the hood (1078). As soon as either of the two is unlocked the process ends (1082). If the process is started by mistake or confusion, the driver can choose to exit by forming a fist on his left arm.

An exemplary process for controlling temperature of the driver and front passenger seats is next. After checking for left raised arm (1088) the camera scans for the fingers raised (1090). The first three fingers are to be used by the driver to activate seat temperature controls (1092). The driver can choose to control his seat temperature or the passenger's seat temperature by raising the appropriate number of fingers (1096). The angular movements of the left arm can be used to increase or decrease the temperature of the selected seat (1104) (1102). The process can be ended after adjusting the temperature or at any other point by forming a fist (1114).

An left arm gesture based navigation (GPS) control for a car is next. The process initializes when the driver raises his/her left arm (1120). The GPS system is activated if the all the fingers are raised i.e. an open palm (1124). Now the arm motion in the vertical and horizontal axis can be used to move the GPS pointer (1128). To select a particular destination, the pointer must be kept at the same location for a pre-defined duration of time (1144). Once the destination is set, the GPS starts routing (1146) and then exits the process (1148). The process can be ended abruptly if needed by forming a fist on left hand.

An exemplary gesture based control of drivers mirror using left arm is next. The driver initiates the process by raising the left arm (1154). The thumb is used as a trigger for activating the mirror actuators (1158). To adjust the mirror angle, the driver can move his/her arm along the vertical or horizontal axis (1162). The driver can form a fist (1170) (1168) or wait for a predefined time interval to set the mirror angle (1182). This process has an option which enables the driver to exit anytime by forming a fist on left hand.

An exemplary music control in the car using gestures of right hand is next. The process is activated if the camera scans a vertically standing right arm (1190). The car music system is initiated if the driver has an open right palm (1194). Depending upon the fingers raised after the music system is initiated either radio or just the MP3 player is started (1204). The angular movements of the arm can be used to switch between stations or songs (1206) (1202). Once the desired station or song is selected the driver can exit the process by forming a closed fist (1216). A closed fist formed anytime can be used to exit the process anytime.

An exemplary car temperature control using gestures from the right arm follows. The driver is expected to raise the first two fingers of the right arm to activate the temperature controls (1246). The temperature controlling element is the angular motion of the right arm (1250). A left motion causes decrease in temperature and vice versa (1256) (1254). Once the desire temperature is achieved, the driver can stop the process by forming a fist. A fist basically exits the process at any given point.

An exemplary control the car volume using arm gestures is next. The camera initiates the process whenever the driver raises his/her right arm (1222). The process expects the driver to raise three fingers to initiate volume control (1226). Using the right or left angular motion the volume can be increased and decreased (1230).

An exemplary technique for sliding the sun roof by the means of hand gesture can be as follows. The sun roof control process starts when the driver raises his/her right arm (1264) and first four fingers of the same (1268). The camera now scans for the angular motion of the arm (1272). A left motion pulls the roof back (1276) whereas a right motion pushes it forward so that it can be closed (1274). The process ends once the roof is entirely opened or closed and it can also be concluded by forming a fist on the right arm.

An exemplary arm gesture based technique for controlling the car wind shield wipers is next. The wiper motors are activated when the right arm along with first finger is raised (1284) (1288). The speed of the wiper motors can be controlled using the right arm angular motion (1292). The left motion decreases the speed (1298), the right motion increases the wiper speed (1296) and in order to stop the wiper a still right arm with a closed fist should be scanned by the camera (1294).

An exemplary right arm gesture based control of the rear view mirror is next. The camera scans for the right arm, if it is up the process is initiated (1306). The rear view mirror control is activated if the camera scans only a thumb on right arm (1310). Now, the rear view mirror can be adjusted vertically and horizontally, this is achieved by moving the arm with only raised thumb along the desired axis (1314). To lock the position of the mirror, the same position is to be maintained for a pre-defined interval of time. Once done the process locks the mirror and concludes (1332). The process can be ended anytime by the driver by forming a fist on his right arm.

In other embodiments, by cupping the hand on an object such as a steering wheel, the user can use voice to make calls, receive and respond to texts, launch apps, get turn-by-turn directions, find the nearest Chinese restaurant and other local businesses, or say "Play me some Barry Manilow." You can also ask Siri or Google Now to search the Internet as you roll down the Interstate. The apps will be able to pull contacts directly from the phone's address book, access favorites and bookmarks, and have user location history close at hand.

A gesture is used to control an air conditioning system in an example vehicle, in accordance with an embodiment. The vehicle may maintain a correlation between a plurality of predetermined gestures, in combination with a plurality of predetermined regions of the vehicle, and a plurality of functions, such that each gesture in the plurality of predetermined gestures, in combination with a particular region of the plurality of predetermined regions, is associated with a particular function in the plurality of functions, as described above. For example, the correlation may include a downward swiping gesture in a region that includes an air-conditioning vent associated with the function of decreasing a fan speed of an air conditioning system. Other examples are possible as well.

As shown, a fan speed indicator on the display indicates that a fan speed of the air conditioning system in the vehicle is high. At some point, the user may wish to lower the fan speed of the air conditioning system. To this end, the user may make a downward swiping gesture in a region that includes an air-conditioning vent. The camera 304 may record three-dimensional images of the downward swiping gesture in the region that includes an air-conditioning vent. Based on the three-dimensional images, the vehicle may detect the downward swiping gesture in the region that includes the air-conditioning vent.

The vehicle may then select, based on the correlation, a function associated with the downward swiping gesture in the region that includes the air-conditioning vent. For example, the downward swiping gesture in the region that includes the air-conditioning vent may be associated with the function of decreasing a fan speed of the air conditioning system, as described above. Other examples are possible as well. Once the vehicle has selected the function from the correlation, the vehicle may initiate the function in the vehicle. That is, the vehicle may decrease the fan speed in the vehicle.

In some embodiments, the vehicle may additionally determine an extent determining an extent of the downward swiping gesture and may decrease the fan speed by an amount that is, for example, proportional to the extent.

In some embodiments, in addition to initiating the function, the vehicle may trigger a feedback to the user, such as an audible feedback, a visual feedback, and/or a haptic feedback. Such feedback may be particularly useful when the function is not immediately detectable by the user, such as a small decrease in the fan speed of the climate control system or a slight repositioning of a seat.

Further, in some embodiments, the vehicle may determine an extent of the given gesture. For example, if the given gesture is a swipe gesture, the vehicle may determine an extent of the swipe (e.g., how long the swipe is in space and/or time). The vehicle may then determine an operational parameter based on the extent. For example, for a greater extent, the vehicle may determine a greater operational parameter than for a lesser extent. The operational parameter may be, for example, proportional to, or approximately proportional to, the extent. In these embodiments, when the vehicle initiates the function the vehicle may initiate the function with the determined operational parameter.

For example, if the swipe gesture is in a region that includes a window, and the swipe gesture in the region that includes the window is associated with opening the window, the vehicle may determine an extent of the swipe and further may determine how far to open the window based on the extent of the swipe. For instance, the vehicle may open the window further for a longer swipe than for a shorter swipe.

As another example, if the swipe gesture is in a region that includes an air-conditioning vent, and the swipe gesture in the region that includes the air-conditioning vent is associated with lowering a temperature in the vehicle, the vehicle may determine an extent of the swipe and further may determine how much to lower the temperature in the vehicle based on the extent of the swipe. For instance, the vehicle may lower the temperature further for a longer swipe than for a shorter swipe.

Such an extent could be determined for gestures other than a swipe gesture as well. For example, if a tap gesture is in a region that includes a speaker, and the tap gesture in the region that includes the speaker is associated with lowering a volume of an audio system, the vehicle may determine an extent of the tap (e.g., how many taps, how long the tap is held, etc.) and further may determine how much to lower the volume of the audio system based on the extent of the tap. For instance, the vehicle may lower the volume more for more taps (or a longer tap) than for fewer taps (or a shorter tap).

In some embodiments, rather than determining the extent of the gesture and the corresponding operational parameter and then initiating the function with the determined operational parameter, the vehicle may instead continuously determine the extent of the gesture and update the corresponding operational parameter, and may continuously initiate the function with the updated operational parameter. For example, the vehicle may detect a cover gesture in a region that includes an air-conditioning vent (e.g., such that the air-conditioning vent is covered), and the cover gesture in the region that includes the air-conditioning vent may be associated with lowering a fan speed of the air conditioning system. Once the vehicle detects the cover gesture in the region that includes the air-conditioning vent, the vehicle may lower the fan speed (e.g., by a predetermined amount). As the vehicle continues to detect the cover gesture, the vehicle may continue to lower the fan speed (e.g., in increments of, for example, the predetermined amount, growing amounts, etc.). Once the vehicle detects that the cover gesture has ended, the vehicle may cease to lower the fan speed. As a result, during the cover gesture the vehicle may lower the fan speed by an amount that is based on the extent of the cover gesture.

In some embodiments, the vehicle may have difficulty detecting the given gesture and/or the given region. For example, the vehicle may determine that a confidence level of one or both of the given gesture and the given region is below a predetermined threshold. In these embodiments, the vehicle may request an occupant to repeat the given gesture in the given region. When the occupant repeats the given gesture in the given region, the vehicle may record additional three-dimensional images and may detect the given gesture and the given region based on the additional three-dimensional images (and, in some cases, the three-dimensional images previously recorded).

Obstacle Detection

In some embodiments, a vehicle identifies obstacles on the road, and the computer system may use one or more sensors to sense the obstacles. For example, the computer system may use an image-capture device to capture images of the road and may detect the obstacles by analyzing the images for predetermined colors, shapes, and/or brightness levels indicative of an obstacle. As another example, the computer system may project LIDAR to detect the obstacle. The computer system may estimate the location of the obstacle and control the vehicle to avoid the vehicle and yet maintain a predetermined distance from neighboring vehicles in both directions. Other vehicles behind the lead vehicle can then simply follow the lead vehicle as part of a flock. The computer system may then control the vehicle to maintain a distance between the vehicle and the at least one neighboring vehicle to be at least a predetermined minimum distance to avoid colliding with the at least one neighboring vehicle.

In an example of a situation where an obstacle 603 is present in front of a host vehicle 601 mounted with a sensor such as camera or sensor 602 in a front portion of a vehicle body. In vehicles, a vehicle-mounted sensors such as cameras, radar, and LIDAR is used in a vehicle control system such as an inter-vehicle distance alarm system, a preceding vehicle following system or a collision reducing brake system. Where an obstacle is not present in front of the host vehicle 601, since the target data is not output from the sensor 602, the vehicle velocity control system performs a control so that the vehicle operates according to a planned path. However, the path may need adjustment when an obstacle is encountered, or when weather affects the operation, or traffic condition, emergency or holiday patterns require a change in the planned path and speed.

In this example, the front obstacle 603 is another vehicle. Furthermore, in this example, as the sensor 602, a radar in one embodiment, has horizontal resolution due to a plurality of arrays installed in the horizontal direction; however, it does not have a vertical resolution. In this case, the sensor 602 outputs target data having position information such as a relative longitudinal distance, lateral position and velocity between the host vehicle 601 and the obstacle 603 to a vehicle velocity control system. In another embodiment, the sensor 602 is a camera. Pictures captured by the camera can be used to form a 3D reconstruction of the obstacles and the road. The task of converting multiple 2D images into 3D model consists of a series of processing steps: Camera calibration consists of intrinsic and extrinsic parameters, and the camera calibration is usually required for determining depth. Depth determination calculates—depth. The correspondence problem, finding matches between two images so the position of the matched elements can then be triangulated in 3D space. With the multiple depth maps the system combines them to create a final mesh by calculating depth and projecting out of the camera—registration. Camera calibration will be used to identify where the many meshes created by depth maps can be combined together to develop a larger one, providing more than one view for observation to have a complete 3D mesh.

The vehicle velocity control system performs controls such as a control for maintaining the distance from the obstacle 603, and a control for executing an alarm or velocity reduction in a case where collision with the obstacle 603 is predicted, according to the position information about the input target data.

For example, obstacles such as land slip and falling rocks can appear unexpectedly on a mountain road. Image data in the fall monitoring area is processed by car computers and/or transmitted to a cloud processing system, and images are frame-difference-processed to identify the new obstacles. Thereafter, in the case where there are no variations in the extracted component data representing the body and in particular in the case where there are no moving variations, when several frames with an interval of a predetermined time are processed in a similar way, the processor detects the obstacle and transmits a warning signal to adjacent vehicles and/or to a traffic display board. The warning information can be incorporated by the driving software of other drivers that there are road obstacles by land slip.

In another embodiment, the obstacle can be the result of a car accident or emergency. The system automatically detects the occurrence of an emergency and provides safety at the scene. This is done by diverting traffic flow near the point of emergency to a point where traffic resumes normal flow. The system secures the incident site to protect emergency personnel, their equipment and the public, from hazardous conditions at the scene and throughout the traffic control zone. The system can establish a traffic control set-up that gives motorists adequate warning and reaction time. The system also separates pedestrians from vehicular traffic and limits access to the site to authorized persons only. One embodiment directs vehicles through an emergency traffic control zone with the following: Advance Warning Area should alert vehicles that there is a traffic situation or difficulty ahead which will require some action on its part; Approach area should identify the nature of the equipment or vehicle that is about to encounter and allow them to analyze the situation; Transition Area should provide an indication as to the expected action to be taken by the vehicle to decide on a course of action and execute safe driving techniques prior to entering the Activity Area; and Activity Area includes Fend Off Position of the emergency vehicle, Buffer Zone (refers to scene protection area between the first emergency vehicle and the incident site), Incident Site (Restricted to authorized personnel only), Traffic Space (Area where traffic is allowed to pass by the Activity Area), and Staging Area (Emergency Vehicles not immediately required to perform a function or shielding at the incident scene should be directed to stage in this area. The area should be downstream/upstream of the incident site and the location should not create a traffic hazard or obstruction). The system can determine a Termination Area from the downstream side of the Staging Area to the point where normal traffic is able to resume. The information for an emergency is incorporated into the 3D model for vehicular processing.

Weather conditions can affect the driving plan. For cameras, it affects the ability to see, which is very limited in adverse weather conditions such as rain, fog, ice, snow, and dust. For example, if the fog becomes so thick the system can suggest the car be moved completely off the road. The car system also slows down for rain, drizzle, or snow on the road. This is when many road surfaces are most slippery because moisture mixes with oil and dust that has not been washed away. The slippery roads can reduce traction and control of the vehicle may be compromised. The system can detect wet road surface via its camera or water sensors. Wet road surfaces can cause tires to hydroplane (skim on a thin layer of water). This could result in loss of control and steering ability. Hydroplaning is caused by a combination of standing water on the road, car speed, and under-inflated or worn-out tires. Thus, the system can check the pressure of the tires by communicating with the tire sensors. The 3D modeling system also incorporates the effects of high temperatures, sun glare and high winds. One exemplary 3D modeling process for navigation is detailed next.

An exemplary system can perform data fusion based on sensor based detection of objects, change in weather and traffic, and holiday/emergency conditions, among others. The process checks all the sensors for change in weather (2004), detection of object (2002) and the GPS for current traffic conditions (2006). For each given sensor for detecting objects in a vehicle's environment, the process generates a 3D model of the given sensor's field of view; obstacle information from front cars using vehicle-vehicle communication (DRSC); neighboring car driver preference information; traffic information including emergency information. The process can adjust one or more characteristics of the plurality of 3D models based on the received weather information to account for an impact of the actual or expected weather conditions on one or more of the plurality of sensors. After the adjusting, aggregating, by a processor, the plurality of 3D models to generate a comprehensive 3D model; combining the comprehensive 3D model with detailed map information; and using the combined comprehensive 3D model with detailed map information to maneuver the vehicle. In FIG. 7A, the process checks sensors for object detection (2008) and then checks for confirmations from other vehicles over V2V communication such as DSRC and then generates 3D model therefrom. The process can also check for weather change (2004) and correlate the weather change to generate an updated 3D model. Similarly, the process integrates traffic flow information (2006) and updates the 3D model as needed. FIG. 7B shows an exemplary process for identifying the object, while FIG. 7C-7H show in more details the object modeling process. The process checks sensors for object detection and scans the object against 3D library for matches. If a match is found, the process sets the object to the object in the library, and otherwise the process performs a best-guess of what the object is and send the object identification for subsequent 3D modeling use.

Exemplary detection of objects outside of the vehicle and guidance on their handling is next. The detected objects can include automobile, a pedestrian, structure, or a bicycle, for example. The system assists the driver by identifying the objects as potential "threats" and recommend options for the driver. For example, the system can perform the following:

detecting an object external to a vehicle using one or more sensors;
determining a classification and a state of the detected object;
estimating the destination of the object;
predicting a likely behavior of the detected object based on prior behavior data and destination;
preparing the vehicle to respond based at least in part on the likely behavior of the detected object; and
notifying a driver of options based on the likely behavior.

For example, the state of the detected object can be related to at least one of: location, traffic lane in which the detected object is traveling, speed, acceleration, entry onto a road, exit off of a road, activation of headlights, activation of taillights, or activation of blinkers. The behavior data is based on movement data for a plurality of other objects at one or more locations. The movement data are tracked using one of: satellite imagery, roadside cameras, on-board GPS data, or sensor data acquired for other nearby vehicles. The system can send a driver recommendation or vehicle command to orient the vehicle includes positioning the vehicle at a predetermined distance from the detected object, the predetermined distance being based, at least in part, on the classification of the detected object. The likely behavior of the detected object can be provided as a probability of the detected object entering to one or more states. The process includes receiving updated behavior data; and wherein predicting the likely behavior of the detected object is based at least in part on the updated behavior data. The driver can be informed of the options using haptic interface or a heads-up display. The process can also share the likely behavior of the object to neighboring vehicles using vehicle-to-vehicle communication.

The process may cause the vehicle to take particular actions in response to the predicted actions of the surrounding objects. For example, if other car is turning at the next intersection, the process may slow the vehicle down as it approaches the intersection. In this regard, the predicted behavior of other objects is based not only on the type of object and its current trajectory, but also based on some likelihood that the object may obey traffic rules or predetermined behaviors. In another example, the process may include a library of rules about what objects will do in various situations. For example, a car in a left-most lane that has a left-turn arrow mounted on the light will very likely turn left when the arrow turns green. The library may be built manually, or by the vehicle's observation of other vehicles (autonomous or not) on the roadway. The library may begin as a human built set of rules which may be improved by the vehicle's observations. Similarly, the library may begin as rules learned from vehicle observation and have humans examine the rules and improve them manually. This observation and learning may be accomplished by, for example, tools and techniques of machine learning. In addition to processing data provided by the various sensors, the computer may rely on environmental data that was obtained at a previous point in time and is expected to persist regardless of the vehicle's presence in the environment. For example, the system can use highly detailed maps identifying the shape and elevation of roadways, lane lines, intersections, crosswalks, speed limits, traffic signals, buildings, signs, real time traffic information, or other such objects and information. For example, the map information may include explicit speed limit information associated with various roadway segments. The speed limit data may be entered manually or scanned from previously taken images of a speed limit sign using, for example, optical-character recognition. The map information may include three-dimensional terrain maps incorporating one or more of objects listed above. For example, the vehicle may determine that another car is expected to turn based on real-time data (e.g., using its sensors to determine the current GPS position of another car) and other data (e.g., comparing the GPS position with previously-stored lane-specific map data to determine whether the other car is within a turn lane). These objects may have particular behavior patterns that depend on the nature of the object. For example, a bicycle is likely to react differently than a motorcycle in a number of ways. Specifically, a bicycle is more likely to make erratic movements when compared with a motorcycle, but is much slower and thus can be handled with ease compared to a speeding motorcycle. For each classification, the object data may also contain behavior information that indicates how an object having a particular classification is likely to behave in a given situation. Vehicle may then autonomously respond to the object based, in part, on the predicted behavior.

In an exemplary system for crowd-sourcing navigation data, the system includes a crowdsourcing server in communication with a plurality of vehicles 1 . . . n. The vehicles i performs peer-to-peer discovery and crowd-sourced navigation. The system receives proximity services for a group of vehicles traveling a predetermined route using peer-to-peer discovery, receives crowdsourcing data from said plurality of vehicles, sharing crowdsourcing data to the group of vehicles (or a subsequent group of vehicles) traveling the route of interest. Such information can be used in providing navigation guidance to the vehicle traveling the route using the crowdsourced data. In one aspect, the vehicles traveling the same route can be determined using a vehicle to vehicle communication protocol that facilitate identifying peers based upon encoded signals during peer discovery in a peer to peer network. The system can be WiFi or cellular based such as the Proximity Services via LTE Device Broadcast, among others. In one embodiment, the identification of peers based upon encoded signals during peer discovery in a peer to peer network can be done. For example, direct signaling that partitions a time-frequency resource into a number of segments can be utilized to communicate an identifier within a peer discovery interval; thus, a particular segment selected for transmission can signal a portion of the identifier, while a remainder can be signaled based upon tones communicated within the selected segment. Moreover, a subset of symbols within the resource can be reserved (e.g., unused) to enable identifying and/or correcting timing offset. Further, signaling can be effectuated over a plurality of peer discovery intervals such that partial identifiers communicated during each of the peer discovery intervals can be linked (e.g., based upon overlapping bits and/or bloom filter information). The method can include transmitting a first partial identifier during a first peer discovery interval. Also, the method can comprise transmitting a second partial identifier during a second peer discovery interval. Further, the method can include generating bloom filter information based upon the combination of the first partial identifier and the second partial identifier. Moreover, the method can comprise transmitting the bloom filter information to enable a peer to link the first partial identifier and the second partial identifier. Another embodiment communicates using LTE Direct, a device-to-device technology that enables discovering thousands of devices and their services in the proximity of ~500 m, in a privacy sensitive and battery efficient way. This allows the discovery to be "Always ON" and autonomous, without drastically affecting the device battery life. LTE Direct uses radio signals—called 'expressions'—which can be private and discreet (targeted securely for certain audiences only) or public (transmitted so that any application can receive them). Public expressions are a common language available to any application to discover each other, and this is the door to consumer utility and adoption. Public expressions exponentially expand the field of value. For example, vehicles that share same driving segments can broadcast expressions indicating their path(s). The system detects vehicles in the same segment as part of the proximity services for capturing and sharing crowd-sourced navigation data. Public expressions combine all applications—all value—into one single network, thereby expanding the utility of the system. The crowdsourcing data includes vehicle performance information and GPS locations of a vehicle; and wherein the vehicle data includes odometer information, speedometer information, fuel consumption information, steering information. The data includes information relating to closing of a lane using the crowdsourcing data; predicting an avoidance maneuver using the crowdsourcing data; predicting a congestion with respect to a segment of the route of the at least one vehicle using the crowdsourcing data; and predicting traffic light patterns using the crowdsourcing data. The system can determine the presence of obstacles in a road lane by monitoring a pattern of vehicle avoidance of a particular location of the lane. The obstacles can be rocks or debris on the lane, closure of a lane, inoperative vehicles on the lane, or vehicles suffering from an accident, among others. The vehicular avoidance information can be sent to vehicles that are planning to use that particular road section to optimize travel, for example. The system can detect closing of a lane by monitoring changes of vehicle direction at a location on the route of the at least one vehicle; and determining a lane is closed in response to a number of changes of vehicle direction being larger than a predetermined threshold value. The system can share prior vehicle's avoidance maneuver by monitoring change of vehicle direction and distance traveled at a close vicinity of a location on the route of a lead vehicle; and determining an avoidance maneuver in response to a ratio of change of vehicle direction and distance traveled being less than a predetermined threshold value. The system can determine a route based at least in part on an amount of time predicted for travelling from a starting location to a destination location of the route using the crowdsourcing data; and determining a route based at least in part on a predicted fuel consumption of the route using the crowdsourcing data. The determining information corresponding to a route of interest to at least one vehicle further can include monitoring a distance traveled by the at least one vehicle after reaching a destination, and predicting availability of parking spaces at the destination based at least in part on the distance traveled; and monitoring an amount of time traveled by the at least one vehicle after reaching a destination, and predicting availability of parking spaces at the destination based at least in part on the amount of time traveled. The determining information corresponding to a route of interest to at least one vehicle further comprises: measuring a time taken to travel a predefined percent of the route until the at least one vehicle comes to a halt at a predetermined location; and predicting an average amount of time used to find parking at the predetermined location using the time taken to travel a predefined percent of the route. The determining information corresponding to a route of interest to at least one vehicle further comprises at least one of: determining popularity of a fueling station along the route; determining type of fuel sold at the fueling station along the route; determining popularity of a business along the route; and determining popularity of a rest area along the route.

Crowd-Sourced Map Updating and Obstacle Annotating

Next, a system to crowd-source the updates of precision maps with data from smart vehicles is detailed. In embodiments, crowd-sourced obstacle data can be used to update a map with precision. The obstacles can be rocks, boulders, pot-holes, manhole, utility hole, cable chamber, maintenance hole, inspection chamber, access chamber, sewer hole, confined space or can be water pool or rising tidal waves that affect the road as detected by a plurality of vehicles. Such crowd-sourced information is updated into the map and annotated by time, weather and periodicity. The detected obstacle information may include a geographic location of the vehicle and a predetermined map of the road. The computer system may determine the geographic location of the obstacle by, for example, using a laser rangefinder or light detection and ranging (LIDAR) unit to estimate a distance from the obstacle to the at least two objects near the vehicle and determining the geographic location of the obstacle using triangulation, for example. Such information is updated into the map system and marked as temporal. During use, if recent vehicles take defensive driving around the temporary obstacle, the map adds the obstacles to the map for the route guidance module to advise vehicles. If recent vehicles drive the road as though the obstacle does not exist, the system removes the obstacle from the map database, but keeps track of the history in case it is a periodic obstacle. The obstacle information is also reported to government agency for repair/maintenance.

In another embodiment, if vehicles drive through the lane with a smooth line or curve, but abruptly brakes, the system infers that the road has defects or potholes, for example, and the bad infrastructure is reported for path planning (to add more travel time, or to change the route to avoid the bad road infrastructure if it is long.

The new information is used to update a digital map that lacks the current information or that contains inaccuracies or may be incomplete. The digital map stored in the map database may be updated using the information processed by a map matching module, matched segment module, and unmatched segment module. The map matching module, once it has received obstacle location and GPS traces, processes obstacle locations and GPS traces by matching them to a road defined in the digital map. The map matching module matches the obstacles and the GPS traces with the most likely road positions corresponding to a viable route through the digital map by using the processor to execute a matching algorithm. In one example, the matching algorithm may be a Viterbi matching algorithm. Where the GPS traces do match a road defined in the digital map, the matched trace to which the GPS traces match and obstacle information are sent to the matched segment module for further processing as will be described below. Where the GPS traces do not match a road defined in the digital map, the unmatched trace to which the GPS traces are correlated with and the obstacle position information are sent to the unmatched segment module for further processing. The matched segment module and unmatched segment module both provide metadata to the map updating module. The metadata may include obstacle metadata road geometry refinement metadata, road closure and reopening metadata, missing intersection metadata, missing road data and one-way correction metadata. The map updating module updates the digital map in the map database.

The process to update maps using crowd-sourced data may begin with the unmatched segment module clustering the unmatched GPS traces received from the map matching module. Many available algorithms may be suitable for this process, but in one example, an agglomerative clustering algorithm that iteratively compares GPS traces with each other and combines those that fall within a pre-determined tolerance into a cluster may be used. One example of such and algorithm uses the Hausdorff distance as its distance measure in the clustering algorithm. Once the cluster is selected, the unmatched segment module may produce a single road geometry for a cluster of unmatched GPS traces using a centerline fitting procedure in which the single road geometry describes a new road segment with the obstacle which is not described in the current map database. In one example, a polygonal principal curve algorithm or a Trace Clustering Algorithm (TC1) algorithm can be used. The digital map can be modified to include the new road, including possibly new intersections in the base map and any associated pointers or indices updated.

Flock Navigation

Next a flock control behavior is detailed. In one embodiment, a plurality of cars follow a leader car, who in turn is following a target vehicle or a target driving plan. The leader, or the first car in the group would automatically or manually take evasive actions to avoid an obstacle, and the information is transmitted via vehicle to vehicle communication such as DSRC to following vehicles, and the driving path of the entire flock is adjusted according to the obstacle. "Flocking" is the collective motion of a large number of self-propelled entities and is a collective animal behavior exhibited by many living beings such as birds, fish, bacteria, and insects. It is considered an emergent behavior arising from simple rules that are followed by individuals and does not involve any central coordination. The vehicle communications would identify vehicles traveling as a flock, and the vehicles perform distributed flocking operation by communication over the wireless network. One embodiment of the vehicle flocking process has the following structure:

```
initialise_vehicle_positions( )
LOOP
    place_vehicles( )
    move_all_vehicles_to_new_positions( )
END LOOP
```

Each of the vehicles rules works independently, so, for each vehicle, the process calculates how much it will get moved by each of the three rules, generating three velocity vectors. The three vectors to the vehicle's current velocity to work out its new velocity.

```
PROCEDURE move_all_vehicles_to_new_positions( )
    Vector v1, v2, v3
    Vehicle b
    FOR EACH VEHICLE b
```

-continued

```
        v1 = rule1(b)
        v2 = rule2(b)
        v3 = rule3(b)
        b.velocity = b.velocity + v1 + v2 + v3
        b.position = b.position + b.velocity
    END
```

The Vehicles Rules are discussed next. One embodiment simulates simple agents (vehicles) that are allowed to move according to a set of basic rules. The result is akin to a flock of birds, a school of fish, or a swarm of insects. In one embodiment, flocking behavior for each vehicle is controlled by three rules:

Separation—avoid crowding neighbors (short range repulsion)

Alignment—steer towards average heading of neighbors

Cohesion—steer towards average position of neighbors (long range attraction)

Rule 1: Vehicles try to go towards the center of mass of neighboring vehicles. The 'center of mass' is simply the average position of all the vehicles. Assume there are N vehicles, called b1, b2, . . . , bN. Also, the position of a vehicle b is denoted b.position. Then the 'center of mass' c of all N vehicles is given by: c=(b1.position+b2.position+ . . . +bN.position)/N However, the 'center of mass' is a property of the entire flock of vehicles; it is not something that would be considered by an individual vehicle. Each vehicle is moved toward its 'perceived center', which is the center of all the other vehicles, not including itself. Thus, for vehicle J ($1<=J<=N$), the perceived center pcJ is given by:

$$pcJ = (b1.position + b2.position + ... + bJ-1.position + bJ+1.position + ... + bN.position) / (N-1)$$

Having calculated the perceived center, the system moves the vehicle towards it. To move it 1% of the way towards the center this is given by (pcJ−bJ.position)/100 as:

```
PROCEDURE rule1(vehicle bJ)
    Vector pcJ
    FOR EACH VEHICLE b
        IF b != bJ THEN    pcJ = pcJ + b.position
    pcJ = pcJ /N−1
    RETURN (pcJ − bJ.position) / 100
```

Rule 2: Vehicles try to keep a small distance away from other objects (including other vehicles). The rule ensures vehicles don't collide into each other. If each vehicle within a defined small distance (say 100 units) of another vehicle, the vehicle is moved away. This is done by subtracting from a vector c the displacement of each vehicle which is near by.

```
PROCEDURE rule2(vehicle bJ)
    Vector c = 0;
    FOR EACH VEHICLE b
        IF b != bJ THEN
            IF |b.position − bJ.position| < 100 THEN    c = c − (b.position −
bJ.position)
    RETURN c
```

If two vehicles are near each other, they will be slightly steered away from each other, and at the next time step if they are still near each other they will be pushed further apart. Hence, the resultant repulsion takes the form of a smooth acceleration. If two vehicles are very close to each other it's probably because they have been driving very quickly towards each other, considering that their previous motion has also been restrained by this rule. Suddenly jerking them away from each other is not comfortable for passengers and instead, the processes have them slow down and accelerate away from each other until they are far enough apart for our liking.

Rule 3: Vehicles try to match velocity with near vehicles.

This is similar to Rule 1, however instead of averaging the positions of the other vehicles we average the velocities. We calculate a 'perceived velocity', pvJ, then add a small portion (about an eighth) to the vehicle's current velocity.

```
PROCEDURE rule3(vehicle bJ)
    Vector pvJ
    FOR EACH VEHICLE b
        IF b != bJ THEN
            pvJ = pvJ + b.velocity
        END IF
    END
    pvJ = pvJ / N-1
    RETURN (pvJ - bJ.velocity) / 8
END PROCEDURE
```

Additional rules is implemented as a new procedure returning a vector to be added to a vehicle's velocity.

Action of a crowd or traffic is discussed next. For example, to handle strong traffic.

```
PROCEDURE strong_traffic(Vehicle b)
    Vector traffic
    RETURN traffic
END PROCEDURE
```

This function returns the same value independent of the vehicle being examined; hence the entire flock will have the same push due to the traffic or crowd.

Limiting the speed of vehicles is discussed next. For a limiting speed vlim:

```
PROCEDURE limit_velocity(Vehicle b)
    Integer vlim
    Vector v
    IF |b.velocity| > vlim THEN
        b.velocity = (b.velocity / |b.velocity|) * vlim
    END IF
END PROCEDURE
```

This procedure creates a unit vector by dividing b.velocity by its magnitude, then multiplies this unit vector by vlim. The resulting velocity vector has the same direction as the original velocity but with magnitude vlim.

The procedure operates directly on b.velocity, rather than returning an offset vector. It is not used like the other rules; rather, this procedure is called after all the other rules have been applied and before calculating the new position, i.e. within the procedure move_all_vehicles_to_new_positions:

```
b.velocity = b.velocity + v1 + v2 + v3 + ...
limit_velocity(b)
b.position = b.position + b.velocity
```

Bounding the position is discussed next. In order to keep the flock within a certain zone so that they can drive out of them, but then slowly turn back, avoiding any harsh motions.

```
PROCEDURE bound_position(Vehicle b)
    Integer Xmin, Xmax, Ymin, Ymax, Zmin, Zmax
    Vector v
    IF b.position.x < Xmin THEN v.x = 10
        ELSE IF b.position.x > Xmax THEN v.x = -10
    IF b.position.y < Ymin THEN v.y = 10
        ELSE IF b.position.y > Ymax THEN v.y = -10
    IF b.position.z < Zmin THEN v.z = 10
        ELSE IF b.position.z > Zmax THEN v.z = -10
    RETURN v
```

Here of course the value 10 is an arbitrary amount to encourage them to drive in a particular direction.

During the course of flock control, one may want to break up the flock for various reasons. For example the introduction of a predator may cause the flock to scatter in all directions. The predator can be an object on an impending collision course with the flock. Scattering the flock can be done. Here the flock can disperse; they are not necessarily moving away from any particular object, but to break the cohesion (for example, the flock encounters a dangerously driven vehicle). Thus the system negates part of the influence of the vehicles rules.

```
PROCEDURE move_all_vehicles_to_new_positions( )
    FOR EACH VEHICLE b
        v1 = m1 * rule1(b)
        v2 = m2 * rule2(b)
        v3 = m3 * rule3(b)
        b.velocity = b.velocity + v1 + v2 + v3 + ...
        b.position = b.position + b.velocity
```

When the risk of collision arises, the process can make m1 negative to scatter the flock. Setting m1 to a positive value again will cause the flock to spontaneously re-form.

Tendency away from a particular place is handled next. If the flock is to continue the flocking behavior but to move away from a particular place or object (such as a car that appears to collide with the flock), then we need to move each vehicle individually away from that point. The calculation required is identical to that of moving towards a particular place, implemented above as tend_to_place; all that is required is a negative multiplier: v=−m*tend_to_place(b).

The vehicles can be organized into a V formation (sometimes called a skein) is the symmetric V-shaped formation for Drag Reduction and Fuel Saving where all the cars except the first drive in the upwash from the wingtip vortices of the car ahead. The upwash assists each car in supporting its own weight in flight, in the same way a glider can climb or maintain height indefinitely in rising air.

A flock of automatically driven motor vehicles is detailed next, each having the flock behavior. The motor vehicles of the flock establishes a target motor vehicle which will be used as a reference for flocking. The leading motor vehicle of the flock is established as the target motor vehicle by the motor vehicles of the flock. The target motor vehicle may be established before the motor vehicle start running in flock. In another embodiment, the first motor vehicle of the flock detects a preceding motor vehicle with the information from the radar or the CCD camera on the leading motor vehicle or flock leader, and automatically establishes the detected preceding motor vehicle as a new target motor vehicle. By successively changing new target motor vehicles in this manner, new motor vehicles may automatically be added to the flock. Even if a motor vehicle is incapable of communication between motor vehicles, that motor vehicle may be established as a target motor vehicle according to an algorithm described later on.

In one embodiment, the leading motor vehicle of the flock establishes a hypothetical target motor vehicle, and transmits items of information of the hypothetical target motor vehicle to the other motor vehicles of the flock which follow the flock leader through the inter-vehicular communications such as DSRC.

Each vehicle in the flock is responsible for generating a speed plan which governs the relationship between the position in which the motor vehicle runs and the speed at which the motor vehicle runs. The vehicles perform determining, based on the speed plan, a planned position to be reached from the present position of the motor vehicle after a predetermined time t, e.g., 1.5 seconds, and a planned speed of the motor vehicle at the planned position in the flock. According to this function, if the speed plan from the present position of the motor vehicle is generated such that the motor vehicle is to maintain the speed of 80 km/h, i.e., 22.2 m/sec., then the planned position to be reached after the predetermined time t, e.g., 1.5 seconds, is 33.3 m spaced from the present position down the running path B, and the planned speed at the planned position to be reached is 80 km/h.

The function as the predicted value calculating means serves to determine a predicted position and a predicted speed to be reached by the motor vehicle after the predetermined time t. The predicted position is calculated from the present position, i.e., the traveled distance, the present speed, and the present acceleration of the motor vehicle which are given from the communication module 1, and the predicted speed is calculated from the present speed and the present acceleration of the motor vehicle.

The speed/acceleration of the vehicle, based on which the predicted position and the predicted speed will be determined, is basically determined from the speedometer. The predicted position and the predicted speed are determined using the speed and the acceleration of the motor vehicle and GPS position.

A distance deviation, i.e., a position error, between a planned position to be reached by the motor vehicle after the predetermined time t based on the speed plan and the predicted position, described above, to be reached by the motor vehicle, and a speed deviation, i.e., a speed error, between a planned speed to be reached by the motor vehicle after the predetermined time t based on the speed plan and the predicted speed, described above, to be reached by the motor vehicle are determined. These deviations are calculated by subtractions. The target motor vehicle may be a flock leader. If, however, the target motor vehicle is not a flock leader, then the flock leader calculates a position, a speed, and an acceleration of the target motor vehicle using the laser radar, GPS, or triangulation of RF signals, for example. Based on the above control algorithm, the engine throttle valve opening, the transmission, and the brake of each of plural following motor vehicles are controlled to control the motor vehicles in a flock. The system detects the positional data of the preceding motor vehicle through inter-vehicular communications or the laser radar, and controls the following motor vehicle in the event that the preceding motor vehicle drops out of a normal control range of the vehicle flock control. Even when a motor vehicle drops out of the normal range of the vehicle flock control, the control algorithm controls a following motor vehicle to increase its inter-vehicular distance up to such a motor vehicle. Therefore, the vehicle platoon control will not be interrupted even when one or more motor vehicles drops out of the platoon. If it is known that a group of motor vehicles will travel in platoon or motor vehicles are counted at a tollgate or the like and the incremental count is indicated to each motor vehicle to let it recognize its position in the platoon, then it is possible to establish the position i for each of the motor vehicles before they travel in platoon. However, in order to handle a situation where another motor vehicle pulls in between motor vehicles running in platoon or another motor vehicle is added to a front or rear end of a platoon of motor vehicles, the process according to the present invention makes it possible for each of the motor vehicles running in flock to recognize its position relative to a target motor vehicle through inter-vehicular communications. There are two procedures available for each of the motor vehicles running in flock to recognize its position relative to a target motor vehicle. The first procedure is applicable to local inter-vehicular communications by which each of the motor vehicles of the flock can communicate with only those motor vehicles which run immediately in front of and behind the motor vehicle. If the flock leader of a flock is selected as a target motor vehicle, then the target motor vehicle transmits its own positional information i=0 to a next motor vehicle which immediately follows the target motor vehicle. The following motor vehicle adds 1 to i, producing its own positional information i=1, recognizes that it is the second motor vehicle from the target motor vehicle, and transmits its own positional information i=1 to a next motor vehicle which immediately follows the second motor vehicle. Having received the positional information i=1, the next immediately following motor vehicle adds 1 to i, producing its own positional information i=2, recognizes that it is the third motor vehicle from the target motor vehicle, and transmits its own positional information i=2 to a next motor vehicle which immediately follows the third motor vehicle. In this manner, each of the motor vehicles is able to recognize its position relative to the target motor vehicle with a means for counting its position and local inter-vehicular communications.

If a target motor vehicle is not the flock leader of a flock and the target motor vehicle and the flock leader cannot communicate with each other through inter-vehicular communications, then the flock leader sets its own positional information to i=1, and transmits the own positional information i=1 to a next motor vehicle which immediately follows the target motor vehicle.

According to the present invention, as described above, a longitudinal acceleration correcting quantity of each of the motor vehicles of a flock is determined on the basis of predicted deviations of a position and a speed that are predicted after a predetermined time, from a speed plan, and the speed of the motor vehicle is controlled on the basis of the determined longitudinal acceleration correcting quantity. Therefore, the motor vehicles can smoothly be controlled to run in flock along a running path on a road.

A longitudinal acceleration correcting quantity of a motor vehicle following a target motor vehicle is determined on the basis of an inter-vehicular distance between the following motor vehicle and the target motor vehicle and a speed difference there-between after a predetermined time, and the speed of the following motor vehicle is controlled on the basis of the determined longitudinal acceleration correcting quantity. Consequently, the following motor vehicle can automatically be driven smoothly along a miming path on a road while reliably keeping a proper inter-vehicular distance between the following motor vehicle and the target motor vehicle.

Since the system arrangements on a flock leader and a following motor vehicle of a flock are identical to each other, the flock leader and the following motor vehicle can automatically be driven in a manner to match them using slightly different software or program adaptations made therefor. Therefore, any one of the motor vehicles of the flock may become a flock reader or a following motor vehicle.

Each of following motor vehicles of a flock is not only controlled with respect to a flock leader, but also always monitors an inter-vehicular distance between itself and a preceding motor vehicle, so that it can increase the inter-vehicular distance even when a motor vehicle drops out of the flock. Therefore, it is not necessary to stop controlling the vehicle flock control when a motor vehicle drops out of the flock. Even when a motor vehicle drops out of a flock, the vehicle flock control system does not stop controlling the other motor vehicles to run in flock, and when the motor vehicle that has dropped out returns to the flock, the vehicle flock control system can continuously control the motor vehicles to run in flock. The vehicle flock control system allows different types of motor vehicles, such as trucks of different lengths, smaller automobiles, larger automobiles, etc., to be mixed in a flock, and can control those motor vehicles to run in flock. Accordingly, the vehicle flock control system according to the present invention is capable of stably controlling motor vehicles to run in flock on a road designed for motor vehicles to run automatically, and particularly of controlling the speeds of such motor vehicles smoothly.

Lane Marking Visibility Handling

In some embodiments, a lead vehicle identifies lane information that may include lane markings on the road, and the computer system may use one or more sensors to sense the lane markings For example, the computer system may use an image-capture device to capture images of the road and may detect the lane markings by analyzing the images for predetermined colors, shapes, and/or brightness levels that are similar to a predetermined color, shape, and/or brightness of the lane markings. As another example, the computer system may project a laser onto the road and may detect the lane markings by analyzing reflections off the road for an intensity that is similar to a predetermined intensity of a reflection off the lane markings. The computer system may estimate the location of the lane based on the sensed lane markings and control the vehicle to follow the lane. The vehicles behind the lead vehicle can then simply follow the lead vehicle as part of a flock.

At some point, the lead vehicle may determine that the lane information has become unavailable or unreliable. For example, severe fog may be present and severely affect the lane markings. In other examples, the vehicle may no longer be able to detect the lane markings on the road, the vehicle may detect contradictory lane markings on the road, the vehicle may no longer be able to determine a geographic location of the vehicle, and/or the vehicle may not be able to access a predetermined map of the road. Other examples are possible as well. In response to determining that the lane information has become unavailable or unreliable, the computer system may use at least one sensor to monitor at least one neighboring vehicle, such as a neighboring vehicle in a neighboring lane or a neighboring vehicle behind the vehicle that is part of the flock. The computer system may then control the vehicle to maintain a distance between the vehicle and the at least one neighboring vehicle to be at least a predetermined minimum distance and even if the vehicle is unable to rely on the lane information to estimate a location of the lane on the road, the vehicle may avoid colliding with the at least one neighboring vehicle.

In other embodiments, the lane information may include a geographic location of the vehicle and a predetermined map of the road. The computer system may determine the geographic location of the vehicle by, for example, querying a location server for the geographic location of the vehicle. Alternatively, if the predetermined map indicates a geographic location of at least two objects near the vehicle, the computer system may determine the geographic location of the vehicle by, for example, using a laser rangefinder or light detection and ranging (LIDAR) unit to estimate a distance from the vehicle to the at least two objects near the vehicle and determining the geographic location of the vehicle using triangulation. Other examples are possible as well. In any case, the computer system may then locate the geographic location of the vehicle on the predetermined map to determine a location of the lane relative to the geographic location of the vehicle.

In still other embodiments, the lane information may be derived from a leading vehicle that is in front of the vehicle in the lane and correlation with other information such as map data and independent lane analysis to prevent the blind-following-the blind situation. The computer system may estimate a path of the leading vehicle using, for example, a laser rangefinder and/or a LIDAR unit. Other examples are possible as well. Once the computer system has estimated the path of the leading vehicle, the computer system may estimate the location of the lane based on the estimated path. For example, the computer system may estimate the location of the lane to include the estimated path (e.g., extend by half of a predetermined lane width on either side of the estimated path). Other examples are possible as well.

In some embodiments, the computer system may maintain a predetermined threshold for the lane information, and the computer system may determine that the lane information has become unavailable or unreliable when the computer system detects that a confidence of the lane information (e.g., how confident the computer system is that the lane information is reliable) is below the predetermined threshold. In some embodiments, the computer system may additionally maintain a predetermined time period for the lane information, and the computer system may determine that the lane information has become unavailable or unreliable when the computer system detects that a confidence of the lane information is below the predetermined threshold for at least the predetermined amount of time.

Upon determining that the lane information has become unavailable or unreliable, the computer system may use at least one sensor to monitor at least one neighboring vehicle. The at least one neighboring vehicle may include, for example, a neighboring vehicle in a lane adjacent to the lane in which the vehicle is traveling. As another example, the at least one neighboring vehicle may include a neighboring vehicle behind the vehicle in the lane in which the vehicle is traveling. As still another example, the at least one neighboring vehicle may include a first neighboring vehicle and a second neighboring vehicle, each of which may be either in a lane adjacent to the lane in which the vehicle is traveling or behind the vehicle in the lane in which the vehicle is traveling. Other examples are possible as well.

When the lane information has become unavailable or unreliable, the computer system may control the vehicle to maintain a distance between the vehicle and the at least one neighboring vehicle to be at least a predetermined distance. The predetermined distance may be, for example, a distance determined to be a safe distance and/or a distance approximately equal to the difference between a predetermined lane width and a width of the vehicle. Other predetermined distances are possible as well.

In order to maintain the distance between the vehicle and the at least one neighboring vehicle to be at least the predetermined distance, the computer system may continuously or periodically use the at least one sensor on the vehicle to monitor the distance between the vehicle and the at least one neighboring vehicle. The computer system may monitor the distance between the vehicle and the at least one neighboring vehicle using, for example, a laser rangefinder and/or LIDAR unit. If the distance between the vehicle and the at least one neighboring vehicle becomes less than the predetermined distance, the computer system may move the vehicle away from the at least one neighboring vehicle in order to maintain the distance between the vehicle and the at least one neighboring vehicle to be at least the predetermined distance.

In some embodiments, in addition to maintaining the distance between the vehicle and the at least one neighboring vehicle to be at least the predetermined distance, the computer system may additionally maintain the distance between the vehicle and the at least one neighboring vehicle to be within a predetermined range of the predetermined distance. In these embodiments, if the distance between the vehicle and the at least one neighboring vehicle becomes too large (e.g., no longer within the predetermined range of the predetermined distance), the computer system may move the vehicle closer to the at least one neighboring vehicle. This may, for example, prevent the vehicle from drifting so far away from the neighboring vehicle that the vehicle drifts into a lane on the opposite side of the vehicle from the neighboring vehicle.

As noted above, in some embodiments the at least one vehicle may include a first neighboring vehicle and a second neighboring vehicle. In these embodiments, maintaining the distance between the vehicle and the at least one neighboring vehicle may involve maximizing both a first distance between the vehicle and the first neighboring vehicle and a second distance between the vehicle and the second neighboring vehicle (e.g., such that the vehicle remains approximately in the middle between the first neighboring vehicle and the second neighboring vehicle). Each of the first distance and the second distance may be at least the predetermined distance.

In some embodiments, in addition to maintaining the distance between the vehicle and the at least one neighboring vehicle to be at least the predetermined distance, the computer system may determine an updated estimated location of the lane. To this end, the computer system may use the at least one sensor to monitor at least a first distance to the at least one neighboring vehicle and a second distance to the at least one vehicle. Based on the first distance and the second distance, the computer system may determine a first relative position and a second relative position (e.g., relative to the vehicle) of the at least one neighboring vehicle. Based on the first relative position and the second relative position, the computer system may estimate a path for the at least one neighboring vehicle. The computer system may then use the estimated path to determine an updated estimated location of the lane. For example, in embodiments where the at least one neighboring vehicle is traveling in a lane adjacent to the lane in which the vehicle is traveling, the computer system may determine the estimated location of the lane to be substantially parallel to the estimated path (e.g., the lane may be centered on a path that is shifted from the estimated path by, e.g., a predetermined lane width and may extend by half of the predetermined lane width on either side of the path). As another example, in embodiments where the at least one neighboring vehicle is traveling behind the vehicle in the lane in which the vehicle is traveling, the computer system may determine the estimated location of the lane to be an extrapolation (e.g., with constant curvature) of the estimated path. Other examples are possible as well.

In some embodiments, the computer system may additionally use a speed sensor to monitor a speed of the at least one neighboring vehicle and may modify a speed of the vehicle to be less than the speed of the at least one neighboring vehicle. This may allow the vehicle to be passed by the at least one neighboring vehicle. Once the at least one neighboring vehicle has passed the vehicle, the at least one neighboring vehicle may become a leading vehicle, either in a lane adjacent to the lane in which the vehicle is traveling or a leading vehicle that is in front of the vehicle in the lane in which the vehicle is traveling, and the computer system may estimate the location of the lane of the road based on an estimated path of the leading vehicle, as described above.

In some embodiments, the computer system may begin to monitor the at least one neighboring vehicle only in response to determining that the lane information has become unavailable or unreliable. In these embodiments, prior to determining that the lane information has become unavailable or unreliable, the computer system may rely solely on the lane information to estimate the location of the lane. In other embodiments, however, the computer system may also monitor the at least one neighboring vehicle prior to determining that the lane information has become unavailable or unreliable. In these embodiments, the computer system may additionally use the distance to the at least one neighboring vehicle to estimate the location of the lane in which the vehicle is traveling. For example, if the at least one neighboring vehicle is traveling in a lane adjacent to the lane in which the vehicle is traveling, the computer system may determine that the lane does not extend to the at least one neighboring vehicle. As another example, if the at least one neighboring vehicle is traveling behind the vehicle in the lane in which the vehicle is traveling, the computer system may determine that the lane includes the at least one neighboring vehicle. Other examples are possible as well. Alternatively, in these embodiments, prior to determining that the lane information has become unavailable or unreliable, the computer system may simply use the distance to the at least one neighboring vehicle to avoid collisions with the at least one neighboring vehicle.

Further, in some embodiments, once the vehicle begins to monitor the at least one neighboring vehicle, the computer system may stop using the lane information to estimate the location of the lane in which the vehicle is traveling. In these embodiments, the computer system may rely solely on the distance to the at least one neighboring vehicle to avoid collisions with the at least one neighboring vehicle until the lane information becomes available or reliable. For example, the computer system may periodically attempt to obtain updated lane information. Once the computer system determines that the lane information has become available or reliable, the lane information has become available or reliable, the computer system may once again rely on the updated estimated location of the lane and less (or not at all) on the distance to the at least one neighboring vehicle. The computer system may determine that the updated lane information is reliable when, for example, the computer system determines that a confidence of the updated lane information is greater than a predetermined threshold. The predetermined threshold may be the same as or different than the predetermined threshold.

In an embodiment, a driver monitoring units can be configured to include for example, but not limited to, accelerometer, cameras, gyroscope, magnetometer, and the like sensors. In an embodiment, the accelerometer can include at least one accelerometer for measuring a lateral (sideways), longitudinal (forward and aft) and vertical acceleration in order to determine whether the driver is operating the vehicle in an unsafe or aggressive manner. For example, excessive lateral acceleration may be an indication that the driver is operating the vehicle at an excessive speed around a turn along a roadway. Furthermore, it is possible that the driver may be traveling at a speed well within the posted speed limit for that area of roadway. However, excessive lateral acceleration, defined herein as "hard turns," may be indicative of aggressive driving behavior by the driver and may contribute to excessive wear on tires and steering components as well as potentially causing the load such as a trailer to shift and potentially overturn.

As such, it can be seen that monitoring such driver behavior by providing feedback and recommendations to the driver during the occurrence of aggressive driving behavior such as hard turns can improve safety and reduce accidents. In addition, providing recommendations for such aggressive driver behavior can reduce wear and tear on the vehicle and ultimately reduce fleet maintenance costs as well as reduce insurance costs and identify at risk drivers and driving behavior to fleet managers.

In one aspect, the driver monitoring system may be in data communication with an on board diagnostic (OBD) system of the vehicle such as via a port. In some vehicle models, the driver monitoring system is in data communication with a controller area network (CAN) system (bus) to allow acquisition of certain driver and vehicle operating parameters including, but not limited to, vehicle speed such as via the speedometer, engine speed or throttle position such as via the tachometer, mileage such as via the odometer reading, seat belt status, condition of various vehicle systems including anti-lock-braking (ABS), turn signal, headlight, cruise control activation and a multitude of various other diagnostic parameters such as engine temperature, brake wear, and the like. The OBD or CAN allows for acquisition of the above-mentioned vehicle parameters for processing thereby and/or for subsequent transmission to the server 4106.

In an embodiment, the driver monitoring system may also include a GPS receiver (or other similar technology designed to track location) configured to track the location and directional movement of the driver in either real-time or over-time modes. As is well known in the art, GPS signals may be used to calculate the latitude and longitude of a driver as well as allowing for tracking of driver movement by inferring speed and direction from positional changes. Signals from GPS satellites also allow for calculating the elevation and, hence, vertical movement, of the driver.

In an embodiment, the driver monitoring unit may further include a mobile data terminal (MDT) mounted for observation and manipulation by the driver, such as near the vehicle dash. The MDT can be configured to include an operator interface such as a keypad, keyboard, touch screen, display screen, or any suitable user input device and may further include audio input capability such as a microphone to allow voice communications. The driver monitoring unit receives inputs from a number of internal and external sources. The OBD/CAN bus, which provides data from the vehicle's on-board diagnostic system, including engine performance data and system status information. A GPS receiver provides location information. The CDR, XLM, or accelerometers provide information regarding the vehicle's movement and driving conditions. Any number of other sensors, such as but not limited to, a seat belt sensor, proximity sensor, driver monitoring sensors, or cellular phone use sensors, also provide inputs to the driver monitoring system.

In an embodiment, the driver monitoring system may have any type of user interface, such as a screen capable of displaying messages to the vehicle's driver or passengers, and a keyboard, buttons or switches that allow for user input. The system or the user interface may have one or more status LEDs or other indicators to provide information regarding the status of the device's operation, power, communications, GPS lock, and the like. Additionally, the LEDs or other indicators may provide feedback to the driver when a driving violation occurs. Additionally, monitoring system may have a speaker and microphone integral to the device. In an embodiment, the monitoring system may be self-powered, such as by a battery, or powered by the vehicle's battery and/or power generating circuitry. Access to the vehicle's battery power may be by accessing the power available on the vehicle's OBD and/or CAN bus. The driver monitoring system may be self-orienting, which allows it to be mounted in any position, angle or orientation in the vehicle or on the dashboard. In an embodiment, the driver monitoring system determines a direction of gravity and a direction of driver movement and determines its orientation within the vehicle using this information. In order to provide more accurate measurements of driver behavior, the present invention filters gravitational effects out of the longitudinal, lateral and vertical acceleration measurements when the vehicle is on an incline or changes its horizontal surface orientation. Driver behavior can be monitored using the accelerometer, which preferably will be a tri-axial accelerometer. Acceleration is measured in at least one of lateral, longitudinal and/or vertical directions over a predetermined time period, which may be a period of seconds or minutes. An acceleration input signal is generated when a measured acceleration exceeds a predetermined threshold.

It will be understood that the present invention may be used for both fleets of vehicles and for individual drivers. For example, the driver monitoring system described herein may be used by insurance providers to monitor, recommend, provide feedback, and adjust insurance rates based on the driving. A private vehicle owner may also use the present invention to monitor the driver behavior and user of the vehicle. For example, a parent may use the system described herein to monitor a new driver or a teenage driver behavior.

An embodiment of the invention provides real-time recommendations, training, or other feedback to a driver while operating the vehicle. The recommendations are based upon observed operation of the vehicle and are intended to change and improve driver behavior by identifying improper or illegal operation of the vehicle. The driver monitoring system may identify aggressive driving violations. For example, based upon the inputs from an acceleration or CDR, aggressive driving behavior can be detected, such as exceeding acceleration thresholds in a lateral, longitudinal, or vertical direction, hard turns, hard acceleration or jackrabbit starts, hard braking, and/or hard vertical movement of the vehicle.

Further, in an embodiment, the sensor and camera described herein can be configured to communicate with the vehicle entertainment system. Typically, this functionality includes pre-installed software or a user-downloadable application from a network source (such as Apple's iTunes or Google's Android Market). The system functionality may include mapping functions, directions, landmark location, voice-control, and many other desirable features. When such mobile computing device is placed within the vehicle then a convenient vehicle entertainment system associated with the vehicle can be provided. In an embodiment, a remote switch can be used to initiate the vehicle entertainment software application by communicating with the cameras/sensors located in the vehicle and/or software residing on the mobile computing device. Remote switch described herein can include one of a number of well-known remote switches that uses wireless or wired technology to communicate with mobile computing device. For example, remote switch may include for example, but not limited to, a Bluetooth, RF, infrared, or other well-known wireless communication technology, or it may be connected via one or more wires to mobile computing device. The switch may be located on any vehicle interior surface, such as on a steering wheel, visor, dashboard, or any other convenient location.

In an embodiment, the cameras or sensors may be placed at any place in the vehicle, such as for example at four corners of the front windshield, in a way that it can directly capture the behavior parameters of the driver. For example, based on the driver gestures, the cameras can detect finger position to detect that driver is pointing at a particular object or vehicle and searches the internet for the vehicle. Further, in an embodiment, a flexible display film adhesively secured on the front windshield. The display can be used controlled by a computer to display info in a discrete way that may not take driver's eyes off the road and opposing vehicles. In an embodiment, at 4404, the driver monitoring unit 4102 can be configured to transmit the behavior parameters of the driver to the server 4106. In an embodiment, the driver behavior parameters described herein can include for example, but not limited to, vehicle speed, vehicle accelerations, driver location, seatbelt use, wireless device use, turn signal use, driver aggression, detection of CO2 vapor, detection of alcohol, driver seating position, time, and the like. In an embodiment, at 4406, the server 4106 can be configured to transmit the driver behavior parameters to one or more insurance providers. In an embodiment, at 4408, the server 4106 can be configured to analyze the driver behavior parameters and adjust the insurance rates for the driver. For example, if the driver is driving roughly by drinking alcohol then the insurance rate may get decreased. In an embodiment, at 4410, the server 4106 can be configured to match the driver behavior preferences with similar or substantially similar preferences of other drivers. The server 4104 can be configured to generate action recommendations best matching the behavior of the driver. In an embodiment at 4412, the server 4106 can be configured to provide the generated recommendations to the driver. Based on the driver behavior parameters the sever 4106 provides feedback and recommendations to the driver, such as to improve the driving skills. Further, in an embodiment, a flexible display film adhesively secured on the front windshield. The display can be used controlled by a computer to display info in a discrete way that may not take driver's eyes off the road and opposing vehicles. In an embodiment, at 4414, the server 4106 can be configured to frequently monitor the behavior parameters associated with the driver. Any changes in the behavior parameters can affect the overall system performance and the driver experience. The server 4106 can be configured to frequently monitor and dynamically update the insurance rate and action recommendations, which in turn helps the driver for effectively improving the driving skills.

In an embodiment, the driver behavior parameters can be used to provide customized recommendations to drivers by comparing the driver behavior parameters with other drivers who has similar or substantially similar behavior parameters. Unlike conventional system, the server 106 can be configured to adaptively generate action recommendations for the driver based on the behavior parameters. The server 106 can be configured to match the behavior parameters of the drivers to similar behavior parameters of the one or more drivers, such as to provide personalized action recommendations to the driver. In an embodiment, the recommendations can be filtered in advance of display. In an embodiment, filtered recommendations may be derived from the sources such as for example, but not limited to, those sources that have added the data within a specified time, from those sources that share specific similarities with the sources, those sources that have been preselected by the driver as relevant, those sources that are selected as friends or friends of friends, and the like, those sources that are determined to provide valuable reviews/ratings or are specifically declared to be experts within the system or by the driver, or those users that have entered at least a minimum amount of data into the system.

The system can monitor the driver behavior and uses the behavior data to match with the behavior data of other sources and provide action recommendations to the driver. For example, if the driver behavior parameter indicates that the user is driving very fast (such as 70 kmph) in school zone where the speed limits should be more than 30 kmph then the system can be configured to execute one or more rules and provide suggestions to the driver to slow down the speed. Rules can be derived from, for example, but not limited to, automatic generation machine learning, automatic generation using a generic algorithm, automatic generation using a neutral network, automatic generation using a rule inference system, data mining, generation using a preset list of recommendations, and/or a driver behavior. In an embodiment, the sever 106 can be configured to receive the recommendation rules such as unidirectional rules, bidirectional rules, generalized rules including multi-way rules, rules among items, rules among sets, rules among collections, rules with weight factors, rules with priorities, un-weighted and un-prioritized rules, and the like.

A method 4700 is used for selectively providing insurance information to a service provider, according to embodiments as disclosed herein. At step 4702, the driver behavior is monitored. The behavior data can include external parameters and/or internal parameters. In an embodiment, the driver behavior data/parameters described herein can include for example, but not limited to, vehicle speed, vehicle accelerations, driver location, seatbelt use, wireless device use, turn signal use, driver aggression, detection of ethanol vapor, driver seating position, time, and the like. In an embodiment, the behavior data can be over a period of hours, days, weeks, and so forth. In an embodiment, the behavior data gathering can be continuous, at predefined intervals, or at random intervals. In accordance with some aspects, data can be gathered while a vehicle is in operation and at other times (e.g., at two a.m. to determine where the vehicle is parked overnight). In an embodiment, a change to an insurance premium and/or an insurance coverage is prepared, at 4704. The change is based on one or more of the driver behavior data, wherein each item of driver behavior data can have a different weight assigned. For example, data gathered related to weather conditions might be given less weight than data gathered related to user distractions (e.g., passengers, use of a mobile device while vehicle is in operation, and so forth). In another example, excessive speed might be assigned a higher weight than data related to safety performance of the vehicle. As such, data with a higher weight can be given more consideration than data with a lower weight (e.g., data assigned a higher weight can have a greater impact on the cost of insurance). Thus, if the user is traveling at (or below) the speed limit and speed is assigned a greater weight, then the safe speed will tend to decrease (or remain constant) the cost of insurance.

In an embodiment, the driver is notified of the change, at 4706. The notification can be in any perceivable format. In an example, the notification is provided as a dashboard-mounted display. In another example, presenting the change can include displaying the modified cost of the insurance policy in a dashboard-mounted display and/or a heads-up display. In an embodiment, a service provider is notified of the change, at 708. At substantially the same time as notifying the service provider (or trusted third party) of the change, parameters taken into consideration (and associated weight) can also be provided. In such a manner, the service provider (or third party) can selectively further modify the cost of insurance, which can be communicated to the user though the vehicle display or through other means.

The service provider (or third party) might be provided the change information less often than the insurance cost change information is provided to the user. For example, the user can be provided the insurance cost change information dynamically and almost instantaneously with detection of one or more parameters that can influence the insurance cost. However, the insurance provider (or third party) might only be notified of the change after a specified interval (or based on other intervals). For example, insurance cost changes might be accumulated over a period of time (e.g., two weeks) and an average of the insurance cost changes might be supplied to insurance provider. In such a manner, the user has time to adjust parameters that tend to increase (or decrease) the cost of insurance, which allows the user to have more control over the cost of insurance.

In an embodiment, Vertical market specialization for insurance is provided where markets are defined based on granular aspects of coverage and presented to one or more insurance subsystems to obtain quotes for a coverage premium. Such specialization allows insurance companies to compete in more specific areas of insurance coverage, which allows for more accurate premium rates focused on the specific areas or one or more related scenarios. In addition, the granular aspects of coverage can be provided to one or more advertising systems in exchange for further lowered rates, if desired.

According to an example, an insurance market can be defined based on granular information received regarding an item, a related person, use of the item, etc. Based on the market, premium quotes can be obtained from one or more insurance subsystems related to one or more insurance brokers. In addition, rates can be decreased where the granular information can be provided to an advertising system, in one example. In this regard, targeted advertisements can additionally be presented to system related to requesting the insurance coverage. Policies can be automatically selected based on preferences, manually selected using an interface, and/or the like.

An exemplary system customizes insurance rates to correspond to behavior driver, according to embodiments as disclosed herein. In an embodiment, the server 4106 can be configured to maintain a database component 4802 including data related to different driver behaviors. Such leveraging from data banks enables insurance providers to bid in real time, and hence an owner and/or user of a vehicle can benefit from competition among various insurance providers, to obtain optimum rates. The server includes a rate adjustment component 4804 that in real time can determine the various rates from a plurality of insurance providers 4110 (1 to N, where N is an integer). In one particular aspect, a retrieval agent (not shown) associated with the rate adjustment component 4804 can pull insurance data from the insurance providers based on the contextual data supplied thereto. For example, such contextual data can be data records related to driver behavior, the vehicle 4102 (such as auto shop service records, current service status for the car, and the like), data related to the individual driver (such as health records, criminal records, shopping habits, and the like), data related to the environment (road condition, humidity, temperature, and the like) and data related to real time driving (frequency of braking, accelerating, intensity of such actions, and the like).

The retrieval agent (not shown) can pull data from the insurance providers 4110 and further publish such data to enable a rich interaction between the users on a display or a within a written communication environment. The retrieval agent can further generate an instance for a connection with the insurance providers. Accordingly, a connection instance can be employed by the rate adjustment component 4804 to store connection information such as the state of data conveyance, the data being conveyed, connection ID and the like. Such information can additionally be employed to monitor progress of data transfer to the written communication environment or display, for example. Accordingly, drivers/owners of motor vehicles can pull or receive data from the insurance providers 4110, wherein received data can be posted (e.g., displayed on a monitor) and the connection instance can be concurrently updated to reflect any successful and/or failed data retrievals. Thus, at any given moment the connection instance can include the most up-to-date version of data transferred between the motor vehicle and the insurance providers. In an embodiment, a switching component 4806 can be configured to automatically switch user/driver to an insurance provider/company that bids the best rate. Such switching component 4806 can employ interrupts both in hardware and/or software to conclude the switching from one insurance provider to another insurance provider. For example, the interrupt can convey receipt of a more optimal insurance rate or completion of a pull request to the insurance providers 4110 or that a configuration has changed. In one particular aspect, once an interrupt occurs, an operating system analyzes the state of the system and performs an action in accordance with the interrupt, such as a change of insurance provider, for example Such interrupts can be in form of asynchronous external events to the processor that can alter normal program flow. Moreover, the interrupts can usually require immediate attention from a processor(s) associated with the system. In one aspect, when an interrupt is detected, the system often interrupts all processing to attend to the interrupt, wherein the system can further save state of the processor and instruction pointers on related stacks.

According to a further aspect, the switching component 4804 can employ an interrupt dispatch table in memory, which can be accessed by the processor to identify a function that is to be called in response to a particular interrupt. For example, a function can accept a policy from an insurance provider, cancel an existing policy, and/or clear the interrupt for a variety of other reasons. The function can execute processes such as clearing the state of the interrupt, calling a driver function to check the state of an insurance policy and clearing, setting a bit, and the like.

The switching component 806 further includes an analyzer component 4902, which further employs threshold ranges and/or value(s) (e.g., pricing ranges for insurance policies, terms of the insurance policy, and the like) according to a further aspect of the present invention. The analyzer component 4902 can be configured to compare a received value for insurance coverage to the predetermined thresholds, which can be designated by an owner/driver. Accordingly, the analyzer component 902 can determine if the received insurance coverage policies are within the desired range as specified by a user an "accept" or "reject", and/or further create a hierarchy from "low" to "high" based on criteria designated by the user (e.g., price of the insurance policy, terms of the insurance policy, and the like).

According to a further aspect, the analyzer component 4902 can further interact with a rule engine component 4904. For example, a rule can be applied to define and/or implement a desired evaluation method for an insurance policy. It is to be appreciated that the rule-based implementation can automatically and/or dynamically define and implement an evaluation scheme of the insurance policies provided. Accordingly, the rule-based implementation can evaluate an insurance policy by employing a predefined and/or programmed rule(s) based upon any desired criteria (e.g., criteria affecting an insurance policy such as duration of the policy, number of drivers covered, type of risks covered, and the like.).

In a related example, a user can establish a rule that can implement an evaluation based upon a preferred hierarchy (e.g., weight) of criteria that affects the insurance policy. For example, the rule can be constructed to evaluate the criteria based upon predetermined thresholds, wherein if such criteria does not comply with set thresholds, the system can further evaluate another criteria or attribute(s) to validate the status (e.g., "accept" or "reject" the insurance bid and operate the switching component based thereon). It is to be appreciated that any of the attributes utilized in accordance with the subject invention can be programmed into a rule-based implementation scheme.

A method for customizing insurance rates of a driver in real time is discussed next. The method presents information related to a real-time insurance rate, according to embodiments as described herein. In an embodiment, at 5102, Metadata can be collected pertaining to real-time operation of a vehicle and at least a portion of the metadata can be evaluated, as shown at 5104. The metadata described herein can include driver behavior data, contextual information, driver history, and real-time driving information that relates to operation of a driver and vehicle, and the like. Based upon a result of the evaluation, there can be calculation a real-time insurance rate, such as shown at 5106. In an embodiment, at 5108, determination can be made on how to present the calculated rate. For example, the determination can be if the rate should be shown on a center console or a heads-up display. A determination can also be made on how to display data (e.g., if a numerical rate should be disclosed or a color element should be lit). Additionally, a determination can be made on other data to disclose, such as safety, environment impact, cost of operating vehicle, a target speed, group rank, and the like. The determined rate and other determined data can be presented through a display, such as shown at 5110. Thus, the determined rate is presented upon a display viewable to the driver of the vehicle. In an embodiment, at 5112, the method 5100 includes determining if feedback should be presented to the user. The feedback can be supplied in real-time as well as be a collective summary presented after a driving session is complete. If no feedback should be presented, then the method 5100 can end at 5114. In one instance, if there is a new driver attempting to obtain a full drivers license (e.g., teenage driver) or newer driver, then the check 5112 can determine feedback should be automatically provided. In another embodiment, an operator can be solicited on if feedback should be presented depending on a response the method 5100 can end or continue.

Operation of the vehicle and driver can be evaluated at 5116, which can occur though different embodiments. As a user operates a vehicle, metadata can be collected and evaluated in real-time. In an alternative embodiment, data can be collected, but evaluation does not occur until the check 5112 determines feedback should be presented. At 5118, there can be determining feedback for suggesting future driving actions for the operator to perform in future driving to lower the insurance rate. The method 5100 can include presenting the feedback (e.g., through the display, through a printout, transferring feedback as part of e-mail or a text message, etc.) at 5120. The feedback can be directly related to a driving session as well as is an aggregate analysis of overall driving performance (e.g., over multiple driving sessions).

In an embodiment, at 5202, an on-board monitoring system (such as driver monitoring unit) 4102 is installed in a vehicle to facilitate the collection of real-time data from the vehicle and forwarding of the real-time data to an insurance provider. At 5204, the on-board monitoring system can be associated with the on-board data/diagnostic control units and system(s) incorporated into the vehicle. The on-board data/diagnostic control units and system(s) can include the vehicles engine control unit/module (ECU/ECM), transmission control unit (TCU), power train control unit (PCU), on-board diagnostics (OBD), sensors and processors associated with the transmission system, and other aspects of the vehicle allowing the on-board monitoring system to gather sufficient data from the vehicle for a determination of how the vehicle is being driven to be made. The on-board monitoring system can be communicatively coupled by hard wiring to the on-board diagnostic system(s) or the systems can be communicatively associated using wireless technologies. In an embodiment, at 5206, a mobile device (e.g., a cell phone) can be associated with the onboard monitoring system where the mobile device can facilitate communication between the on-board monitoring systems with a remote insurance provider system. The mobile device provides identification information to the on-board monitoring system to be processed by the on-board monitoring system or forwarded an insurance provider system to enable identification of the driver. In an embodiment, at 5208, communications are established between the on-board monitoring system and the mobile device with the remote insurance provider system. In one embodiment it is envisaged that the on-board monitoring system and the insurance provider system are owned and operated by the same insurance company. However, the system could be less restricted whereby the insurance provider system is accessible by a plurality of insurance companies with the operator of the on-board monitoring system, e.g., the driver of the vehicle to which the on-board monitoring system is attached, choosing from the plurality of insurance providers available for their particular base coverage. In such an embodiment, upon startup of the system the insurance provider system can default to the insurance company providing the base coverage and the operator can select from other insurance companies as they require. Over time, as usage of the on-board monitoring system continues, at 5210, there is a likelihood that various aspects of the system might need to be updated or replaced, e.g., software update, hardware updates, etc., where the updates might be required for an individual insurance company system or to allow the on-board monitoring system to function with one or more other insurance company systems. Hardware updates may involve replacement of a piece of hardware with another, while software updates can be conducted by connecting the mobile device and/or the on-board monitoring system to the internet and downloading the software from a company website hosted thereon. Alternatively, the software upgrade can be transmitted to the mobile device or the on-board monitoring system by wireless means. As a further alternative the updates can be conferred to the mobile device or the on-board monitoring system by means of a plug-in module or the like, which can be left attached to the respective device or the software can be downloaded there from.

Monitoring can employ components of an on-board monitoring system, mobile device components, e.g., cell phone system, or any other system components associated with monitoring the vehicle as it is being driven. Such components can include a global positioning system (GPS) to determine the location of the vehicle at any given time, such a GPS can be located in a cell phone, as part of the on-board monitoring system, or an external system coupled to the monitoring system/cell phone—such an external system being an OEM or after sales GPS associated with the vehicle to be/being driven. A video data stream can be gathered from a video camera coupled to the on-board monitoring system recording the road conditions, etc. throughout the journey. Information can also be gathered from monitoring/control system(s) that are integral to the vehicle, e.g., the vehicle's engine control unit/module (ECU/ECM) that monitors various sensors located throughout the engine, fuel and exhaust systems, etc. In an embodiment, at 5304, the dynamically gathered data (or driver behavior data) is transmitted to an insurance evaluation system. In an embodiment, at 5306, the gathered data is analyzed. Such analysis can involve identifying the route taken by the driver, the speed driven, time of day the journey was undertaken, weather conditions during the journey, other road traffic, did the user use their cell phone during the journey?, and the like. In an embodiment, at 5308, the gathered data is assessed from which an insurance rate(s) can be determined. For example, if the driver drove above the speed limit then an appropriate determination could be to increase the insurance premium. In an embodiment, at 5310, the driver can be informed of the newly determined insurance rate. Any suitable device can be employed such as informing the user by cell phone, a display device associated with the on-board monitoring system, or another device associated with the vehicle. The information can be conveyed in a variety of ways, including a text message, a verbal message, graphical presentation, change of light emitting diodes (LED's) on a display unit, a HUD, etc. At 5312, the driver can continue to drive the vehicle whereby the method can return to 5302 where the data gathering is commenced once more. Alternatively, in an embodiment, at 5312, the driver may complete their journey and data gathering and analysis is completed. In an embodiment, at 5314 the driver can be presented with new insurance rates based upon the data gathered while they were driving the vehicle. The new insurance rates can be delivered and presented to the driver by any suitable means, for example the new insurance rates and any pertinent information can be forwarded and presented to the driver via a HUD employed as part of the real time data gathering system. By employing a HUD instantaneous notifications regarding a change in the driver's insurance policy can be presented while mitigating driver distractions {e.g., line of sight remains substantially unchanged). Alternatively, the on-board monitoring system can be used, or a remote computer/presentation device coupled to the real time data gathering system where the information is forwarded to the driver via, e.g., email. In another embodiment, the driver can access a website, hosted by a respective insurance company, where the driver can view their respective rates/gathered information/analysis system, etc. Further, traditional means of communication such as a letter can be used to forward the insurance information to the driver.

Cameras can be used to capture traffic information, according to embodiments as disclosed herein. In an embodiment, at 5402, the method 5400 includes mounting cameras on the car to monitor the traffic information. For example, the car may include cameras mounted to capture views in the rearward, downward, and the like directions, on the upper surface at the leading end of the front portion thereof. The position for mounting the cameras is not limited to the left side, right side, upper surface, front side, back side, and the like. For example, if the car has a left side steering wheel, the camera may be mounted on a right upper surface at a leading end of the front portion of the car. The cameras may have an angle of view of about 60, 90, 180, and 360 degree. With the construction, since the camera is mounted for a view in the rearward and downward directions on the front portion of the car, it can capture a wide area of the surface of the road in the vicinity of the driver's car, and an area in the vicinity of the left front wheel. Furthermore, the camera can also capture a part of the body of the car in the vicinity of the front wheel. Thereby, the relation between the car and the surface of the road can be recorded. In an example, the cameras can be configured to capture images of the road views including potential collision events such as how close car is following car in front, how often brake is used in period of time, hard brakes count more to reduce driver rating, how frequently does car come close to objects and obstructions (such as trees, cars on the other direction and cars in same direction) while moving. In an embodiment, at 5404, the method 5400 includes receiving the recorded information from the camera and use image processing techniques to process the information. For example, the system uses image processing techniques to determine potential collision events such as how close car is following car in front, how often brake is used in period of time, hard brakes count more to reduce driver rating, how frequently does car come close to objects and obstructions (such as trees, cars on the other direction and cars in same direction) while moving. In an embodiment, at 5502, the method 5500 includes mounting cameras on the car to monitor the driver behavior. The position for mounting the cameras is not limited to the left side, right side, upper surface, front side, back side, and the like. The cameras may have an angle of view of about 60, 90, 180, and 360 degree. For example, the camera can capture driver behavior such as for example, but not limited to, images of texting and use of phone while driving, speech of driver shouting or cursing at other drivers or other occupants, indications of intoxication, sleepiness, alcohol level, mood, aggressiveness, and the like. In an embodiment, at 5504, the method 5500 includes receiving the recorded information from the camera and use image processing techniques and voice reorganization techniques to process the information. For example, the system uses image processing techniques to determine the driver activity such as whether the driver is using mobile phone while driving. In another example, the system uses voice recognition techniques to determine the use voice, text, aggressiveness, and the like. In an embodiment, the item-centric approach determines that many drivers having similar behavior and the driver who performs activity-A will also perform activity-B. This has proven to be fairly effective. On the other hand, many insurance providers interact with drivers online/offline. Such interaction can produce a stream of contextual information that recommendation engines can use. Early systems were batch oriented and computed recommendations in advance for each driver. Thus, they could not always react to a driver's most recent behavior. Recommendation engines work by trying to establish a statistical relationship between drivers and activities associated with there behavior. The system establishes these relationships via information about driver's behavior from vehicle owner, monitoring devices, sensors, and the like. In an embodiment, the recommender systems collect data via APIs, insurance application, insurance databases, and the like sources. The insurance sources can be available through social networks, ad hoc and marketing networks, and other external sources. For example, data can be obtained from insurance sites, insurance providers, driver insurance history, and search engines. All this enables recommendation engines to take a more holistic view of the driver. The recommendation engine can recommend different insurance products that save money for the driver, or alternatively can even recommend different insurance companies to save money. Using greater amounts of data lets the engines find connections that might otherwise go unnoticed, which yields better suggestions. This also sometimes requires recommendation systems to use complex big-data analysis techniques. Online public profiles and preference listings on social networking sites such as Facebook add useful data.

Most recommendation engines use complex algorithms to analyze driver behavior and suggest recommended activities that employ personalized collaborative filtering, which use multiple agents or data sources to identify behavior patterns and draw conclusions. This approach helps determine that numerous drivers who have same or similar type of behavior in the past may have to perform one or more similar activities in the future. Many systems use expert adaptive approaches. These techniques create new sets of suggestions, analyze their performance, and adjust the recommendation pattern for similar behavior of drivers. This lets systems adapt quickly to new trends and behaviors. Rules-based systems enable businesses to establish rules that optimize recommendation performance.

Figure 14:
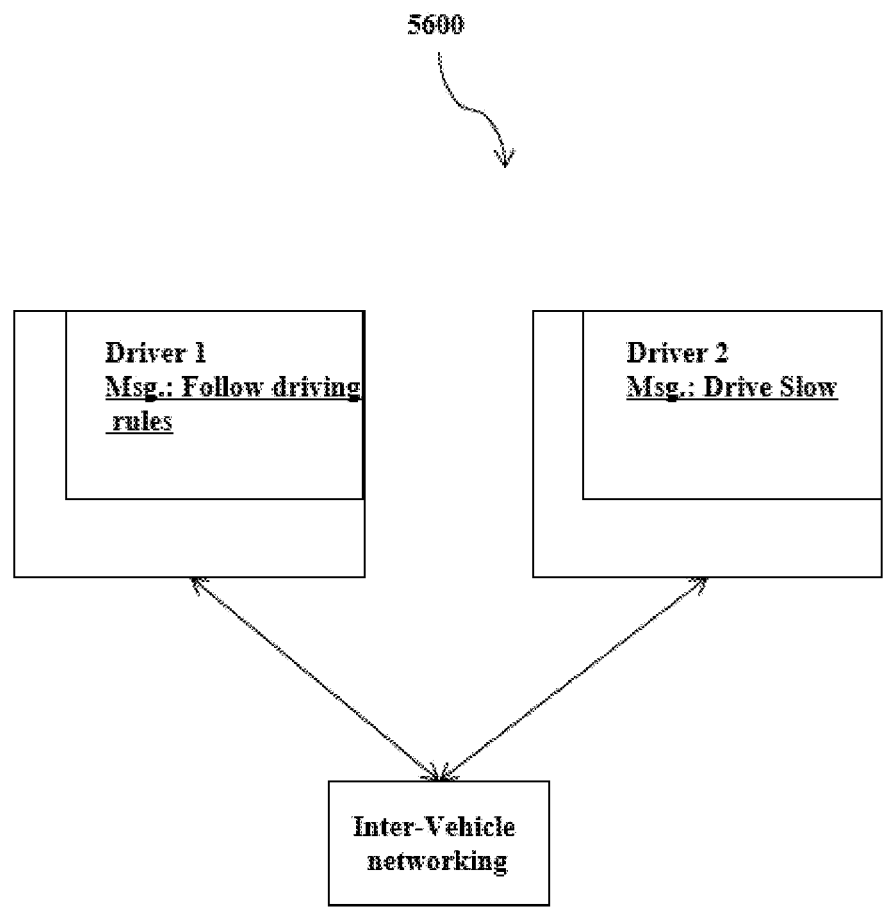
FIG. 14 shows an exemplary vehicle coordination system.

FIG. 14 is a diagram 5600 illustrates generally, a first vehicle program communicating with a second vehicle program through an Inter-Vehicle networking, according to embodiments as disclosed herein. In an embodiment, the system develops inter-vehicular networking, computing, transceivers, and sensing technologies in the vehicles. Such vehicles have embedded computers, GPS receivers, short-range wireless network interfaces, and potentially access to in-car sensors and the Internet. Furthermore, they can interact with road-side wireless sensor networks and sensors embedded in other vehicles. These capabilities can be leveraged into distributed computing and sensing applications over vehicular networks for safer driving, dynamic route planning, mobile sensing, or in-vehicle entertainment. The system can include vehicular-specific network protocols, middleware platforms, and security mechanisms to process the data. As shown in FIG. 14, a first driver operating a vehicle observes a second driver operating a vehicle within his visual range and wants to send a message to the second driver. The vehicle can include identifying information that is visually ascertainable such as the model, vehicle color, number of doors, license plate number and state. The vehicle may include additional information that is only ascertainable from up close or at certain angles, or via certain technologies, such as a roof top identification number, vehicle identification number, taxi badge number, Bluetooth, or RFID code, and the like. In an embodiment, a sender having access to the vehicle monitoring device and viewing a second vehicle desires to contact the driver of the second vehicle. In one embodiment, in case of an accident as detected by an accelerometer or airbag deployment, both vehicles automatically exchange insurance information and the drivers simply confirm and signs to accept. In another embodiment, in case of a hit-and-run, the vehicle computer would automatically capture insurance information from the other vehicle and store all parameters arising from the accident for accident investigator's review. In another embodiment, if one vehicle detects that the other vehicle has a low insurance rating, the vehicle automatically enters a defensive driving mode around that vehicle. As best shown in FIG. 16, the sender initiates communication via a telephone or handheld computer or vehicle monitoring device and accesses the interface to the inter-vehicle networking service and database. The sender can select "send message" from the graphical or audio menu to send message or directly communicate with the driver of the second vehicle.

For example, the sender can directly communicate with the driver using the inter-vehicle networking or the sender can choose from a table of messages that can be sent to the driver using the inter-vehicle networking. For example, the message can take the form of voice, audio, video, or other data which can be converted to a digital signal and sent to any communications terminal. The inter-vehicle networking database receives the message or encrypted message and reconstructs the message, including the address information. The inter-vehicle networking then separates out the address information including such as for example, but not limited to, license plate number, vehicle identification number, and the like.

In an embodiment, the message may include a return address for the sender, so that a reply can be returned merely by hitting the "reply to" or "call back" button on the message. One skilled in the art would also recognize that the message could be sent anonymously or by a non-returnable address. Alternatively, the message could be a general broadcast sent by a police officer or other official sending a warning message to speeders or an informational message such as "road closed ahead" or other message.

In this case, the transceiver can be a WiMAX system. In another embodiment, the transceiver can be a meshed 802 protocol network configuration with a constantly morphing mobile mesh network that helps drivers avoid accidents, identify traffic jams miles before they encounter them, and act as a relay point for Internet access. In one embodiment, the mesh network can be the ZigBee mesh network. In another embodiment, the mesh network can be a modified Wi-Fi protocol called 802.11p standard for allowing data exchange between moving vehicles in the 5.9 GHz band. 802.11p operates in the 5.835-5.925 GHz range, divided into 7 channels of 10 MHz each. The standard defines mechanisms that allow IEEE 802.11™ technology to be used in high speed radio environments typical of cars and trucks. In these environments, the 802.11p enhancements to the previous standards enable robust and reliable car-to-car and car-to-curb communications by addressing challenges such as extreme Doppler shifts, rapidly changing multipath conditions, and the need to quickly establish a link and exchange data in very short times (less than 100 ms). Further enhancements are defined to support other higher layer protocols that are designed for the vehicular environment, such as the set of IEEE1609™ standards for Wireless Access in Vehicular Environments (WAVE). 802.11p supports Intelligent Transportation Systems (ITS) applications such as cooperative safety, traffic and accident control, intersection collision avoidance, and emergency warning.

One variation of 802.11p is called the Dedicated Short Range Communications (DSRC), a U.S. Department of Transportation project as well as the name of the 5.9 GHz frequency band allocated for the ITS communications. More information on the 802.11p standard can be obtained from the IEEE. DSRC itself is not a mesh. It's a broadcast, so it only reaches vehicles within range. Meshing requires a lot more sophistication. There's a routing aspect to it, relaying messages to other nodes. DSRC is much simpler.

One embodiment uses high-powered, heavily encrypted Wi-Fi that establishes point-to-point connections between cars within a half-mile radius. Those connections are used to communicate vital information between vehicles, either triggering alerts to the driver or interpreted by the vehicle's computer. An intelligent car slamming on its brakes could communicate to all of the vehicles behind it that it's coming to rapid halt, giving the driver that much more warning that he too needs to hit the brakes.

But because these cars are networked—the car in front of one vehicle is connected to the car in front it and so forth—in a distributed mesh, an intelligent vehicle can know if cars miles down the road are slamming on their brakes, alerting the driver to potential traffic jams. Given enough vehicles with the technology, individual cars become nodes in a constantly changing, self-aware network that can not only monitor what's going on in the immediate vicinity, but across a citywide traffic grid.

In one embodiment, the processor receives travel routes and sensor data from adjacent vehicles, such information is then used for preparing vehicular brakes for a detected turn or an anticipated turn from adjacent vehicles. The travel routes can be transmitted over a vehicular Wi-Fi system that sends protected information to nearby vehicles equipped with Wi-Fi or Bluetooth or ZigBee nodes. In one embodiment, a mesh-network is formed with Wi-Fi transceivers, wherein each vehicle is given a temporary ID in each vehicular block, similar to a cellular block where vehicles can join or leave the vehicular block. Once the vehicle joins a group, travel routes and sensor data is transferred among vehicles in a group. Once travel routes are shared, the processor can determine potential or desired actions from the adjacent vehicles and adjust appropriately. For example, if the car in front of the vehicle is about to make a turn, the system prepares the brakes and gently tugs the driver's seat belt to give the drive notice that the car in front is about to slow down. In another example, if the processor detects that the driver is about to make a lane change to the left based on sensor data and acceleration pedal actuation, but if the processor detects that the vehicle behind in the desired lane is also speeding up, the system can warn the driver and disengage the lane change to avoid the accident. Thus, the processor receives travel routes and sensor data from adjacent vehicles and notifying the driver of a detected turn or an anticipated turn from adjacent vehicles. The processor receives travel routes and sensor data from adjacent vehicles and optimizes group vehicular speed to improve fuel efficiency. The processor receives travel routes and sensor data from adjacent vehicles and sequences red light(s) to optimize fuel efficiency. The processor notifies the driver of driving behaviors from other drivers at a predetermined location. The processor switches turn signals and brakes using a predetermined protocol to reduce insurance premium for the driver. The processor warns the driver to avoid driving in a predetermined pattern, driving during a predetermined time, driving in a predetermined area, or parking in a predetermined area to reduce insurance premium for the driver. The processor sends driver behavior data to an insurer, including at least one of: vehicle speed, vehicle accelerations, vehicle location, seatbelt use, wireless device use, turn signal use, detection of ethanol vapor, driver seating position, and time.

The various systems described above may be used by the computer to operate the vehicle and maneuver from one location to another. For example, a user may enter destination information into the navigation system, either manually or audibly. The vehicle may determine its location to a few inches based on a combination of the GPS receiver data, the sensor data, as well as the detailed map information. In response, the navigation system may generate a route between the present location of the vehicle and the destination.

When the driver is ready to relinquish some level of control to the autonomous driving computer, the user may activate the computer. The computer may be activated, for example, by pressing a button or by manipulating a lever such as gear shifter. Rather than taking control immediately, the computer may scan the surroundings and determine whether there are any obstacles or objects in the immediate vicinity which may prohibit or reduce the ability of the vehicle to avoid a collision. In this regard, the computer may require that the driver continue controlling the vehicle manually or with some level of control (such as the steering or acceleration) before entering into a fully autonomous mode.

Once the vehicle is able to maneuver safely without the assistance of the driver, the vehicle may become fully autonomous and continue to the destination. The driver may continue to assist the vehicle by controlling, for example, steering or whether the vehicle changes lanes, or the driver may take control of the vehicle immediately in the event of an emergency.

The vehicle may continuously use the sensor data to identify objects, such as traffic signals, people, other vehicles, and other objects, in order to maneuver the vehicle to the destination and reduce the likelihood of a collision. The vehicle may use the map data to determine where traffic signals or other objects should appear and take actions, for example, by signaling turns or changing lanes. Once the vehicle has arrived at the destination, the vehicle may provide audible or visual cues to the driver. For example, by displaying "You have arrived" on one or more of the electronic displays.

The vehicle may be only partially autonomous. For example, the driver may select to control one or more of the following: steering, acceleration, braking, and emergency braking.

The vehicle may also have one or more user interfaces that allow the driver to reflect the driver's driving a style. For example, the vehicle may include a dial which controls the level of risk or aggressiveness with which a driver would like the computer to use when controlling the vehicle. For example, a more aggressive driver may want to change lanes more often to pass cars, drive in the left lane on a highway, maneuver the vehicle closer to the surrounding vehicles, and drive faster than less aggressive drivers. A less aggressive driver may prefer for the vehicle to take more conservative actions, such as somewhat at or below the speed limit, avoiding congested highways, or avoiding populated areas in order to increase the level of safety. By manipulating the dial, the thresholds used by the computer to calculate whether to pass another car, drive closer to other vehicles, increase speed and the like may change. In other words, changing the dial may affect a number of different settings used by the computer during its decision making processes. A driver may also be permitted, via the user interface, to change individual settings that relate to the driver's preferences. In one embodiment, insurance rates for the driver or vehicle may be based on the style of the driving selected by the driver.

Aggressiveness settings may also be modified to reflect the type of vehicle and its passengers and cargo. For example, if an autonomous truck is transporting dangerous cargo (e.g., chemicals or flammable liquids), its aggressiveness settings may be less aggressive than a car carrying a single driver—even if the aggressive dials of both such a truck and car are set to "high." Moreover, trucks traveling across long distances over narrow, unpaved, rugged or icy terrain or vehicles may be placed in a more conservative mode in order reduce the likelihood of a collision or other incident.

In another example, the vehicle may include sport and non-sport modes which the user may select or deselect in order to change the aggressiveness of the ride. By way of example, while in "sport mode", the vehicle may navigate through turns at the maximum speed that is safe, whereas in "non-sport mode", the vehicle may navigate through turns at the maximum speed which results in g-forces that are relatively imperceptible by the passengers in the car.

The vehicle's characteristics may also be adjusted based on whether the driver or the computer is in control of the vehicle. For example, when a person is driving manually the suspension may be made fairly stiff so that the person may "feel" the road and thus drive more responsively or comfortably, while, when the computer is driving, the suspension may be made such softer so as to save energy and make for a more comfortable ride for passengers. The adjustment can be done by hand as in the following:

1. A method to control the car using hand gestures.
2. The method of claim 1, further comprising detecting a hand movement as mouse movement or mouse clicks to control the vehicle.
3. The method of claim 1, further comprising controlling a car window position using an arm gesture and finger gesture and exiting by forming a fist.
4. The method of claim 1, further comprising controlling a seat position using an arm gesture and a figure gesture, comprising moving the seat as specified by an arm angular movement.
5. The method of claim 1, further comprising unlocking a hood or a trunk using an arm gesture and a figure gesture, wherein to open the trunk a driver makes a right angular movement and an opposite movement for unlocking the hood.
6. The method of claim 1, further comprising controlling temperature of a driver and front passenger seats using an arm gesture and a finger gesture, wherein the number of fingers affect a seat temperature.
7. The method of claim 1, further comprising performing a left arm gesture based navigation control for a car.
8. The method of claim 1, further comprising activating a positioning system and selecting start and destination using gestures.
9. The method of claim 1, further comprising controlling a mirror position with gesture based control.
10. The method of claim 1, further comprising controlling music using hand gesture.
11. The method of claim 1, further comprising controlling vehicle temperature with a hand gesture.
12. The method of claim 1, further comprising controlling sound volume using a gesture.
13. The method of claim 1, further comprising controlling sun roof opening and closure using a gesture.
14. The method of claim 1, further comprising controlling wind shield wipers with a gesture.
15. The method of claim 1, further comprising controlling operation of a rear view mirror.
16. The method of claim 1, further comprising gesturing on a steering wheel to make calls, receive and respond to texts, launch apps, get turn-by-turn directions, find the nearest other local businesses, play music, or search the Internet while driving.
17. The method of claim 1, further comprising controlling an air conditioning system.
18. The method of claim 1, further comprising recognizing a combination of gestures to create a custom gesture control.
19. The method of claim 1, further comprising ultrasonic sensors to detect gestures.
20. The method of claim 1, further comprising rendering a display or sound or tactile feedback for a detected gesture.

Augmented Reality/Virtual Reality Sports Gaming

FIG. 15 shows an exemplary 360 degree camera on a helmet, for example, for augmenting reality of games. Using augmented reality, various ways may exist for a user to "participate" in a live event. Generally, augmented reality refers to a presentation of a real world environment augmented with computer-generated data (such as sound, video, graphics or other data). In some embodiments, augmented reality, implemented in conjunction with a live event, may allow a user to control a virtual object that appears to compete or otherwise interact with the participants of the live event. For example, an end user device, such as a mobile phone, tablet computer, laptop computer, or gaming console may be used to present a live video feed of an event to a user. This live video feed may be video of an event that is occurring in real-time, meaning the live event is substantially concurrently with the presentation to the user (for example, buffering, processing, and transmission of the video feed may result in a delay anywhere from less than a second to several minutes). The presentation of the live event may be augmented to contain one or more virtual objects that can be at least partially controlled by the user. For instance, if the live event is a stock car race, the user may be able to drive a virtual car displayed on the end user device to simulate driving in the live event among the actual racers. As such, the user may be able to virtually "compete" against the other drivers in the race. The virtual object, in this example a car, may be of a similar size and shape to the real cars of the video feed. The user may be able to control the virtual car to race against the real cars present in the video feed. The real cars appearing in the video feed may affect the virtual object. For example, the virtual object may not be allowed to virtually move through a real car on the augmented display, rather the user may need to drive the virtual object around the real cars. Besides racing, similar principles may be applied to other forms of live events; for example, track and field events (e.g., discus, running events, the hammer toss, pole vaulting), triathlons, motorbike events, monster truck racing, or any other form of event that a user could virtually participate in against the actual participants in the live event. In some embodiments, a user may be able to virtually replay and participate in past portions of a live event. A user that is observing a live event may desire to attempt to retry an occurrence that happened during the live event. While viewing the live event, the user may be presented with or permitted to select an occurrence that happened in the course of the live event and replay it such that the user's input affects the outcome of at least that portion of the virtualized live event. Using a baseball game as an example, with runners on first and third, two outs, and the count being two balls and two strikes, the pitcher may throw a splitter, successfully striking out the batter with a pitch in the dirt. The inning may end and the game may continue. The user may desire to replay this unsuccessful at-bat with himself controlling the batter during the commercial break. As such, via an end user device, the user may be able to indicate the portion of the game he wishes to replay (e.g., the last at-bat). Game facts from the live event may be used to virtually recreate this at-bat for the user. For instance, the virtual game loaded by the user may use game facts leading up to the at-bat the user has selected. For instance, the opposing team, the stadium, the score, the time of day, the batter, the pitcher, and the sequence of pitches thrown by the pitcher may be used to provide the user with a virtual replay of at least that portion of the baseball game that the user can affect via input (e.g., swinging and aiming the virtual bat). In replaying the selected portion of the live event, the entire event may be virtualized. As such, referring to the baseball example, the pitcher, stadium, field, fielders, batter, and ball may all be replaced by virtual objects, with one (or more) of the virtual objects, such as the batter, being controlled by the user. As such, this may resemble a video game instantiated with data from the live event. In some embodiments, a portion of the live event may involve a playback of a video feed of the live event with a virtual object that is controlled by the user being augmented. Referring again to the example of the baseball game, the pitcher, stadium, fielders, and field may be replayed from the video feed; the batter and/or ball may be virtualized. As such, the user may control the batter and swing at a virtual ball that has taken the place of the real ball present in the video feed. Besides baseball, such reenactment of a portion of a live event may be applied to various forms of sporting events, such as football, soccer, tennis, golf, hockey, basketball, cricket, racing, skiing, gymnastics, and track and field events. Other forms of live events, besides sports, may also be reenacted using such techniques.

Figure 15A:
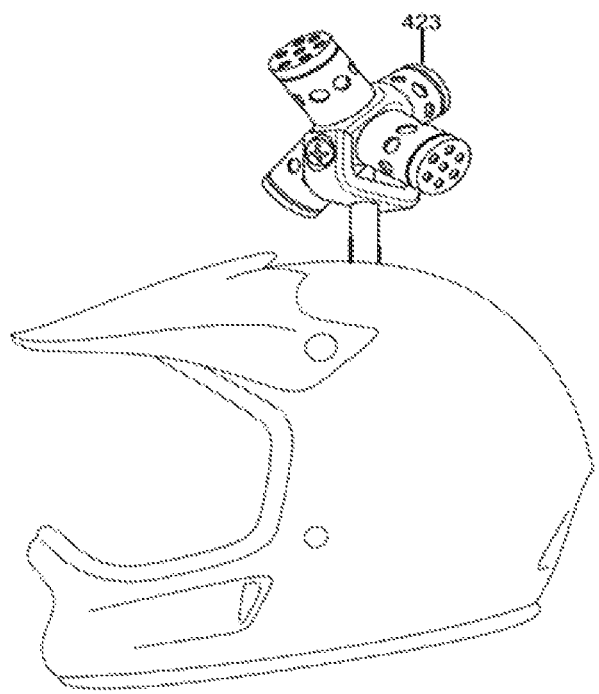
FIG. 15A shows an exemplary virtual reality camera mounted on a gear.

FIG. 15A shows a multi-headed camera array 423 that may be at least part of a modular camera system, with each camera forming a module of the modular camera system. The camera array has a flexible structure so that it is easy to remove a particular camera module from the camera array and to add new camera modules to the camera array. The camera modules in the camera array may be configured in different geometries. For example, the camera array includes multiple camera modules arranged in a line, a cylinder, a sphere, or another geometry. Each camera module may be configured to point to a different direction so that the camera array may capture an object or a scene from multiple directions at the same time.

The camera system described herein may additionally include a set of algorithms for processing the video data captured by the camera array. The set of algorithms are stored on a non-transitory memory for converting the input across multiple camera modules into a single stream of 3D video (e.g., a single compressed stream of 3D video data). The set of algorithms may be implemented in one or more "modules". For example, the set of algorithms includes color correction algorithms for smoothing and correcting colors in the video data. In another example, the set of algorithms may be implemented in software that stitches the video data from multiple cameras into two large-format, panoramic video streams for left and right eye viewing, and encodes and compresses the video using a standard MPEG format or other suitable encoding/compression format.

The camera array 423 may be constructed using various configurations. For example, the camera modules may be configured in different geometries (e.g., a sphere, a line, a cylinder, a cone, a cube, etc.) with the corresponding lenses 113 facing in different directions. For example, the camera modules are positioned within the camera array 423 in a honeycomb pattern where each of the compartments form an aperture where a camera module may be inserted. In another example, the camera array 423 includes multiple lenses along a horizontal axis and a smaller number of lenses on a vertical axis.

In some embodiments, the camera modules in the camera array 423 are oriented around a sphere in different directions with sufficient diameter and field-of-view to capture enough view disparity to render stereoscopic images.

The camera array 423 has a flexible structure so that a particular camera module may be removed from the camera array 423 easily. In some embodiments, the camera modules are rotationally symmetrical such that a camera module may be inserted into the housing, removed, rotated 90 degrees, and reinserted into the housing. In this example, the sides of the housing may be equidistant, such as a camera module with four equidistant sides. This allows for a landscape orientation or a portrait orientation of the image frames without changing the base. In some embodiments, the lenses and the camera modules are interchangeable. New camera modules may also be added to the camera array 423. In some embodiments, the camera modules in the camera array 423 are positioned to have a sufficient field-of-view overlap so that all objects can be seen by more than one view point. In some embodiments, having the camera array 423 configured so that an object may be viewed by more than one camera may be beneficial for correcting exposure or color deficiencies in the images captured by the camera array 423. Other benefits include disparity/depth calculations, stereoscopic reconstruction, and the potential to perform multi-camera high-dynamic range (HDR) imaging using an alternating mosaic pattern of under- and over-exposure across the camera array.

In some embodiments, the camera array 423 may also include a microphone array for capturing sound from all directions. For example, the microphone array may include a Core Sound Tetramic soundfield tetrahedral microphone array following the principles of ambisonics, enabling reconstruction of sound from any arbitrary direction. In another example, the microphone array includes the Eigenmike, which advantageously includes a greater number of microphones and, as a result, can perform higher-order (i.e. more spatially accurate) ambisonics. The microphone may be mounted to the top of the camera array 423, be positioned between camera modules, or be positioned within the body of the camera array 423. The result can then be rendered as an immersive video and a user can view the video with computer annotations thereon for augmented reality purposes. In one implementation, the event may be a live event, for example, but is not limited to, a football match, a cricket match, a basketball match, a theatre, a concert, and the like. In one embodiment, the augmented reality content may include, but is not restricted to, live content associated with an event, recorded content associated with an event, a curated content, an advertising content, or a combination thereof. In another embodiment, the augmented reality content may include, but is not restricted to, information related to a service available at an event, a venue of an event, a status of a service, or a combination thereof. The system 100 may also provide the augmented reality content associated with, but is not restricted to, a venue of an event, duration of an event, a location of an event, or a combination thereof, in another implementation.

One embodiment allows combined augmented reality and virtual reality on the display. The method may include selectively allowing a transmission of light from a local environment of the user based on a visualization mode of the display object. The visualization mode may be one of an augmented reality mode, a virtual reality mode, and a combination of augmented and virtual reality modes.

In another embodiment, sensors may be placed to track eye movement as well as hand gestures and verbal commands. The method may further comprise capturing a field-of-view image of each of the user's eyes. The captured field of view image may be used to estimate a head pose of the user. The captured field-of-view image may be used to convert at least one physical object to a physically rendered virtual object, and to display the physically rendered virtual object to the user. In another embodiment, sensors may be placed to track eye movement as well as hand gestures and verbal commands. Then, a method comprises tracking a movement of a user's eyes, estimating a depth of focus of the user's eyes based on the tracked eye movement, modifying a light beam associated with a display object based on the estimated depth of focus such that the display object appears in focus, and projecting the modified light beam into the user's eyes. The diameter of the projected light beam projected to the user's eyes may be less than 0.7 mm.

For the athlete/participant who wish to enhance their gaming via augmented or virtual reality, features may include the following:

1. A method for using augmented reality, the method comprising: receiving, by a computerized device, a data stream with a 360 degree view of a live event on each participant, wherein the data stream comprises live video augmented with positions of team mates and opposing players and recommends a play routine based on live field condition and positions of other players, wherein the user can select a point of view from a selected participant.

2. The method for using augmented reality of claim 1, wherein the user plays in a virtual reality version of the live event.

3. The method for using augmented reality of claim 1, wherein the live event is a sporting event.

4. The method of claim 7, wherein the live event comprises: soccer, football, basketball, tennis, boxing, car racing, golf, ice hockey, badminton, volleyball, cycling, swimming, snooker, martial arts, rugby, motorbike, hockey, table tennis, horse racing, gymnastics, handball, figure skating, wrestling, skiing, diving, skating, archery, sailing, wrestling, fencing, equestrian, rowing, surfing, Beach Volleyball, Pool/Billiards, Lacrosse, Windsurfing, Polo, Tenpin Bowling, Racquetball, Competitive Climbing, Mountain Biking.

Figure 15B:
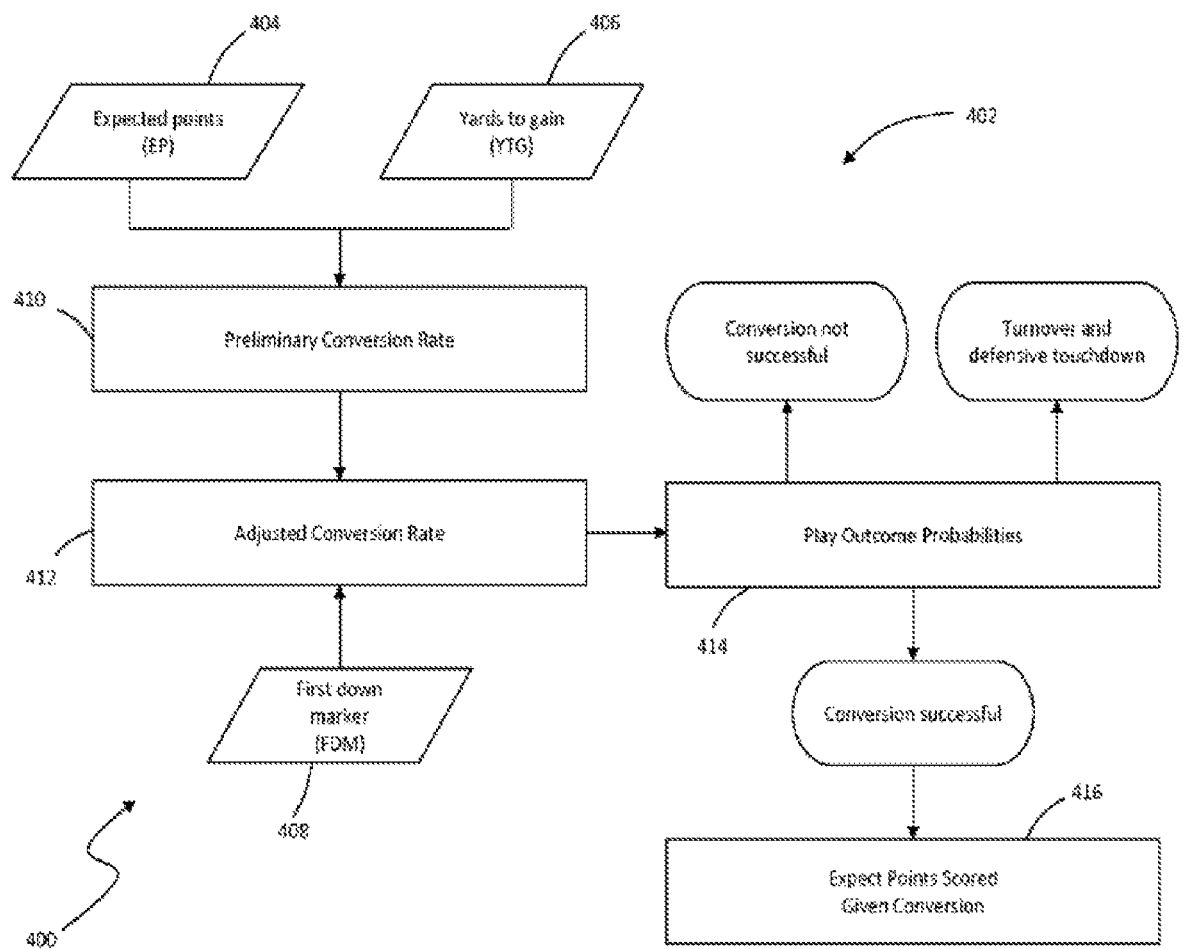
FIG. 15B shows exemplary augmented reality real-time coaching of a player such as a quarterback during fourth down.

FIG. 15 shows an exemplary recommender to aid an athlete in improving the game. For example, the process can recommend a strategy in light of the opponent's historical performance. In tennis, a player's historical weakness can be ascertained and a recommendation can be made to optimize success. In a football example, a fourth down module 400 may include a Football recommender, a Field Goal algorithm, and a Punt algorithm. The Football recommender determines the probability of each potential play outcome associated with the Go For It coaching decision. The Field Goal algorithm determines the probability of each potential play outcome associated with the Field Goal coaching decision. The Punt algorithm 1102 determines the probability of each potential play outcome associated with the Punt coaching decision. As shown in FIG. 15B, the Football recommender 402 determines the probability of each potential play outcome associated with the Go For It coaching decision on a fourth down play. The Football recommender 402 receives an expected points (EP) input from the expected points module 300 at block 404, a yards to gain (YTG) for first down input at block 406, and a first down marker (FDM) yard line input at block 408. Preliminary Conversion Rate: At block 410, the Football recommender 402 uses the team's EP value from block 404 and the YTG distance from block 406 to determine a preliminary first down conversion rate based on historical conversion data. Historical first down conversion data is shown in the form of a chart in FIG. 5, where YTG distances are presented on the x-axis and average first down conversion rates are presented on the y-axis. This historical data shows that the likelihood of a first down conversion decreases as the YTG distance increases. Individual lines or equations may be presented to account for various EP values. For simplicity, FIG. 5 shows three lines to account for scenarios in which the offense and defense are an equal match with the same EP values (NEU), the offense has the advantage (OFF AD), and the defense has the advantage (DEF AD). The historical data presented in FIG. 5 shows that stronger offenses will convert first downs versus weaker defenses (OFF AD) more often than weaker offenses will convert first downs versus stronger defenses (DEF AD). Similar lines may be provided for specific EP values (e.g., 7-66 points). By determining the first down conversion rate at each YTG distance for each offensive match-up, the Football recommender 402 is able to predict the likelihood of a first down conversion with great precision.

Inside an opponent's 20-yard line (i.e., in the Red Zone), it becomes more difficult to convert for a first down as the space on the field from which to work becomes more limited. As the FDM gets closer to the end zone and the YTG distance increases, the challenge of converting a first down gets progressively more difficult versus similar scenarios outside of the Red Zone. To account for the challenge of converting a first down in the Red Zone, the Football recommender 402 may multiply the preliminary conversion rate by a field position multiplier at block 412 based on the YTG distance from block 406 and the FDM yard line from block 408 (where 100 represents the opponent's goal line. As an example, take a team that normally has a 50% fourth down conversion rate with 2 YTG. If the team faces a fourth down play with 2 YTG outside of the Red Zone, the conversion rate may remain at 50%. However, if the team faces a fourth down play with 2 YTG in the Red Zone, such as from the opponent's 2-yard line when the FDM is on the opponent's goal line (FDM=100), the normal 50% conversion rate may be multiplied by the corresponding field position multiplier of 85.5% to arrive at a lower adjusted conversion rate of 42.7%. The process may adjust team's first down conversion rate at block 412 based on particular strengths of his team. In one embodiment, the Football recommender 402 multiplies the conversion rate by one or more additional multipliers, such as a YTG multiplier, which may be specified by the coach. As an example, a team that thrives on running the football might find that it converts short-yardage situations particularly well, because its offense is designed to consistently grind out short gains. However, the same team may have particular difficulty in converting longer-yardage situations because the offense isn't conducive to big plays. In this example, the YTG multiplier may be greater than 100% below 5 YTG to increase the conversion rate in short-yardage situations and less than 100% above 5 YTG to decrease the conversion rate in long-yardage situations. Conversely, a team with an explosive offense may be particularly effective in converting long yardages but may not have the personnel to get short yardage. In this example, the YTG multiplier may be less than 100% below 5 YTG to decrease the conversion rate in short-yardage situations and greater than 100% above 5 YTG to increase the conversion rate in long-yardage situations. The Indianapolis Colts were a great example of this during much of the Peyton Manning era. They were very dangerous in long-yardage situations due to the quality of their passing game, but due to a poor running game, they often failed to convert in short-yardage scenarios. The Football recommender 402 may calculate the probability of a turnover and defensive touchdown as a function of the EP value from block 404 and the FDM yard line from block 408. This probability may be as low as about 0.1% and as high as about 0.5%. At block 414, the Football recommender 402 assigns probabilities to each potential conversion outcome. The Football recommender 402 may determine not only the likelihood of a first down conversion at block 412, but also how likely the team is to score points if the conversion is successful at block 416. After a successful conversion, the team could get just enough yards to get the first down and still not score any points on the drive, or it could score a touchdown on the very same play or a subsequent play of the same drive. Therefore, the Football recommender 402 may take into account the potential upside of the drive should the fourth down play be successful at any field position. At block 416, the Football recommender 402 uses the team's EP value from block 404 and the FDM yard line from block 408 to determine the points scored given conversion based on historical scoring data. Historical scoring data is shown in the form of a chart in FIG. 6, where FDM yard lines are presented on the x-axis (with 0 representing the team's own goal line and 100 representing the opponent's goal line) and average points scored given conversion are presented on the y-axis. This historical data shows that the likelihood of scoring points increases as the FDM approaches the opponent's goal line. Individual lines or equations may be presented to account for various EP values. For simplicity, FIG. 6 shows three lines to account for scenarios in which the offense and defense are an equal match with the same EP values (NEU), the offense has the advantage (OFF AD), and the defense has the advantage (DEF AD). The historical data presented in FIG. 6 shows that stronger offenses will score more points versus weaker defenses (OFF AD) than weaker offenses will score versus stronger defenses (DEF AD). Similar lines may be provided for specific EP values (e.g., 7-66 points). In this manner, the augmented reality system can enhance the game.

For viewers who wish to participate via augmented or virtual reality, features may include the following:

1. A method for using augmented reality, the method comprising: receiving, by a computerized device, a data stream with a 360 degree view of a live event on each participant, wherein the data stream comprises live video, wherein: the live video comprises a live object; receiving, by the computerized device, input from a user, wherein the input from the user affects behavior of a virtual object; and presenting, by the computerized device, the live event augmented by the virtual object, wherein a behavior of the live object of the live event affects the behavior of the virtual object and each participant, wherein the user can select a point of view from a selected participant.

2. The method for using augmented reality of claim 1, wherein: the virtual object is presented such that the virtual object appears to compete with the live object.

3. The method for using augmented reality of claim 1, wherein the live event is a sporting event.

4. The method for using augmented reality of claim 1, further comprising: receiving, by the computerized device, data corresponding to a second virtual object from a remote computerized device; and displaying, by the computerized device, the live event augmented by the virtual object further augmented with the second virtual object.

5. The method for using augmented reality of claim 4, wherein the behavior of the second virtual object is affected by a second user.

6. The method for using augmented reality of claim 4, further comprising: modifying, by the computerized device, behavior of the virtual object in response to the second virtual object.

7. A method for using augmented reality, the method comprising: receiving, by a computerized device, data corresponding to a live event; presenting, by the computerized device, the live event up to a point in time; presenting, by the computerized device, a virtual event at least partially based on an event that occurred during the live event earlier than the point in time; receiving, by the computerized device, input linked with the virtual event, wherein the input is received from a user; and presenting, by the computerized device, an outcome of the virtual event, wherein the outcome is at least partially based on the input received from the user.

8. The method for using augmented reality of claim 7, wherein: the virtual event is presented at least starting when the live event is stopped.

9. The method of claim 7, wherein the live event is a sporting event.

10. The method of claim 7, wherein the live event comprises: soccer, football, basketball, tennis, boxing, car racing, golf, ice hockey, badminton, volleyball, cycling, swimming, snooker, martial arts, rugby, motorbike, hockey, table tennis, horse racing, gymnastics, handball, figure skating, wrestling, skiing, diving, skating, archery, sailing, wrestling, fencing, equestrian, rowing, surfing, Beach Volleyball, Pool/Billiards, Lacrosse, Windsurfing, Polo, Tenpin Bowling, Racquetball, Competitive Climbing, Mountain Biking.

11. A method for using virtual reality, the method comprising: receiving, by a computerized device, a data stream with a 360 degree view of a computer generated event on each participant, wherein the data stream comprises live video, wherein: the live video comprises a live object; receiving, by the computerized device, input from a user, wherein the input from the user affects behavior of a virtual object; and presenting, by the computerized device, the live event augmented by the virtual object, wherein a behavior of the live object of the live event affects the behavior of the virtual object and each participant.

12. A method for using augmented reality and virtual reality, the method comprising: receiving, by a computerized device, a data stream with a 360 degree view of a live event on each participant, wherein the data stream comprises live video, wherein: the live video comprises a live object; receiving, by the computerized device, input from a user, wherein the input from the user affects behavior of a virtual object; and presenting, by the computerized device, the live event augmented by the virtual object, wherein a behavior of the live object of the live event affects the behavior of the virtual object and each participant, and wherein the virtual reality is rendered by switching the display from an augmented view to a virtual reality view by fading out the augmented view on the display to show only the virtual reality view and switching back when augmented reality view is desired.

Moreover, the viewers can collaboratively read the situation and recommend a strategy in real-time to improve viewer participation. In this manner, 1. A method for participating in a game, the method comprising: collecting from viewers of a game one or more state change events during a game; determining whether a series of the collected state change events are a known pattern; requesting, when the series of the collected state change events is an unknown pattern, viewers of the game to identify what caused the collected state change events; and judging, by the viewers, a best reason among the identified causes of the collected state change events.

2. The method of claim 1, comprising running a lottery to decide which recommendation is used for the next play in the game.

3. The method of claim 1, further comprising: compensating at least one viewer who is judged to have the best reason among the identified causes of the collected state change events.

4. The method of claim 1, further comprising: storing as the known pattern, the best reason among the identified causes of the collected state change events when one of the pattern is repeated greater than a threshold number of repeats, and the number of the viewers who agree with the corresponding best reason is greater than a threshold number of users.

5. The method of claim 4, further comprising: associating with the stored best reason a corrective action to be taken in response to a future corresponding the collected state change events.

6. The method of claim 4, further comprising: displaying to the other viewers and players, when the stored best reason is known, the occurrence of the stored best reason.

7. The method of claim 5, further comprising: transmitting the stored best reason to other viewers.

8. The method of claim 1, wherein the series of the collected state change events are at least two state change events that occur within a threshold period of time from each other.

Recognition of Exercise Pattern and Tracking of Calorie Consumption

Figure 16A:
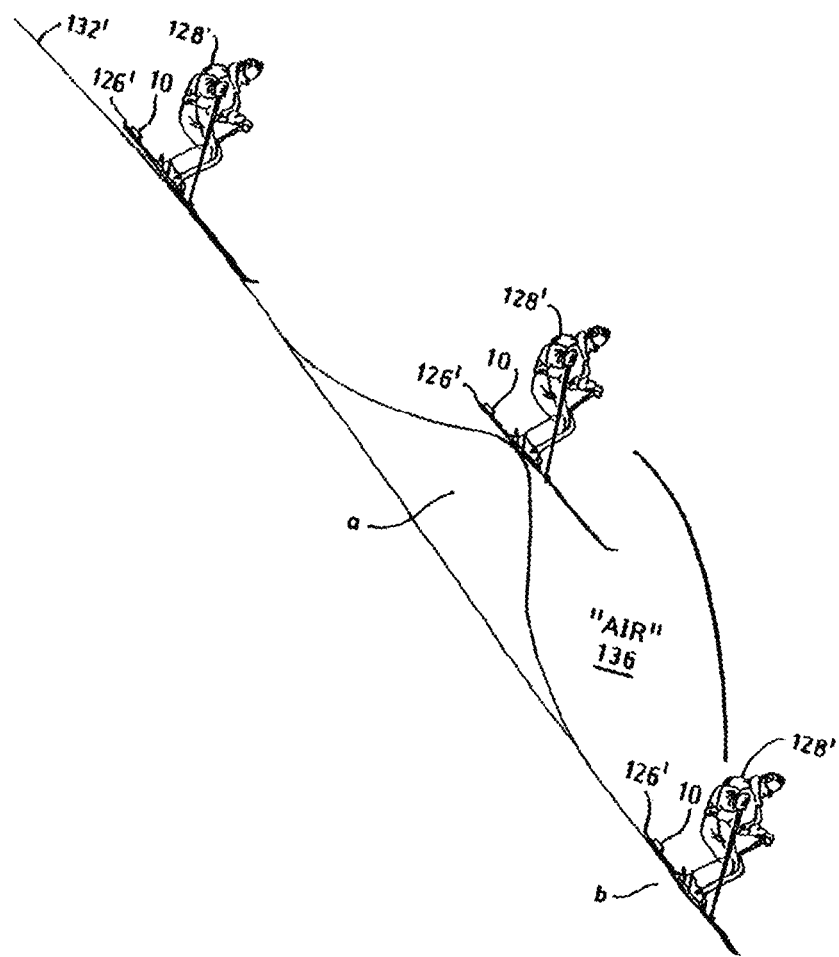

FIG. 16A illustrates the positions of a ski 126' and skier 128' during a lofting maneuver on the slope 132'. The ski 126' and skier 128' speed down the slope 132' and launch into the air 136 at position "a," and later land at position "b" in accord with the well-known Newtonian laws of physics. With an airtime sensor, described above, the unit 10 calculates and stores the total airtime that the ski 126' (and hence the skier 128') experiences between the positions "a" and "b" so that the skier 128' can access and assess the "air" time information. Airtime sensors such as the sensor 14 may be constructed with known components. Preferably, the sensor 14 incorporates either an accelerometer or a microphone. Alternatively, the sensor 14 may be constructed as a mechanical switch that detects the presence and absence of weight onto the switch. Other airtime sensors 14 will become apparent in the description which follows. The accelerometer senses vibration—particularly the vibration of a vehicle such as a ski or mountain bike—moving along a surface, e.g., a ski slope or mountain bike trail. This voltage output provides an acceleration spectrum over time; and information about airtime can be ascertained by performing calculations on that spectrum. Based on the information, the system can reconstruct the movement path, the height, the speed, among others and such movement data is used to identify the exercise pattern. For example, the skier may be interested in practicing mogul runs, and the system can identify foot movement and speed and height information and present the information post exercises as feedback. Alternatively, the system can make live recommendations to improve performance to the athlete.

Figure 16B:
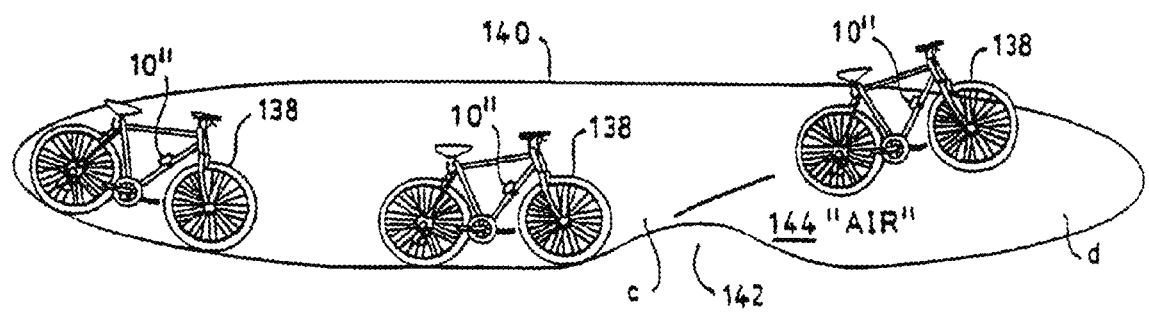
Figure 16C:
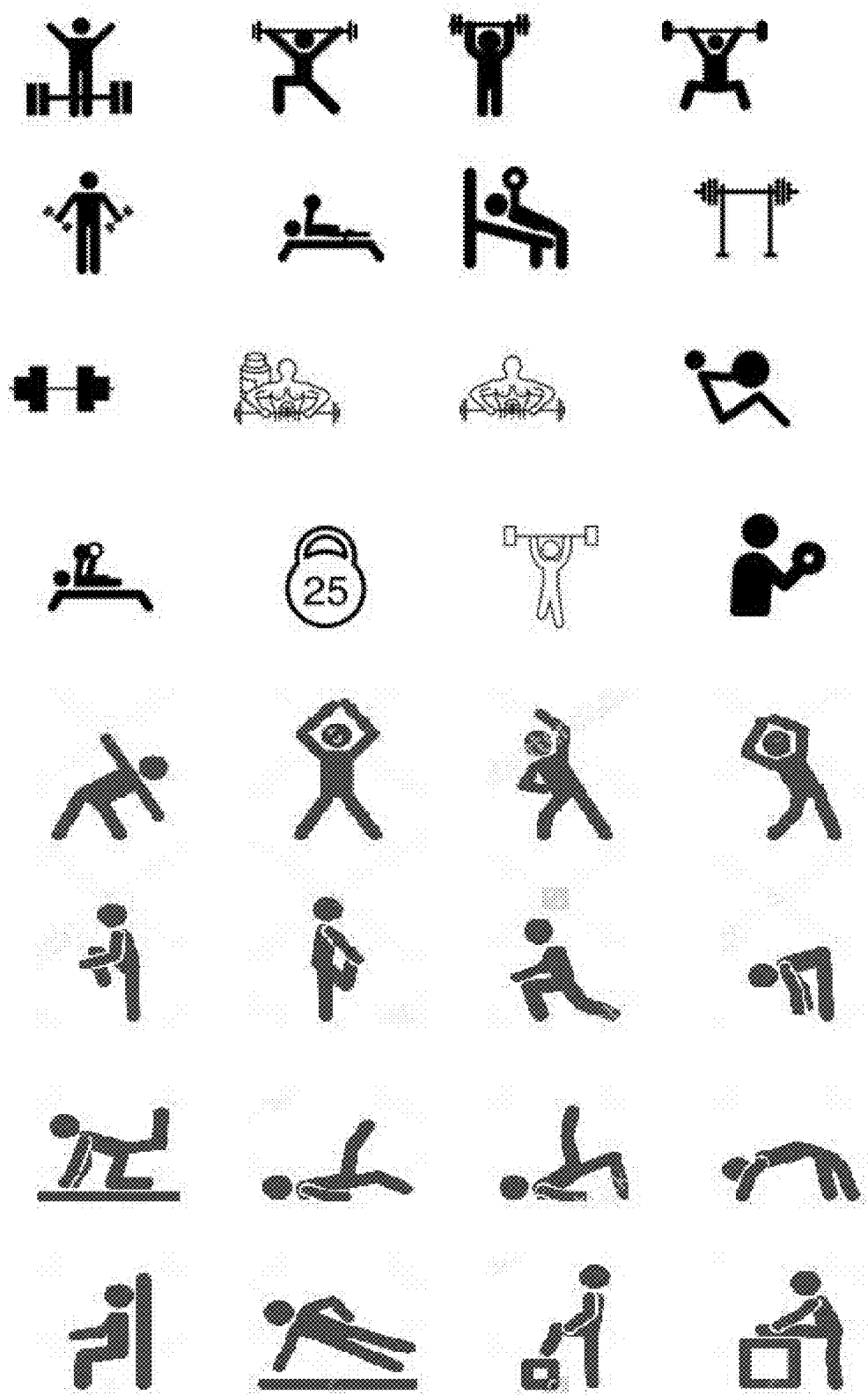

FIG. 16B illustrates a sensing unit 10" mounted onto a mountain bike 138. FIG. 16B also shows the mountain bike 138 in various positions during movement along a mountain bike race course 140 (for illustrative purposes, the bike 138 is shown without a rider). At one location "c" on the race course 140, the bike 138 hits a dirt mound 142 and catapults into the air 144. The bike 138 thereafter lands at location "d". As above, with speed and airtime sensors, the unit 10 provides information to a rider of the bike 138 about the speed attained during the ride around the race course 140; as well as information about the airtime between location "c" and "d". In this case, the system can recommend a cadence to be reached by the rider, strengthen of abdominals, back and arms, for example.

For golf exercise, It is beneficial to require the golfer to swing the golf club a plurality of times at each swing position to account for variations in each swing. The swing position at which the golf club is swung can be determined by analysis of the measured acceleration provided by the accelerometer, e.g., the time at which the acceleration changes. Data obtained during the training stage may be entered into a virtual table of swing positions and estimated carrying distances for a plurality of different swing positions and a plurality of different swings. A sample format for such a table is as follows, and includes the averaged carrying distance for each of four different swing positions. The swing analyzer provides a golfer with an excellent estimation of the carrying distance of a golf ball for a golf club swing at a specific swing position because it has been trained on actual swings by the golfer of the same club and conversion of information about these swings into estimated carrying distances. The golfer can improve their golf game since they can better select a club to use to hit a golf club for different situations during a round of golf. Also, the swing pattern is used to identify each club path responsible for the curve of any shot and this information is used to improve the golfer. The direction of the club path relative to the target, out-to-in (fade pattern) or in-to-out (draw pattern), is what I refer to as a players swing pattern. Players that swing from in-to-out will tend to hit draws and players that swing from out-to-in will tend to hit fades. Where the ball is struck on the face of the driver (strike point) can drastically alter the effect of a players swing pattern on ball flight. Thus, the camera detects where the ball is struck, and a computer physics model of ball behavior is presented to the golfer to improve the score. Shots struck off the heel will tend to fade more or draw less and shots struck off the toe will tend to draw more or fade less. Thus, camera images of the shots struck of heel or toe can also be used to provide pattern recognition/prediction and for training purposes.

For tennis, examples of motions determined for improvement are detailed next. The system can detect if the continental grip is achieved. Throwing Action pattern is also detected, as the tennis serve is an upwards throwing action that would deliver the ball into the air if it were a baseball pitch. Ball Toss improvements can be determined when the player lines the straight arm up with the net post and release the ball when your hand reaches eye level. The system checks the forward direction so the player can drive weight (and built up momentum) forward into the ball and into the direction of the serve.

The sensors can work with a soccer training module with kinematics of ball control, dribbling, passing, crossing, shooting, heading, volleying, taking throw-ins, penalties, corner kicks and free kicks, tackling, marking, juggling, receiving, shielding, clearing, and goalkeeping. The sensors can work with a basketball training module with kinematics of crossover dribble, behind back, pull back dribble, low dribble, basic dribble, between legs dribble, Overhead Pass, Chest Pass, Push Pass, Baseball Pass, Off-the-Dribble Pass, Bounce Pass, Jump Shot, Dunk, Free throw, Layup, Three-Point Shot, Hook Shot.

The sensors can work with a baseball training module with kinematics of Hitting, Bunting, Base Running and Stealing, Sliding, Throwing, Fielding Ground Balls, Fielding Fly Balls, Double Plays and Relays, Pitching and Catching, Changing Speeds, Holding Runners, Pitching and Pitcher Fielding Plays, Catching and Catcher Fielding Plays.

Figure 16D:
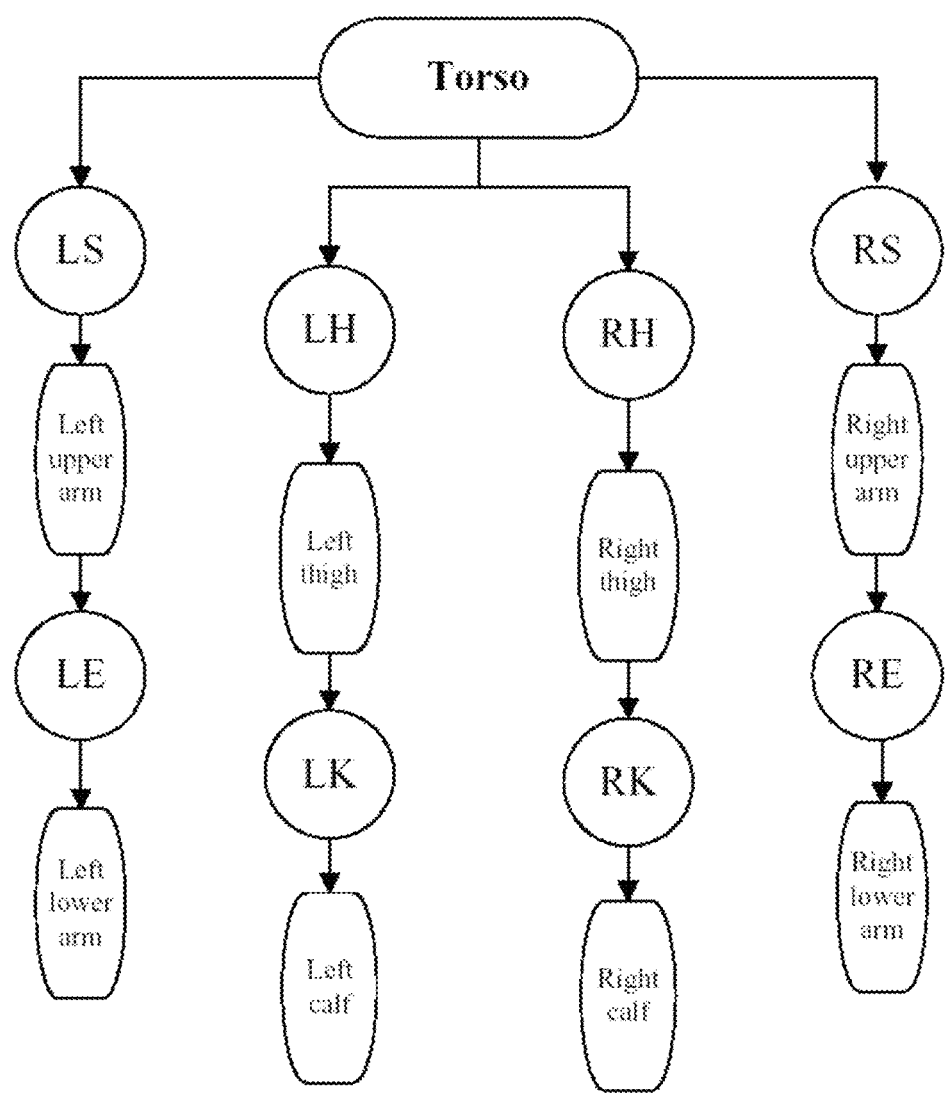
FIG. 16D shows a kinematic modeling for detecting exercise motion which in turn allows precision coaching suggestions.

For weight training, the sensor can be in gloves as detailed above, or can be embedded inside the weight itself, or can be in a smart watch, for example. The user would enter an app indicating that the user is doing weight exercises and the weight is identified as a dumbbell, a curl bar, and a bar bell. Based on the arm or leg motion, the system automatically detects the type of weight exercise being done. In one embodiment shown in FIG. 15C, with motion patterns captured by glove and sock sensors, the system can automatically detect the following exemplary exercise:

Upper Body:
Chest: Barbell Bench Presses, Barbell Incline Presses, Dumbbell Bench Presses, Dumbbell Incline Presses, Dumbbell Flyes, Cable Crossovers
Back: Pull-Ups, Wide-Grip Lat Pulldowns, One-Arm Dumbbell Rows, Seated Cable Rows, Back Extensions, Straight Arm Pulldowns
Shoulders: Seated Dumbbell Presses, Front Raises, Lateral Raises, Reverse Flyes, Upright Cable Rows, Upright Barbell Rows
Biceps: Alternate Dumbbell Curls, Barbell Curls, Preacher Curls, Concentration Curls, Cable Curls, Hammer Curls
Triceps: Seated Triceps Presses, Lying Triceps Presses, Triceps Kickbacks, Triceps Pushdowns, Cable Extensions, Bench Dips
Lower Body
Quadriceps: Barbell Squats, Leg Presses, Leg Extensions
Hamstrings: Dumbbell Lunges, Straight-Leg Deadlifts, Lying Leg Curls
Calves: Seated Calf Raises, Standing Heel Raises
Abs: Floor Crunches, Oblique Floor Crunches, Decline Crunches, Decline Oblique, Hanging Knee Raises, Reverse Crunches, Cable Crunches, Cable Oblique Crunches In one implementation in FIG. 16D, an HMM is used to track weightlifting motor skills or enthusiast movement patterns. Human movement involves a periodic motion of the legs. Regular walking involves the coordination of motion at the hip, knee and ankle, which consist of complex joints. The muscular groups attached at various locations along the skeletal structure often have multiple functions. The majority of energy expended during walking is for vertical motion of the body. When a body is in contact with the ground, the downward force due to gravity is reflected back to the body as a reaction to the force. When a person stands still, this ground reaction force is equal to the person's weight multiplied by gravitational acceleration. Forces can act in other directions. For example, when we walk, we also produce friction forces on the ground. When the foot hits the ground at a heel strike, the friction between the heel and the ground causes a friction force in the horizontal plane to act backwards against the foot. This force therefore causes a breaking action on the body and slows it down. Not only do people accelerate and brake while walking, they also climb and dive. Since reaction force is mass times acceleration, any such acceleration of the body will be reflected in a reaction when at least one foot is on the ground. An upwards acceleration will be reflected in an increase in the vertical load recorded, while a downwards acceleration will be reduce the effective body weight. Zigbee wireless sensors with tri-axial accelerometers are mounted to the enthusiast on different body locations for recording, for example the tree structure as shown in FIG. 16D. As shown therein, sensors can be placed on the four branches of the links connect to the root node (torso) with the connected joint, left shoulder (LS), right shoulder (RS), left hip (LH), and right hip (RH). Furthermore, the left elbow (LE), right elbow (RE), left knee (LK), and right knee (RK) connect the upper and the lower extremities. The wireless monitoring devices can also be placed on upper back body near the neck, mid back near the waist, and at the front of the right leg near the ankle, among others.

The sequence of human motions can be classified into several groups of similar postures and represented by mathematical models called model-states. A model-state contains the extracted features of body signatures and other associated characteristics of body signatures. Moreover, a posture graph is used to depict the inter-relationships among all the model-states, defined as PG(ND,LK), where ND is a finite set of nodes and LK is a set of directional connections between every two nodes. The directional connection links are called posture links. Each node represents one model-state, and each link indicates a transition between two model-states. In the posture graph, each node may have posture links pointing to itself or the other nodes.

In the pre-processing phase, the system obtains the human body profile and the body signatures to produce feature vectors. In the model construction phase, the system generate a posture graph, examine features from body signatures to construct the model parameters of HMM, and analyze human body contours to generate the model parameters of ASMs. In the motion analysis phase, the system uses features extracted from the body signature sequence and then applies the pre-trained HMM to find the posture transition path, which can be used to recognize the motion type. Then, a motion characteristic curve generation procedure computes the motion parameters and produces the motion characteristic curves. These motion parameters and curves are stored over time, and if differences for the motion parameters and curves over time is detected, the system then runs the enthusiast through additional tests to confirm the detected motion.

In one exemplary process for determining exercise in the left or right half of the body, the process compares historical left shoulder (LS) strength against current LS strength (3200). The process also compares historical right shoulder (RS) strength against current RS strength (3202). The process can compare historical left hip (LH) strength against current LH strength (3204). The process can also compare historical right hip (RH) strength against current RH strength (3206). If the variance between historical and current strength exceeds threshold, the process generates warnings (3208). Furthermore, similar comparisons can be made for sensors attached to the left elbow (LE), right elbow (RE), left knee (LK), and right knee (RK) connect the upper and the lower extremities, among others.

The system can ask the enthusiast to squeeze a strength gauge, piezoelectric sensor, or force sensor to determine force applied during squeeze. The user holds the sensor or otherwise engages the sensor. The user then applies and holds a force (e.g., compression, torque, etc.) to the sensor, which starts a timer clock and triggers a sampling start indicator to notify the user to continue to apply (maximum) force to the sensor. Strength measurements are then sampled periodically during the sampling period until the expiration of time. From the sampled strength data, certain strength measurement values are selected, such as the maximum value, average value(s), or values obtained during the sampling period. The user can test both hands at the same time, or alternatively he may test one hand at a time. A similar approach is used to sense leg strength, except that the user is asked to pushed down on a scale to determine the foot force generated by the user.

In one embodiment, exercise motion data acquired by the accelerometer or multi-axis force sensor is analyzed, as will be discussed below, in order to determine the motion of each exercise stroke during the exercise session (i.e., horizontal vertical or circular). In another embodiment for detecting exercise motion using accelerometer, the first minimum discovered during the scanning is noted as the first xmin and considered to be the start of the first brushstroke. The first maximum x value following the first minimum x value is located and construed to be the middle of the first exercise stroke (where exercise motion changes from one direction to the other). The next xmin value indicates the end of the first brushstroke and the beginning of the next brushstroke. The computer records the data for each brushstroke and continues on through the data to find the next brushstroke, recording each successive motion in memory. For the first brushstroke, the maximum and minimum values of the x coordinate (xmax and xmin) are determined. The Y-direction lengths, Ly1 and Ly2, between the data points just before and just after each of xmax and xmin (xmax+1, xmax−1, and Xmin+1, xmin−1) are then determined. The length Lx along the x axis, between xmax and xmin, is also determined. Next, if Lx is less than 2 and either Ly1 or Ly2 is greater than one, then the motion is construed to be vertical. If Ly1 and Ly2 are both less than one, then the motion is construed to be horizontal. Otherwise, the motion is construed to be circular.

Data obtained from the gyroscope, if one is used, typically does not require a complex analysis. To determine which side of the mouth is being brushed at a particular time, the gyroscope data is scanned to determine when the rotational orientation is greater than 180 degrees, indicating the left side, and when it is less than 180 degrees, indicating the right side. As explained above, top and bottom and gum brushing information can also be obtained, without any calculations, simply by examining the data. The time sequence of data that is acquired during exercise and analyzed as discussed above can be used in a wide variety of ways.

In one embodiment, the accelerometers distinguish between lying down and each upright position of sitting and standing based on the continuous output of the 3D accelerometer. The system can detect (a) extended time in a single position; (b) extended time sitting in a slouching posture (kyphosis) as opposed to sitting in an erect posture (lordosis); and (c) repetitive stressful movements, such as may be found on some manufacturing lines, while typing for an extended period of time without proper wrist support, or while working all day at a weight lifting exercise, among others. In one alternative embodiment, angular position sensors, one on each side of the hip joint, can be used to distinguish lying down, sitting, and standing positions. In another embodiment, the system repeatedly records position and/or posture data over time. In one embodiment, magnetometers can be attached to a thigh and the torso to provide absolute rotational position about an axis coincident with Earth's gravity vector (compass heading, or yaw). In another embodiment, the rotational position can be determined through the in-door positioning system as discussed above.

To improve a golf swing, the complex motion of the body first starts with the stance. The system checks that the golfer has a low center of gravity to remain balanced throughout the swing path. The swing starts with the arms moving back in a straight line. When the club head reaches the level of the hip, two things happen: there is a stern wrist cock that acts as a hinge along with the left knee (for a right handed swing), building up its torque by moving into the same line as the belly button before the start of the upswing. As the swing continues to the top of the backswing (again for right handed golf swing), the golfer's left arm should be perfectly straight and his right arm should be hinged at the elbow. The downswing begins with the hips and the lower body rather than the arms and upper body, with emphasis on the wrist cock. As the golfer's hips turn into the shot, the right elbow will drop straight down, hugging the right side of the golfer's torso. As the right elbow drops, the wrists begin to snap through from the wrist cock in the backswing. A solid extension of the arms and good transfer of body should put the golfer leaning up on his right toe, balanced, with the golf club resting on the back of the golfers neck. Importantly, all of the movements occur with precise timing, while the head remains completely still with eyes focused on the ball throughout the entire swing.

The system can identify illnesses and prevent overexertion leading to illnesses such as a stroke. Depending on the severity of the stroke, enthusiasts can experience a loss of consciousness, cognitive deficits, speech dysfunction, limb weakness, hemiplegia, vertigo, diplopia, lower cranial nerve dysfunction, gaze deviation, ataxia, hemianopia, and aphasia, among others. Four classic syndromes that are characteristically caused by lacunar-type stroke are: pure motor hemiparesis, pure sensory syndrome, ataxic hemiparesis syndrome, and clumsy-hand dysarthria syndrome. enthusiasts with pure motor hemiparesis present with face, arm, and leg weakness. This condition usually affects the extremities equally, but in some cases it affects one extremity more than the other. The most common stroke location in affected enthusiasts is the posterior limb of the internal capsule, which carries the descending corticospinal and corticobulbar fibers. Other stroke locations include the pons, midbrain, and medulla. Pure sensory syndrome is characterized by hemibody sensory symptoms that involve the face, arm, leg, and trunk. It is usually the result of an infarct in the thalamus. Ataxic hemiparesis syndrome features a combination of cerebellar and motor symptoms on the same side of the body. The leg is typically more affected than the arm. This syndrome can occur as a result of a stroke in the pons, the internal capsule, or the midbrain, or in the anterior cerebral artery distribution. enthusiasts with clumsy-hand dysarthria syndrome experience unilateral hand weakness and dysarthria. The dysarthria is often severe, whereas the hand involvement is more subtle, and enthusiasts may describe their hand movements as "awkward." This syndrome is usually caused by an infarct in the pons. Different patterns of signs can provide clues as to both the location and the mechanism of a particular stroke. The system can detect symptoms suggestive of a brainstem stroke include vertigo, diplopia, bilateral abnormalities, lower cranial nerve dysfunction, gaze deviation (toward the side of weakness), and ataxia. Indications of higher cortical dysfunction-such as neglect, hemianopsia, aphasia, and gaze preference (opposite the side of weakness)—suggest hemispheric dysfunction with involvement of a superficial territory from an atherothrombotic or embolic occlusion of a mainstem vessel or peripheral branch.

To detect muscle weakness or numbness, in one embodiment, the system applies a pattern recognizer such as a neural network or a Hidden Markov Model (HMM) to analyze accelerometer output. In another embodiment, electromyography (EMG) is used to detect muscle weakness. In another embodiment, EMG and a pattern analyzer is used to detect muscle weakness. In yet another embodiment, a pattern analyzer analyzes both accelerometer and EMG data to determine muscle weakness. In a further embodiment, historical ambulatory information (time and place) is used to further detect changes in muscle strength. In yet other embodiments, accelerometer data is used to confirm that the enthusiast is at rest so that EMG data can be accurately captured or to compensate for motion artifacts in the EMG data in accordance with a linear or non-linear compensation table. In yet another embodiment, the EMG data is used to detect muscle fatigue and to generate a warning to the enthusiast to get to a resting place or a notification to a nurse or caregiver to render timely assistance. The amplitude of the EMG signal is stochastic (random) in nature and can be reasonably represented by a Gausian distribution function. The amplitude of the signal can range from 0 to 10 mV (peak-to-peak) or 0 to 1.5 mV (rms). The usable energy of the signal is limited to the 0 to 500 Hz frequency range, with the dominant energy being in the 50-150 Hz range. Usable signals are those with energy above the electrical noise level. The dominant concern for the ambient noise arises from the 60 Hz (or 50 Hz) radiation from power sources. The ambient noise signal may have an amplitude that is one to three orders of magnitude greater than the EMG signal. There are two main sources of motion artifact: one from the interface between the detection surface of the electrode and the skin, the other from movement of the cable connecting the electrode to the amplifier. The electrical signals of both noise sources have most of their energy in the frequency range from 0 to 20 Hz and can be reduced.

In one embodiment, the camera captures facial expression and a code such as the Microsoft Emotion API takes a facial expression in an image as an input, and returns the confidence across a set of emotions for each face in the image, as well as bounding box for the face, using the Face API. The emotions detected are anger, contempt, disgust, fear, happiness, neutral, sadness, and surprise. These emotions are understood to be cross-culturally and universally communicated with particular facial expressions. Alternatively, a marker for emotional arousal is galvanic skin response (GSR), also referred to as skin conductance (SC) or electrodermal activity (EDA). EDA modulates the amount of sweat secretion from sweat glands. The amount of sweat glands varies across the human body, being highest in hand and foot regions (200-600 sweat glands per cm2). While sweat secretion plays a major role for thermoregulation and sensory discrimination, changes in skin conductance in hand and foot regions are also triggered quite impressively by emotional stimulation: the higher the arousal, the higher the skin conductance. It is noteworthy to mention that both positive ("happy" or "joyful") and negative ("threatening" or "saddening") stimuli can result in an increase in arousal—and in an increase in skin conductance. Skin conductance is not under conscious control. Instead, it is modulated autonomously by sympathetic activity which drives human behavior, cognitive and emotional states on a subconscious level. Skin conductance therefore offers direct insights into autonomous emotional regulation. It can be used as alternative to self-reflective test procedures, or—even better—as additional source of insight to validate verbal self-reports or interviews of a respondent. Based on the detected emotion, the exercise can be increased, decreased, or stopped altogether.

Features of the auto-detection of exercise include the following:

1. An exercise system, comprising:
    a processor running the motion analyzer and coupled to a wireless transceiver;
    an accelerometer coupled to the processor; and
    a kinematic motion analysis module executed by the processor to detect exercise type.
2. The system of claim 1, comprising a plurality of smart modules mounted on an exerciser forming a mesh network.
3. The system of claim 1 where the electronic components, sensors, and interconnects of the system monitor, record, process and/or transmit events of interest (such as accelerometers and gyroscopes for impact events, temperature sensors for temperature and/or temperature gradients, pressure sensors, moisture sensors, chemical sensors).
4. The system of claim 1 comprised for sensing and/or monitoring impact events where the sensors are accelerometers, gyroscopes, and/or pressure sensors.
5. The system of claim 1 comprised for sensing and/or monitoring and/or controlling ongoing events where the sensors monitor temperature, temperature gradients, motion, position, environmental or chemical levels, or other such information.
6. The system of claim 1 comprised for sensing events or other information including mounting multiple distributed sensors for obtaining spatial and/or temporal distribution in the data and/or multiple sensors sensing different information and data.
7. The system of claim 1 comprising a camera and an image recognition module to determine kinematic movement.
8. The system of claim 1 including a statistical recognizer to determine kinematic movement.
9. The system of claim 8, comprising a model-state that contains the extracted features of body signatures and other associated characteristics of body signatures.
10. The system of claim 1 comprising links connecting a root node (torso) with connected joint, left shoulder (LS), right shoulder (RS), left hip (LH), and right hip (RH), and left elbow (LE), right elbow (RE), left knee (LK), and right knee (RK) connect upper and lower extremities.

11. The system of claim 1 comprising a posture detection module.
12. The system of claim 1, comprising a module to detect a lying down state and a standing state.
13. The system of claim 1, comprising a hidden markov model module to detect muscle movement and exercise pattern.
14. The system of claim 1 comprising optimizing tennis shots to improve serve, groundstroke, volley, half volley, smash, forehand, backhand, flat, side spin, block, slice, topspin shot, lob, passing shot, dropshot, cross-court shot, down-the-line shot.
15. The system of claim 1, comprising an electromyography (EMG) sensor to detect muscle strength or weakness.
16. The system of claim 1, comprising an emotion detector wherein an exercise can be increased, decreased, or stopped based on detected emotion.
17. The system of claim 17, wherein the detector comprises video detection of faces or a GSR sensor.
18. The system of claim 1 comprising a cloud storage to receive sensor data.
19. The system of claim 1, comprising a golf training module that checks that a golfer has a low center of gravity to remain balanced throughout a swing path, that a swing starts with the arms moving back in a straight line, and when a club head reaches the level of the hip, a wrist cock acts as a hinge along with the left knee (for a right handed swing), building up torque by moving into the same line as the belly button before the start of the upswing. As the swing continues to the top of the backswing (again for right handed golf swing), the golfer's left arm is straight and a right arm is hinged at the elbow.
20. The system of claim 19, wherein the golf training module checks that a downswing begins with the hips and the lower body and as the golfer's hips turn into the shot, the right elbow drops down, hugging the right side of the golfer's torso and wrists begin to snap through from the wrist cock in the backswing.
21. The system of claim 1, comprising a soccer training module with kinematics of ball control, dribbling, passing, crossing, shooting, heading, volleying, taking throw-ins, penalties, corner kicks and free kicks, tackling, marking, juggling, receiving, shielding, clearing, and goalkeeping.
22. The system of claim 1, comprising a basketball training module with kinematics of crossover dribble, behind back, pull back dribble, low dribble, basic dribble, between legs dribble, Overhead Pass, Chest Pass, Push Pass, Baseball Pass, Off-the-Dribble Pass, Bounce Pass, Jump Shot, Dunk, Free throw, Layup, Three-Point Shot, Hook Shot.
23. The system of claim 1, comprising a baseball training module with kinematics of Hitting, Bunting, Base Running and Stealing, Sliding, Throwing, Fielding Ground Balls, Fielding Fly Balls, Double Plays and Relays, Pitching and Catching, Changing Speeds, Holding Runners, Pitching and Pitcher Fielding Plays, Catching and Catcher Fielding Plays.

Data from multiple exercise sessions may be collected and used to compile a history of the user's habits over an extended period of time, enabling the user's trainer to better understand user compliance issues. The trainer can review the data with the user and view the animations of the user's exercise sessions during an office visit, allowing the trainer to better instruct the user in proper brushing technique. The trainer can also review the patient's brushing history over time, to determine whether the patient's exercise technique is improving.

The sensor 14 can be integrated into objects already associated with the sporting activity. In one aspect, the sensing unit is integrated into the ski boot or other boot. In another aspect, the sensing unit is integrated into the binding for a ski boot or snowboarder boot. In still another aspect, the sensing unit is integrated into a ski, snowboard, mountain bike, windsurfer, windsurfer mast, roller blade boot, skate-board, kayak, or other vehicle. Collectively, the objects such as the ski boot and the variety of vehicles are denoted as "implements". Accordingly, when the sensing unit is not "stand alone", the housing which integrates the controller subsystem with one or more sensors and battery can be made from the material of the associated implement, in whole or in part, such that the sensing unit becomes integral with the implement. The universal interface is therefore not desired in this aspect.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The embodiments described herein may include the use of a special purpose or general-purpose computer including various computer hardware or software modules, as discussed in greater detail below.

Embodiments described herein may be implemented using computer-readable media for carrying or having computer-executable instructions or data structures stored thereon. Such computer-readable media may be any available media that may be accessed by a general purpose or special purpose computer. By way of example, and not limitation, such computer-readable media may include tangible computer-readable storage media including RAM, ROM, EEPROM, CD-ROM or other optical disk storage, magnetic disk storage or other magnetic storage devices, or any other storage medium which may be used to carry or store desired program code in the form of computer-executable instructions or data structures and which may be accessed by a general purpose or special purpose computer. Combinations of the above may also be included within the scope of computer-readable media. Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. As used herein, the term "module" or "component" may refer to software objects or routines that execute on the computing system. The different components, modules, engines, and services described herein may be implemented as objects or processes that execute on the computing system (e.g., as separate threads). While the system and methods described herein may be preferably implemented in software, implementations in hardware or a combination of software and hardware are also possible and contemplated. In this description, a "computing entity" may be any computing system as previously defined herein, or any module or combination of modulates running on a computing system. All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

What is claimed is:

1. A system, comprising:
   a processor coupled to a wireless transceiver;
   a camera to capture device environment, wherein the camera determines distances of the neighboring objects from the camera;
   code to change insurance cost based on safe driver behavior as detected by the processor by increasing insurance cost for a first driver behavior and decreasing insurance cost for a second driver behavior, and wherein the processor collects travel data from drivers.

2. The system of claim 1, comprising a pressure sensor, a motion sensor, a finger sensor, a digit motion sensor, an EKG sensor, a bio sensor, a medical sensor, or a temperature sensor.

3. The system of claim 1, comprising a module to follow other third parties or a module to follow other devices in a flock.

4. The system of claim 1, wherein the device comprises a road contacting surface, air contacting surface or water contacting surface.

5. The system of claim 1, comprising a gesture identifying component configured to identify hand or finger gesture to the device.

6. The system of claim 1, comprising an optical positioning system.

7. The system of claim 6, wherein the positioning system comprises a laser positioning system.

8. The system of claim 1, comprising a sensor to detect an imminent impact and activate crash protection for a user.

9. The system of claim 1, comprising a hidden markov model (HMM) or a deep learning machine to detect patterns from the camera and the accelerometer.

10. The system of claim 1, comprising an emotion detector to detect a user condition.

11. The system of claim 1, comprising an accelerometer and a camera to detect a potential impact.

12. The system of claim 1, comprising a cloud computer coupled to the processor to predict an impact and to protect a user for the impact.

13. The system of claim 1, comprising at least a second camera to capture car interior.

14. The system of claim 1, comprising a module to follow other vehicles or a module to follow vehicles in a flock.

15. The system of claim 1, wherein the device comprises a road contacting surface, further comprising a positioning system.

16. The system of claim 1, comprising a gesture identifying component to recognize hand or finger gesture to the device.

17. The system of claim 1, comprising returning from user control to processor control upon user activation.

18. The system of claim 1, wherein prior to taking control, the processor scans the surroundings and determines any obstacles or objects in the immediate vicinity which reduce safety.

19. The system of claim 1, wherein a driver maintains control of the device before entering into an autonomous mode.

20. The system of claim 1, comprising code to relinquish control of the device back to a driver if safe, and otherwise collect travel data from neighboring vehicles and coordinate travel path for a plurality of vehicles to increase safety and decrease travel cost, travel time, energy cost, air pollution.

* * * * *